US006500435B1

(12) United States Patent
Kamp et al.

(10) Patent No.: US 6,500,435 B1
(45) Date of Patent: Dec. 31, 2002

(54) RECOMBINANT VACCINE FOR PREVENTION AND/OR TREATMENT OF PLEUROPNEUMONIA INFECTIONS

(76) Inventors: Elbarte Margriet Kamp, Wijngaard 27, 8212 CC Lelystad (NL); Marinus Adrianus Smits, Mastmeen 18, 3844 KE Harderwijk (NL)

( * ) Notice: Subject to any disclaimer, the term of this patent is extended or adjusted under 35 U.S.C. 154(b) by 0 days.

(21) Appl. No.: 09/062,126

(22) Filed: Apr. 17, 1998

Related U.S. Application Data

(63) Continuation of application No. 08/488,706, filed on Jun. 9, 1995, now Pat. No. 5,994,525, which is a division of application No. 08/138,609, filed on Oct. 15, 1993, now abandoned, which is a continuation of application No. 07/722,971, filed on Jun. 28, 1991, now abandoned.

(51) Int. Cl.[7] ................................................ A61K 39/02

(52) U.S. Cl. ................................ 424/236.1; 424/185.1; 424/190.1; 424/193.1; 424/203.1; 424/234.1; 530/350

(58) Field of Search ........................... 424/185.1, 190.1, 424/193.1, 203.1, 234.1, 236.1; 530/350

(56) References Cited

U.S. PATENT DOCUMENTS

| | | | | |
|---|---|---|---|---|
| 5,648,081 A | | 7/1997 | van den Bosch | 424/255.1 |
| 5,804,190 A | * | 9/1998 | Struck et al. | 424/190.1 |

FOREIGN PATENT DOCUMENTS

| | | | |
|---|---|---|---|
| WO | 91/06653 | * | 5/1991 |

OTHER PUBLICATIONS

Bertram, Can. J. Vet. Res., 54:553 S–56 (1990).
Frey et al., J. Clin. Microbiol., 28:232—6 (1990).
Kamp et al., J. Clin. Microbiol., 27:1187–1991 (1989).
Chang et al., DNA, 8:635–647 (1989).
MacInnes et al., J. Bacteriol., 172:4587–92 (1990).
Strathdee et al., J. Bacteriol. 171:2 916–928 (1989).
Gygi et al., Mol. Microbiology, 4(1): 123–128 (1990).
Strathdee et al., Infect. Immun. 55:121, 3233–6 (1987).
Frey et al., FEMS Microbiol. Lett., 55: 41–45 (1988).
Strathdee et al., J. of Bacteriol., 171:916–928 (1989).
Strathdee et al., J. of Bacteriol., 171:5955–5962 (1989).
Frey et al., Infect. and Immunol., 56:2570–5 (1988).
Devenish et al., Infect. and Immun., 57:3210–13 (1989).
Fedorka–Cray et al., Infect. and Immun., 58:358–365 (1990).
Denevish et al., Infect. and Immun., 58:3892–32 (1990).
Frey et al., Vet., Microbiol., 28:303–312 (1991).
Inzana et al., Microbia Pathogenesis, 10:281–296 (1991).
Frey et al., Vet. Microbiol., 28:61–73 (1991).
Rycroft et al., J. of Gen. Microbiol., 137:561–568 (1991).

* cited by examiner

*Primary Examiner*—Jennifer E. Graser
(74) *Attorney, Agent, or Firm*—Webb Ziesenheim Logsdon Orkin & Hanson, P.C.

(57) ABSTRACT

The invention provides a vaccine for the prevention and/or the treatment of infection by *Actinobacillus pleuropneumoniae*, the causative agent of porcine pleuropneumonia, which vaccine contains at least an immunogenic part of at least one cytolytic protein of *A. pleuropneumoniae* produced by recombinant DNA, and detoxified derivatives thereof. Three of such cytolytic proteins are identified and a vaccine containing these, or parts or derivatives thereof, ensures protection against all known serotypes of *A. pleuropneumoniae*. The cytolytic proteins are produced by inserting a nucleotide sequence encoding one or more of the proteins or parts thereof in a host cell, cultivating the host cell and recovering the proteins. Another vaccine contains the genetic information for one or more of the cytolytic proteins, and a passive vaccine contains antibodies against these proteins. The invention further provides monoclonal antibodies and DNA probes for use in diagnostics.

5 Claims, 18 Drawing Sheets

```
AGATTAATGAGCGATATTGTTATAAAATCATAATGTAAACCTCATTTGTAATGAATTGGTAAATTATATAAA

TAATCAAAAAACTTACTTTTTTTTATTTTTATCGGTAAGTATTTACAATCAAGTCAGACAAACGGCAATATT

GTTATAAATCTGGGGGGATGAATGAGTAAAAAAATTAATGGATTTGAGGTTTTAGGAGAGGTGGCATGGTTA
     ClyI C              METSerLysLysIleAsnGlyPheGluValLeuGlyGluValAlaTrpLeu

TGGGCAAGTTCTCCTTTACATCGAAAGTGGCCGCTTTCTTTGTTAGCAATTAATGTGCTACCTGCGATTGAG
TrpAlaSerSerProLeuHisArgLysTrpProLeuSerLeuLeuAlaIleAsnValLeuProAlaIleGlu

AGTAATCAATATGTTTTGTTAAAGCGTGACGGTTTTCCTATTGCATTTTGTAGCTGGGCAAATTTGAATTTG
SerAsnGlnTyrValLeuLeuLysArgAspGlyPheProIleAlaPheCysSerTrpAlaAsnLeuAsnLeu

GAAAATGAAATTAAATACCTTGATGATGTTGCCTCGCTAGTTGCGGATGATTGGACTTCCGGCGATCGTCGA
GluAsnGluIleLysTyrLeuAspAspValAlaSerLeuValAlaAspAspTrpThrSerGlyAspArgArg

TGGTTTATAGATTGGATAGCACCGTTCGGAGACAGTGCCGCATTATACAAACATATGCGAGATAACTTCCCG
TrpPheIleAspTrpIleAlaProPheGlyAspSerAlaAlaLeuTyrLysHisMETArgAspAsnPhePro

AATGAGCTGTTTAGGGCTATTCGAGTTGATCCGGACTCTCGAGTAGGGAAAATTTCAGAATTTCATGGAGGA
AsnGluLeuPheArgAlaIleArgValAspProAspSerArgValGlyLysIleSerGluPheHisGlyGly

AAAATTGATAAGAAACTGGCAAGTAAAATTTTTCAACAATATCACTTTGAATTAATGAGTGAGCTAAAAAAT
LysIleAspLysLysLeuAlaSerLysIlePheGlnGlnTyrHisPheGluLeuMETSerGluLeuLysAsn

AAACAAAATTTTAAATTTTCATTAGTAAATAGCTAAGGAGACAACATGGCTAACTCTCAGCTCGATAGAGTC
LysGlnAsnPheLysPheSerLeuValAsnSer    ClyI A    METAlaAsnSerGlnLeuAspArgVal

AAAGGATTGATTGATTCACTTAATCAACATACAAAAAGTGCAGCTAAATCAGGTGCCGGCGCATTAAAAAAT
LysGlyLeuIleAspSerLeuAsnGlnHisThrLysSerAlaAlaLysSerGlyAlaGlyAlaLeuLysAsn

GGTTTGGGACAGGTGAAGCAAGCAGGGCAGAAATTAATTTTATATATTCCGAAAGATTATCAAGCTAGTACC
GlyLeuGlyGlnValLysGlnAlaGlyGlnLysLeuIleLeuTyrIleProLysAspTyrGlnAlaSerThr

GGCTCAAGTCTTAATGATTTAGTGAAAGCGGCGGAGGCTTTAGGGATCGAAGTACATCGCTCGGAAAAAAAC
GlySerSerLeuAsnAspLeuValLysAlaAlaGluAlaLeuGlyIleGluValHisArgSerGluLysAsn

GGTACCGCACTAGCGAAAGAATTATTCGGTACAACGGAAAAACTATTAGGTTTCTCGGAACGAGGCATCGCA
GlyThrAlaLeuAlaLysGluLeuPheGlyThrThrGluLysLeuLeuGlyPheSerGluArgGlyIleAla

TTATTTGCACCTCAGTTTGATAAGTTACTGAATAAGAACCAAAAATTAAGTAAATCGCTCGGCGGTTCATCG
LeuPheAlaProGlnPheAspLysLeuLeuAsnLysAsnGlnLysLeuSerLysSerLeuGlyGlySerSer

GAAGCATTAGGACAACGTTTAAATAAAACGCAAACGGCACTTTCAGCCTTACAAAGTTTCTTAGGTACGGCT
GluAlaLeuGlyGlnArgLeuAsnLysThrGlnThrAlaLeuSerAlaLeuGlnSerPheLeuGlyThrAla

ATTGCGGGTATGGATCTTGATAGCCTGCTTCGTCGCCGTAGAAACGGTGAGGACGACAGTGGTTCGGAATTA
IleAlaGlyMETAspLeuAspSerLeuLeuArgArgArgArgAsnGlyGluAspValSerGlySerGluLeu

GCTAAAGCAGGTGTGGATCTAGCCGCTCAGTTAGTGGATAACATTGCAAGTGCAACGGGTACGGTGGATGCG
AlaLysAlaGlyValAspLeuAlaAlaGlnLeuValAspAsnIleAlaSerAlaThrGlyThrValAspAla

TTTGCCGAACAATTAGGTAAATTGGGCAATGCCTTATCTAACACTCGCTTAAGCGGTTTAGCAAGTAAGTTA
PheAlaGluGlnLeuGlyLysLeuGlyAsnAlaLeuSerAsnThrArgLeuSerGlyLeuAlaSerLysLeu
```

FIG. 1A

AATAACCTTCCAGATTTAAGCCTTGCAGGACCTGGGTTTGATGCCGTATCAGGTATCTTATCTGTTGTTTCG
AsnAsnLeuProAspLeuSerLeuAlaGlyProGlyPheAspAlaValSerGlyIleLeuSerValValSer

GCTTCATTCATTTTAAGTAATAAAGATGCCGATGCAGGTACAAAAGCGGCGGCAGGTATTGAAATCTCAACT
AlaSerPheIleLeuSerAsnLysAspAlaAspAlaGlyThrLysAlaAlaAlaGlyIleGluIleSerThr

AAAATCTTAGGCAATATCGGTAAAGCGGTTTCTCAATATATTATTGCGCAACGTGTGGCGGCAGGCTTATCC
LysIleLeuGlyAsnIleGlyLysAlaValSerGlnTyrIleIleAlaGlnArgValAlaAlaGlyLeuSer

ACAACTGCGGCAACCGGTGGTTTAATCGGTTCGGTCGTAGCATTAGCGATTAGCCCGCTTTCGTTCTTAATT
ThrThrAlaAlaThrGlyGlyLeuIleGlySerValValAlaLeuAlaIleSerProLeuSerPheLeuAsn

GTTGCGGATAAGTTTGAACGTGCGAAACAGCTTGAACAATATTCGGAGCGCTTTAAAAAGTTCGGTTATAAA
ValAlaAspLysPheGluArgAlaLysGlnLeuGluGlnTyrSerGluArgPheLysLysPheGlyTyrLys

GGTGATAGTTTATTAGCTTCATTCTACCGTGAAACCGGTGCGATTGAAGCGGCATTAACCACGATTAACAGT
GlyAspSerLeuLeuAlaSerPheTyrArgGluThrGlyAlaIleGluAlaAlaLeuThrThrIleAsnSer

GTGTTAAGTGCGGCTTCCGCAGGTGTTGGGGCTGCTGCAACCGGCTCATTAGTCGGTGCGCCGGTAGCAGCT
ValLeuSerAlaAlaSerAlaGlyValGlyAlaAlaAlaThrGlySerLeuValGlyAlaProValAlaAla

TTAGTTAGTGCAATCACCGGTATTATTTCAGGTATTTTAGATGCTTCTAAACAGGCAATCTTCGAACGAGTT
LeuValSerAlaIleThrGlyIleIleSerGlyIleLeuAspAlaSerLysGlnAlaIlePheGluArgVal

GCAACGAAATTAGCGAATAAGATTGACGAATGGGAGAAAAAACACGGTAAAAACTATTTTGAAAACGGTTAT
AlaThrLysLeuAlaAsnLysIleAspGluTrpGluLysLysHisGlyLysAsnTyrPheGluAsnGlyTyr

GACGCCCGCCATTCCGCATTCTTAGAAGATACCTTTGAATTGTTATCACAATACAATAAAGAGTATTCGGTA
AspAlaArgHisSerAlaPheLeuGluAspThrPheGluLeuLeuSerGlnTyrAsnLysGluTyrSerVal

GAGCGTGTCGTTGCTATTACGCAACAGCGTTGGGATGTCAATATCGGTGAACTTGCCGGCATTACTCGCAAA
GluArgValValAlaIleThrGlnGlnArgTrpAspValAsnIleGlyGluLeuAlaGlyIleThrArgLys

GGTTCTGATACGAAAAGCGGTAAAGCTTACGTTGATTTCTTTGAAGAAGGAAAACTTTTAGAGAAAGAACCG
GlySerAspThrLysSerGlyLysAlaTyrValAspPhePheGluGluGlyLysLeuLeuGluLysGluPro

GATCGTTTTGATAAAAAAGTGTTTGATCCGCTTGAAGGTAAAATCGACCTTTCTTCAATTAACAAAACCACT
AspArgPheAspLysLysValPheAspProLeuGluGlyLysIleAspLeuSerSerIleAsnLysThrThr

TTATTGAAATTTGTTACCCCGGTCTTTACCGCAGGTGAAGAGATTCGTGAGCGTAAGCAAACCGGTAAATAC
LeuLeuLysPheValThrProValPheThrAlaGlyGluGluIleArgGluArgLysGlnThrGlyLysTyr

GAATATATGACCGAATTATTCGTTAAAGGTAAAGAAAAATGGGTGGTAACCGGTGTGCAGTCACATAATGCG
GluTyrMETThrGluLeuPheValLysGlyLysGluLysTrpValValThrGlyValGlnSerHisAsnAla

ATTTATGACTATACGAATCTTATCCAATTAGCGATAGATAAAAAAGGTGAAAAACGTCAAGTGACCATTGAA
IleTyrAspTyrThrAsnLeuIleGlnLeuAlaIleAspLysLysGlyGluLysArgGlnValThrIleGlu

TCTCATTTGGGTGAGAAAAATGATCGTATATATCTTTCATCCGGTTCATCTATCGTATATGCGGGTAACGGA
SerHisLeuGlyGluLysAsnAspArgIleTyrLeuSerSerGlySerSerIleValTyrAlaGlyAsnGly

CATGATGTAGCATATTACGATAAAACCGATACAGGTTACTTAACATTTGACGGACAAAGTGCACAGAAAGCC
HisAspValAlaTyrTyrAspLysThrAspThrGlyTyrLeuThrPheAspGlyGlnSerAlaGlnLysAla

GGTGAATATATTGTCACTAAAGAACTTAAAGCTGATGTAAAAGTTTTAAAAGAAGTGGTTAAAACTCAGGAT
GlyGluTyrIleValThrLysGluLeuLysAlaAspValLysValLeuLysGluValValLysThrGlnAsp

FIG. 1B

```
ATTTCAGTTGGAAAACGCAGTGAAAAATTAGAATATCGTGATTATGAGTTAAGCCCATTCGAACTTGGGAAC
IleSerValGlyLysArgSerGluLysLeuGluTyrArgAspTyrGluLeuSerProPheGluLeuGlyAsn

GGTATCAGAGCTAAAGATGAATTACATTCTGTTGAAGAAATTATCGGTAGTAATCGTAAAGACAAATTCTTT
GlyIleArgAlaLysAspGluLeuHisSerValGluGluIleIleGlySerAsnArgLysAspLysPhePhe

GGTAGTCGCTTTACCGATATTTTCCATGGTGCGAAAGGCGATGATGAAATCTACGGTAATGACGGCCACGAT
GlySerArgPheThrAspIlePheHisGlyAlaLysGlyAspAspGluIleTyrGlyAsnAspGlyHisAsp

ATCTTATACGGAGACGACGGTAATGATGTAATCCATGGCGGTGACGGTAACGACCATCTTGTTGGTGGTAAC
IleLeuTyrGlyAspAspGlyAsnAspValIleHisGlyGlyAspGlyAsnAspHisLeuValGlyGlyAsn

GGAAACGACCGATTAATCGGCGGAAAAGGTAATAATTTCCTTAATGGCGGTGATGGTGACGATGAGTTGCAG
GlyAsnAspArgLeuIleGlyGlyLysGlyAsnAsnPheLeuAsnGlyGlyAspGlyAspAspGluLeuGln

GTCTTTGAGGGTCAATACAACGTATTATTAGGTGGTGCGGGTAATGACATTCTGTATGGCAGCGATGGTACT
ValPheGluGlyGlnTyrAsnValLeuLeuGlyGlyAlaGlyAsnAspIleLeuTyrGlySerAspGlyThr

AACTTATTTGACGGTGGTGTAGGCAATGACAAAATCTACGGTGGTTTAGGTAAGGATATTTATCGCTACAGT
AsnLeuPheAspGlyGlyValGlyAsnAspLysIleTyrGlyGlyLeuGlyLysAspIleTyrArgTyrSer

AAGGAGTACGGTCGTCATATCATTATTGAGAAAGGCGGTGATGATGATACGTTATTGTTATCGGATCTTAGT
LysGluTyrGlyArgHisIleIleIleGluLysGlyGlyAspAspAspThrLeuLeuLeuSerAspLeuSer

TTTAAAGATGTAGGATTTATCAGAATCGGTGATGATCTTCTTGTGAATAAAAGAATCGGAGGAACACTGTAT
PheLysAspValGlyPheIleArgIleGlyAspAspLeuLeuValAsnLysArgIleGlyGlyThrLeuTyr

TACCATGAAGATTACAATGGGAATGCGCTCACGATTAAAGATTGGTTCAAGGAAGGTAAAGAAGGACAAAAT
TyrHisGluAspTyrAsnGlyAsnAlaLeuThrIleLysAspTrpPheLysGluGlyLysGluGlyGlnAsn

AATAAAATTGAAAAAATCGTTGATAAAGATGGAGCTTATGTTTTAAGCCAATATCTGACTGAACTGACAGCT
AsnLysIleGluLysIleValAspLysAspGlyAlaTyrValLeuSerGlnTyrLeuThrGluLeuThrAla

CCTGGAAGAGGTATCAATTACTTTAATGGGTTAGAAGAAAAATTGTATTATGGAGAAGGATATAATGCACTT
ProGlyArgGlyIleAsnTyrPheAsnGlyLeuGluGluLysLeuTyrTyrGlyGluGlyTyrAsnAlaLeu

CCTCAACTCAGAAAAGATATTGAACAAATCATTTCATCTACGGGTGCATTTACCGGTGATCACGGAAAAGTA
ProGlnLeuArgLysAspIleGluGlnIleIleSerSerThrGlyAlaPheThrGlyAspHisGlyLysVal

TCTGTAGGCTCAGGCGGACCGTTAGTCTATAATAACTCAGCTAACAATGTAGCAATTCTTTGAGTTATTCTT
SerValGlySerGlyGlyProLeuValTyrAsnAsnSerAlaAsnAsnValAlaIleLeu---

TAGCACAAGCAGCTTAAGATAGTTATTTTTAGATGATAAATAGCAATCCTATATATATTAGGTGTGTAGGAT

TGCTATTTTATTTATGGAGGAGCAAATGGATTTTTATCGGGAAGAAGACTACGGATTATACGCACTGACGAT
ClyI B                 METAspPheTyrArgGluGluAspTyrGlyLeuTyrAlaLeuThrIle

TTTAGCCCAGTACCATAATATTGCTGTAAATCCGGAAGAACTAAAACATAAATTCGACCTTGAAGGAAAAGG
LeuAlaGlnTyrHisAsnIleAlaValAsnProGluGluLeuLysHisLysPheAspLeuGluGlyLysGly

CTTAGATCTAACCGCTTGGCTATTAGCCGCAAAATCATTAGAACTTAAAGCAAAACAAGTAAAAAAAGCGAT
LeuAspLeuThrAlaTrpLeuLeuAlaAlaLysSerLeuGluLeuLysAlaLysGlnValLysLysAlaIle

TGATCGTTTGGCGTTTATCGCACTACCGGCACTTGTATGGCGAGAAGACGGTAAACATTTTATTTTGACTAA
AspArgLeuAlaPheIleAlaLeuProAlaLeuValTrpArgGluAspGlyLysHisPheIleLeuThrLys
```

FIG. 1C

AATTGATAATGAAGCAAAAAAATATTTAATTTTTGATTTGGAAACGCATAATCCTCGCATTTTGGAACAAGC
IleAspAsnGluAlaLysLysTyrLeuIlePheAspLeuGluThrHisAsnProArgIleLeuGluGlnAla

GGAATTCGAGAGCTTATACCAAGGAAAACTGATTTTAGTTGCATCAAGAGCTTCCATCGTAGGTAAGCTGGC
GluPheGluSerLeuTyrGlnGlyLysLeuIleLeuValAlaSerArgAlaSerIleValGlyLysLeuAla

AAAGTTTGACTTCACTTGGTTTATACCGGCGGTAATTAAGTATCGTAAGATTTTTATTGAAACGTTAATTGT
LysPheAspPheThrTrpPheIleProAlaValIleLysTyrArgLysIlePheIleGluThrLeuIleVal

TTCAATTTTTTTGCAAATTTTCGCACTAATTACACCGCTTTTTTTCCAAGTCGTGATGGATAAAGTCTTGGT
SerIlePheLeuGlnIlePheAlaLeuIleThrProLeuPhePheGlnValValMETAspLysValLeuVal

ACACCGAGGTTTTTCAACCTTAAATGTGATTACGGTGGCATTAGCGATCGTCGTGCTGTTTGAAATTGTGCT
HisArgGlyPheSerThrLeuAsnValIleThrValAlaLeuAlaIleValValLeuPheGluIleValLeu

AAACGGTTTACGTACCTATATTTTTGCGCATAGTACCAGCCGTATTGATGTGGAGTTGGGAGCAAGATTATT
AsnGlyLeuArgThrTyrIlePheAlaHisSerThrSerArgIleAspValGluLeuGlyAlaArgLeuPhe

CAGACATTTATTAGCACTCCCAATCTCTTATTTTGAAAATCGTCGAGTCGGCGATACGGTGGCTCGTGTACG
ArgHisLeuLeuAlaLeuProIleSerTyrPheGluAsnArgArgValGlyAspThrValAlaArgValArg

AGAACTCGATCAAATTCGTAACTTCTTAACCGGGCAGGCACTTACTTCCGTGTTGGATTTAATGTTTTCCTT
GluLeuAspGlnIleArgAsnPheLeuThrGlyGlnAlaLeuThrSerValLeuAspLeuMETPheSerPhe

TATCTTCTTTGCAGTGATGTGGTATTACAGCCCTAAACTTACTCTTGTGATTTTAGGCTCGTTACCGTTTTA
IlePhePheAlaValMETTrpTyrTyrSerProLysLeuThrLeuValIleLeuGlySerLeuProPheTyr

TATGGGGTGGTCGATTTTTATCAGCCCTATTTTACGTCGCCGTTTAGATGAAAAATTCGCACGTGGTGCGGA
METGlyTrpSerIlePheIleSerProIleLeuArgArgArgLeuAspGluLysPheAlaArgGlyAlaAsp

CAATCAGTCATTCTTAGTGGAATCGGTGACTGCAATCAATACGATTAAAGCGTTGGCGGTTACCCCTCAAAT
AsnGlnSerPheLeuValGluSerValThrAlaIleAsnThrIleLysAlaLeuAlaValThrProGlnMET

GACTAATACCTGGGATAAGCAATTAGCCAGCTATGTATCGGCGGGATTCCGTGTAACCACATTAGCTACTAT
ThrAsnThrTrpAspLysGlnLeuAlaSerTyrValSerAlaGlyPheArgValThrThrLeuAlaThrIle

CGGACAGCAAGGTGTACAATTTATTCAAAAAGTCGTGATGGTTATTACCTTATGGCTAGGCGCACATTTAGT
GlyGlnGlnGlyValGlnPheIleGlnLysValValMETValIleThrLeuTrpLeuGlyAlaHisLeuVal

GATTTCAGGCGATTTAAGTATCGGACAATTAATCGCATTTAATATGTTATCCGGTCAAGTGATTGCACCGGT
IleSerGlyAspLeuSerIleGlyGlnLeuIleAlaPheAsnMETLeuSerGlyGlnValIleAlaProVal

GATTCGTTTAGCGCAACTTTGGCAAGATTTCCAACAAGTGGGAATTTCGGTAACGCGTTTAGGTGATGTTTT
IleArgLeuAlaGlnLeuTrpGlnAspPheGlnGlnValGlyIleSerValThrArgLeuGlyAspValLeu

AAACTCTCCGACCGAGAGCTATCAAGGAAAATTGGCGTTACCGGAAATTAAAGGCGATATTACCTTCCGTAA
AsnSerProThrGluSerTyrGlnGlyLysLeuAlaLeuProGluIleLysGlyAspIleThrPheArgAsn

TATACGCTTCCGCTACAAACCGGATGCGCCGGTGATTTTAAATGATGTGAATTTATCGATTCAGCAAGGTGA
IleArgPheArgTyrLysProAspAlaProValIleLeuAsnAspValAsnLeuSerIleGlnGlnGlyGlu

AGTGATCGGTATCGTAGGACGTTCAGGCTCAGGGAAGAGCACCTTAACGAAATTAATTCAACGTTTTTATAT
ValIleGlyIleValGlyArgSerGlySerGlyLysSerThrLeuThrLysLeuIleGlnArgPheTyrIle

TCCGGAAAACGGTCAGGTATTAATAGATGGGCATGATTTAGCATTGGCGGATCCGAACTGGCTACGTCGTCA
ProGluAsnGlyGlnValLeuIleAspGlyHisAspLeuAlaLeuAlaAspProAsnTrpLeuArgArgGln

FIG. 1D

AGTCGGGGTGGTATTACAAGATAACGTACTATTAAATCGTAGTATTCGAGATAATATTGCCTTAGCGGATCC
ValGlyValValLeuGlnAspAsnValLeuLeuAsnArgSerIleArgAspAsnIleAlaLeuAlaAspPro

GGGTATGCCAATGGAAAAAATTGTCCATGCGGCAAAATTAGCCGGCGCACATGAATTTATTTCTGAATTGCG
GlyMETProMETGluLysIleValHisAlaAlaLysLeuAlaGlyAlaHisGluPheIleSerGluLeuArg

TGAGGGATATAACACGATTGTTGGTGAGCAAGGTGCGGGGCTATCTGGCGGGCAACGCCAACGTATTGCGAT
GluGlyTyrAsnThrIleValGlyGluGlnGlyAlaGlyLeuSerGlyGlyGlnArgGlnArgIleAlaIle

TGCACGCGCTTTGGTGAATAACCCGAAAATCTTAATTTTTGATGAAGCGACCAGCGCATTAGATTATGAATC
AlaArgAlaLeuValAsnAsnProLysIleLeuIlePheAspGluAlaThrSerAlaLeuAspTyrGluSer

CGAGCATATCATCATGCGCAATATGCACCAGATTTGTAAAGGGAGAACGGTAATTATCATTGCACACCGTTT
GluHisIleIleMETArgAsnMETHisGlnIleCysLysGlyArgThrValIleIleIleAlaHisArgLeu

ATCTACGGTAAAAAATGCCGACCGTATTATTGTGATGGAAAAAGGTCAGATTGTGGAACAAGGTAAGCATAA
SerThrValLysAsnAlaAspArgIleIleValMETGluLysGlyGlnIleValGluGlnGlyLysHisLys

AGAGCTGCTTGCTGATCCAAACGGCTTATATCACTACTTACACCAATTACAATCGGAATAGGAGGACTTATG
GluLeuLeuAlaAspProAsnGlyLeuTyrHisTyrLeuHisGlnLeuGlnSerGlu ClyI D MET

AAAACATGGCTAATGGGTTTATATGAGTTTTTCCAACGCTATAAAACGGTTTGGACGGAGATCTGGAAAATT
LysThrTrpLeuMETGlyLeuTyrGluPhePheGlnArgTyrLysThrValTrpThrGluIleTrpLysIle

CGTCATCAATTGGATACGCCGGATCGAGAAAAGGATGAAAATGAATTTTTACCTGCACACTTAGAGCTGATT
ArgHisGlnLeuAspThrProAspArgGluLysAspGluAsnGluPheLeuProAlaHisLeuGluLeuIle

GAAACACCGGTGTCAAAAAAACCGAGATTGATCGCTTATTTAATTATGCTGTTCCTATTTTTGGCATTAGTT
GluThrProValSerLysLysProArgLeuIleAlaTyrLeuIleMETLeuPheLeuPheLeuAlaLeuVal

ATTTCAATTGTCAGTCACGTAGAAATTGTGGCGACCGCAACGGGTAAATTAGCGTTTAGCGACCGTAGCAAA
IleSerIleValSerHisValGluIleValAlaThrAlaThrGlyLysLeuAlaPheSerAspArgSerLys

GAAATTAAGCCGATTGAAAACGCCTTGGTTAAAGAAATCTTTGTGCAAGACGGACAATTTGTTGAGAAAGAT
GluIleLysProIleGluAsnAlaLeuValLysGluIlePheValGlnAspGlyGlnPheValGluLysAsp

CAGTTGCTGTTACACTTGACCGCATTGGGAGCCGATGCGGATCAACAAAAAACCAAAAGTTCGTTATCGCTG
GlnLeuLeuLeuHisLeuThrAlaLeuGlyAlaAspAlaAspGlnGlnLysThrLysSerSerLeuSerLeu

ACTAAATTGGAACGTTATCGTTATGAAATTTTATTAGAGGCGGTTGCGGCGGATAGGTTGCCGCTCATTGAA
ThrLysLeuGluArgTyrArgTyrGluIleLeuLeuGluAlaValAlaAlaAspArgLeuProLeuIleGlu

CTGACAAAGGATGAATTTAAACATGCTACGGAAGAAGATAAAACCAGAATTCGCTATTTGATCACCGAGCAA
LeuThrLysAspGluPheLysHisAlaThrGluGluAspLysThrArgIleArgTyrLeuIleThrGluGln

TTTGAAGCTTGGCAAAAGCAAAAGTATCAAAAAGAATTAGCTTTGCAACGTAGAGAAGCAGAAAAACAAACG
PheGluAlaTrpGlnLysGlnLysTyrGlnLysGluLeuAlaLeuGlnArgArgGluAlaGluLysGlnThr

GTTCTAGCTAATATTCGTAAATATGAGGGAATCAGTCGAGTTGAAAATGAAAGATTAAAAGATCTTAAAAAA
ValLeuAlaAsnIleArgLysTyrGluGlyIleSerArgValGluAsnGluArgLeuLysAspLeuLysLys

TTATTTAATTCGAAATCGACTTCTAAACATGATGTCTTGACTCAAGAAAATCGTCATATCGAAGCGGTAAAT
LeuPheAsnSerLysSerThrSerLysHisAspValLeuThrGlnGluAsnArgHisIleGluAlaValAsn

GAGTTGGCGGTGTATAAATCTCGGTTGAATGAAGTGGAAAGTGACTTACGTCAAGCCAAAGAGGAAATACAT
GluLeuAlaValTyrLysSerArgLeuAsnGluValGluSerAspLeuArgGlnAlaLysGluGluIleHis

FIG. 1E

```
TTAATAACTCAGTTGTTTAGAGCCGATATTCTGGAGAAGTTGAAACAAAATGTTGAAGCGGAGAAACAGCTT
LeuIleThrGlnLeuPheArgAlaAspIleLeuGluLysLeuLysGlnAsnValGluAlaGluLysGlnLeu

TCGCTCGAATTAGAAAAAAATGAGCAGCGTCAAATTGCTTCGGTGATTCGTGCGCCGGTTTCCGGTACGGTT
SerLeuGluLeuGluLysAsnGluGlnArgGlnIleAlaSerValIleArgAlaProValSerGlyThrVal

CAGCAACTTAAAACCCATACGGTAGGCGGCGTCGTGACGACTGCCGAAACCTTGATGGTAATTGCTCCGGAA
GlnGlnLeuLysThrHisThrValGlyGlyValValThrThrAlaGluThrLeuMETValIleAlaProGlu

GATGATGTTTTAGAGGTAACGGCGTTAATTCAAAATAAGGATATCGGTTTTATCGAGGTCGGTCAGGATGCG
AspAspValLeuGluValThrAlaLeuIleGlnAsnLysAspIleGlyPheIleGluValGlyGlnAspAla

GTGATTAAAGTAGAAACTTTTCCTTATACTCGTTACGGCTATTTAATGGGTAAAGTAAAAAATATCACGCTG
ValIleLysValGluThrPheProTyrThrArgTyrGlyTyrLeuMETGlyLysValLysAsnIleThrLeu

GAAGCCATCGAACATCCGCAACTCGGTCTAGTTTTTAACTCGATTATTTCTATTGATAGAAAAACTTTATCC
GluAlaIleGluHisProGlnLeuGlyLeuValPheAsnSerIleIleSerIleAspArgLysThrLeuSer

GGCAAAGACGGCAAAGAAATTGAACTTGGATCAGGTATGAGTGTGACGGCGGAAATTAAAACTGGAGAACGT
GlyLysAspGlyLysGluIleGluLeuGlySerGlyMETSerValThrAlaGluIleLysThrGlyGluArg

AGCGTTATTAGTTATTTACTCAGTCCGTTGGAAGAATCCGTTTCGGAGAGTTTAAGAGAACGCTAAAGCAGA
SerValIleSerTyrLeuLeuSerProLeuGluGluSerValSerGluSerLeuArgGluArg---

TAAAACAAGCGGCCATATTTTCTTACTTTTTTGCAAAAAACGTATGAAATATGACCGCTTGTCGTTTGTAAA

AGACTATTTATTTACAATAATTTTAGCACCGTTAGAAAATACGATCTGACGAGCTTCAAATTGAGCGGAGAG

CTGTGCTTGCGGGTTTAGAAATACGGCTTGTGCTTCTTGCGGTAAGTCTGAAACCGGTACGCAAAGGCAAGT

TCCGCCGTGGTTTGGCGTTTTAAGTTATCTTTAAAGGTAACGGGCGCATCTTGCGTGAGGATAACTTTATCA

TTGTAAACATAGTTTACCGCCCATTGAACGATACGAATATTGCGTTTGGTTTTATTTTCAATACTGTATTTA

AAGCTAACCATCGGCTGCCCTTCTTTATTTTTAGCCAATTCATAACCGAAAAAACGTAACCCGATACTGTCA

TTAAATTGTTTAAGGCGTTTTTCTTTAGCCGAAAGAGGTGCATTTTTCGTTACTGATTTATGTTCAACCGTC

GGTTGAATTTTATTGCCTTCAGCTTGAGCATTAAACGCTAAAAAGAATGATGCTACCGCCGTGCTAAGTAAT

TTAATGTGTTTCATAATTCACCTCGTAATGAGAGCTAAAAGCCGACTTGATATATTACGCTATATATTGTCA

GATTTACGGCACAGTTGCAATGACCGCATAACCGTCCGATTCGGCAATAATCTCGACTTGGCTTTCCGCCGC

AATGAAAATCGCTTCGCCTTGTTGGAGATAAATGGACTCTTCACCGAGGTCGATATAGATACTGCCTTTCAT

CACCAATAAGATACTTGCACAGTCGGCCGTAAAGTTTTCTTCGTCAAATGCGTTGAATTGCATATGTTGCAA

TGCAAAATCTTTCGCTTCAGGCGTCGGATAAAGATGAATGAAACCGTCGTTTTCTTGATAAGGCGGAATAAC

TTCGGGGTAATCGGGCGA
    (SEQ ID NO: 1)
```

FIG. 1F

CTTAACCATTACAGAACGTTGGTACAAAAAATTTTACAGGAAAATGATGGATAGTCCTTAACAAAAATTAAT

GTTTTATTTCCTATAAAACATCCGACCAGTATTATTTTTGATTAAAAAAAGAACAAACAGATCATGACAAAC

GTTTGCCTTGTTTTCCTTCACAAAAATATTATGGTTTTTTATTTAGAATAAATTATCTATATTCATTTTTTA

GGGAATGGGAGGGATGATGCTAAAAAATGATTTTAACGTATTGGGACAAATTGCTTGGTTATGGGCAAATTC
ClyII_C METLeuLysAsnAspPheAsnValLeuGlyGlnIleAlaTrpLeuTrpAlaAsnSer

TCCAATGCACCGAAATTGGTCAGTTTCACTGTTAATGAAGAATGTTATTCCTGCAATTGAAAATGACCAATA
ProMETHisArgAsnTrpSerValSerLeuLeuMETLysAsnValIleProAlaIleGluAsnAspGlnTyr

TTTGTTACTAGTTGATGATGGTTTTCCTATTGCATATTGCAGTTGGGCCAAATTAACTCTAGAGAGTGAGGC
LeuLeuLeuValAspAspGlyPheProIleAlaTyrCysSerTrpAlaLysLeuThrLeuGluSerGluAla

TCGCTATGTAAAGGACACCAATTCATTAAAAATAGATGATTGGAATGCAGGAGATCGTATATGGATCATTGA
ArgTyrValLysAspThrAsnSerLeuLysIleAspAspTrpAsnAlaGlyAspArgIleTrpIleIleAsp

TTGGATTGCCCCATTCGGGGATTCATCTCTATTGTATAAACATATGAGACAACGTTTTCCATACGATATTGG
TrpIleAlaProPheGlyAspSerSerLeuLeuTyrLysHisMETArgGlnArgPheProTyrAspIleGly

AAGGGCAATTAGAATCTATCCTAGCAAAAAAGATACTGGAAAAATCATATATTTAAAAGGAGGAAAAATAAC
ArgAlaIleArgIleTyrProSerLysLysAspThrGlyLysIleIleTyrLeuLysGlyGlyLysIleThr

AAAAAAAGTAGCTGAAAAGACATTTCTTCAGTATGAGCAAGAGTTAATAACAGCTCTACAATAATATCTTTA
LysLysValAlaGluLysThrPheLeuGlnTyrGluGlnGluLeuIleThrAlaLeuGln---

AATGATCAATTATATAAAGGAGACTCTTTTATGTCAAAAATCACTTTGTCATCATTAAAATCGTCCTTACAA
ClyII_A METSerLysIleThrLeuSerSerLeuLysSerSerLeuGln

CAAGGATTGAAAAATGGGAAAAACAAGTTAAATCAAGCAGGTACAACACTGAAGAATGGTTTAACTCAAACT
GlnGlyLeuLysAsnGlyLysAsnLysLeuAsnGlnAlaGlyThrThrLeuLysAsnGlyLeuThrGlnThr

GGTCATTCTCTACAGAATGGGGCTAAAAAATTAATCTTATATATTCCTCAAGGCTATGATTCGGGTCAAGGA
GlyHisSerLeuGlnAsnGlyAlaLysLysLeuIleLeuTyrIleProGlnGlyTyrAspSerGlyGlnGly

AATGGAGTTCAAGATTTAGTTAAAGCTGCTAATGATTTAGGTATTGAAGTATGGCGAGAAGAACGCAGCAAT
AsnGlyValGlnAspLeuValLysAlaAlaAsnAspLeuGlyIleGluValTrpArgGluGluArgSerAsn

TTGGACATTGCAAAAACTAGCTTTGATACAACTCAGAAAATTCTAGGTTTTACTGATAGAGGAATTGTATTA
LeuAspIleAlaLysThrSerPheAspThrThrGlnLysIleLeuGlyPheThrAspArgGlyIleValLeu

TTTGCACCTCAGCTAGATAATTTATTAAAGAAGAATCCTAAAATTGGCAATACATTAGGAAGTGCTTCTAGC
PheAlaProGlnLeuAspAsnLeuLeuLysLysAsnProLysIleGlyAsnThrLeuGlySerAlaSerSer

ATCTCACAAAATATAGGTAAAGCCAATACTGTATTAGGTGGTATTCAATCTATTTTAGGATCTGTTTTATCT
IleSerGlnAsnIleGlyLysAlaAsnThrValLeuGlyGlyIleGlnSerIleLeuGlySerValLeuSer

GGAGTAAATCTGAATGAATTACTTCAAAATAAAGATCCTAATCAATTAGAACTTGCAAAAGCAGGGCTAGAA
GlyValAsnLeuAsnGluLeuLeuGlnAsnLysAspProAsnGlnLeuGluLeuAlaLysAlaGlyLeuGlu

CTGACTAATGAATTAGTTGGTAATATTGCTAGCTCGGTGCAAACTGTAGATGCATTTGCAGAACAAATATCT
LeuThrAsnGluLeuValGlyAsnIleAlaSerSerValGlnThrValAspAlaPheAlaGluGlnIleSer

AAACTAGGTTCACATTTACAGAATGTGAAAGGATTAGGAGGATTGAGTAATAAATTACAAAATCTACCAGAT
LysLeuGlySerHisLeuGlnAsnValLysGlyLeuGlyGlyLeuSerAsnLysLeuGlnAsnLeuProAsp

FIG. 2A

CTAGGAAAAGCAAGTTTAGGTTTGGACATTATCTCTGGTTTACTTTCTGGAGCATCTGCAGGTCTCATTTTA
LeuGlyLysAlaSerLeuGlyLeuAspIleIleSerGlyLeuLeuSerGlyAlaSerAlaGlyLeuIleLeu

GCAGATAAAGAGGCTTCAACAGAAAAGAAAGCTGCCGCAGGTGTAGAATTTGCTAACCAAATTATAGGTAAT
AlaAspLysGluAlaSerThrGluLysLysAlaAlaAlaGlyValGluPheAlaAsnGlnIleIleGlyAsn

GTAACAAAAGCGGTCTCATCTTACATTCTTGCCCAACGAGTCGCTTCAGGTTTGTCTTCAACTGGTCCTGTC
ValThrLysAlaValSerSerTyrIleLeuAlaGlnArgValAlaSerGlyLeuSerSerThrGlyProVal

GCTGCATTAATCGCATCTACAGTTGCACTAGCTGTTAGCCCTCTTTCATTCTTAAATGTAGCTGATAAGTTT
AlaAlaLeuIleAlaSerThrValAlaLeuAlaValSerProLeuSerPheLeuAsnValAlaAspLysPhe

AAACAAGCTGATTTAATCAAATCATATTCTGAACGCTTCCAAAAATTAGGATATGATGGAGATCGTTTATTA
LysGlnAlaAspLeuIleLysSerTyrSerGluArgPheGlnLysLeuGlyTyrAspGlyAspArgLeuLeu

GCTGATTTTCACCGTGAGACAGGAACTATTGATGCTTCTGTAACAACAATTAACACTGCTTTAGCAGCTATC
AlaAspPheHisArgGluThrGlyThrIleAspAlaSerValThrThrIleAsnThrAlaLeuAlaAlaIle

TCCGGTGGAGTTGGAGCTGCAAGCGCGGGTTCTCTAGTCGGAGCTCCAGTTGCGTTACTCGTTGCTGGTGTT
SerGlyGlyValGlyAlaAlaSerAlaGlySerLeuValGlyAlaProValAlaLeuLeuValAlaGlyVal

ACGGGACTTATTACAACTATTCTAGAATATTCTAAACAAGCCATGTTTGAACATGTTGCAAATAAGGTTCAT
ThrGlyLeuIleThrThrIleLeuGluTyrSerLysGlnAlaMETPheGluHisValAlaAsnLysValHis

GACAGAATAGTTGAATGGGAGAAAAAACATAATAAAAACTATTTTGAGCAAGGTTATGATTCTCGTCATTTA
AspArgIleValGluTrpGluLysLysHisAsnLysAsnTyrPheGluGlnGlyTyrAspSerArgHisLeu

GCTGATTTACAAGACAATATGAAGTTTCTTATCAATTTAAATAAAGAACTTCAGGCTGAACGCGTAGTAGCT
AlaAspLeuGlnAspAsnMETLysPheLeuIleAsnLeuAsnLysGluLeuGlnAlaGluArgValValAla

ATTACCCAACAAAGATGGGATAACCAAATTGGAGACCTAGCGGCAATTAGCCGTAGAACGGATAAAATTTCC
IleThrGlnGlnArgTrpAspAsnGlnIleGlyAspLeuAlaAlaIleSerArgArgThrAspLysIleSer

AGTGGAAAAGCTTATGTGGATGCTTTTGAGGAGGGGCAACACCAGTCCTACGATTCATCCGTACAGCTAGAT
SerGlyLysAlaTyrValAspAlaPheGluGluGlyGlnHisGlnSerTyrAspSerSerValGlnLeuAsp

AACAAAAACGGTATTATTAATATTAGTAATACAAATAGAAAGACACAAAGTGTTTTATTCAGAACTCCATTA
AsnLysAsnGlyIleIleAsnIleSerAsnThrAsnArgLysThrGlnSerValLeuPheArgThrProLeu

CTAACTCCAGGTGAAGAGAATCGGGAACGTATTCAGGAAGGTAAAAATTCTTATATTACAAAATTACATATA
LeuThrProGlyGluGluAsnArgGluArgIleGlnGluGlyLysAsnSerTyrIleThrLysLeuHisIle

CAAAGAGTTGACAGTTGGACTGTAACAGATGGTGATGCTAGCTCAAGCGTAGATTTCACTAATGTAGTACAA
GlnArgValAspSerTrpThrValThrAspGlyAspAlaSerSerSerValAspPheThrAsnValValGln

CGAATCGCTGTGAAATTTGATGATGCAGGTAACATTATAGAATCTAAAGATACTAAAATTATCGCAAATTTA
ArgIleAlaValLysPheAspAspAlaGlyAsnIleIleGluSerLysAspThrLysIleIleAlaAsnLeu

GGTGCTGGTAACGATAATGTATTTGTTGGGTCAAGTACTACCGTTATTGATGGCGGGGACGGACATGATCGA
GlyAlaGlyAsnAspAsnValPheValGlySerSerThrThrValIleAspGlyGlyAspGlyHisAspArg

GTTCACTACAGTAGAGGAGAATATGGCGCATTAGTTATTGATGCTACAGCCGAGACAGAAAAAGGCTCATAT
ValHisTyrSerArgGlyGluTyrGlyAlaLeuValIleAspAlaThrAlaGluThrGluLysGlySerTyr

TCAGTAAAACGCTATGTCGGAGACAGTAAAGCATTACATGAAACAATTGCCACCCACCAAACAAATGTTGGT
SerValLysArgTyrValGlyAspSerLysAlaLeuHisGluThrIleAlaThrHisGlnThrAsnValGly

FIG. 2B

```
AATCGTGAAGAAAAAATTGAATATCGTCGTGAAGATGATCGTTTTCATACTGGTTATACTGTGACGGACTCA
AsnArgGluGluLysIleGluTyrArgArgGluAspAspArgPheHisThrGlyTyrThrValThrAspSer

CTCAAATCAGTTGAAGAGATCATTGGTTCACAATTTAATGATATTTTCAAAGGAAGCCAATTTGATGATGTG
LeuLysSerValGluGluIleIleGlySerGlnPheAsnAspIlePheLysGlySerGlnPheAspAspVal

TTCCATGGTGGTAATGGTGTAGACACTATTGATGGTAACGATGGTGACGATCATTTATTTGGTGGCGCAGGC
PheHisGlyGlyAsnGlyValAspThrIleAspGlyAsnAspGlyAspAspHisLeuPheGlyGlyAlaGly

GATGATGTTATCGATGGAGGAAACGGTAACAATTTCCTTGTTGGAGGAACCGGTAATGATATTATCTCGGGA
AspAspValIleAspGlyGlyAsnGlyAsnAsnPheLeuValGlyGlyThrGlyAsnAspIleIleSerGly

GGTAAAGATAATGATATTTATGTCCATAAAACAGGCGATGGAAATGATTCTATTACAGACTCTGGCGGACAA
GlyLysAspAsnAspIleTyrValHisLysThrGlyAspGlyAsnAspSerIleThrAspSerGlyGlyGln

GATAAACTGGCATTTTCGGATGTAAATCTTAAAGACCTCACCTTTAAGAAAGTAGATTCTTCTCTCGAAATC
AspLysLeuAlaPheSerAspValAsnLeuLysAspLeuThrPheLysLysValAspSerSerLeuGluIle

ATTAATCAAAAAGGAGAAAAAGTTCGTATTGGGAATTGGTTCTTAGAAGATGATTTGGCTAGCACAGTTGCT
IleAsnGlnLysGlyGluLysValArgIleGlyAsnTrpPheLeuGluAspAspLeuAlaSerThrValAla

AACTATAAAGCTACGAATGACCGAAAAATTGAGGAAATTATTGGTAAAGGAGGAGAACGTATTACATCAGAA
AsnTyrLysAlaThrAsnAspArgLysIleGluGluIleIleGlyLysGlyGlyGluArgIleThrSerGlu

CAAGTTGATAAACTGATTAAGGAGGGTAACAATCAAATCTCTGCAGAAGCATTATCCAAAGTTGTGAATGAT
GlnValAspLysLeuIleLysGluGlyAsnAsnGlnIleSerAlaGluAlaLeuSerLysValValAsnAsp

TACAATACGAGTAAAGATAGACAGAACGTATCTAATAGCTTAGCAAAATTGATTTCTTCAGTCGGGAGCTTT
TyrAsnThrSerLysAspArgGlnAsnValSerAsnSerLeuAlaLysLeuIleSerSerValGlySerPhe

ACGTCTTCCTCAGACTTTAGGAATAATTTAGGAACATATGTTCCTTCATCAATAGATGTCTCGAATAATATT
ThrSerSerSerAspPheArgAsnAsnLeuGlyThrTyrValProSerSerIleAspValSerAsnAsnIle

CAATTAGCTAGAGCCGCTTAATATTCAAATCATAGCAATCCTATGGTGTAAATTATAGGATTGTTATTTTTT
GlnLeuAlaArgAlaAla---

TAAAGGAGAAGTTATGGAACCCAATAAAAATAAGGATCTTGGTTTAGCTGTAGAAAATCAAACCTAATCTGA

CAGTTCCCGTTTAAAATTACCGTGTCTGTCAGATTAATTTGAGCTTAAATTCTTTTCTGCCCAAATCCGTTT

TCCATCAAGTAATGTTGCCATCGGTGTTCTGCCACAGCACACTTTTCCTTGATGTGTTCGATGGTGATTATA

ATACATTCATCTAAATCAGCTTGTAATGTCGCTAAATCCGTATATATTTTCTTCCTAAATGCGACTTGGTAA

AATTCTTGTAAGATAGTCTTATGAAAACGTTCACAGATACCATTCGTCTGTGGATGCTTCACTTTCGTTTTA

GTATGCTCTATGTCATTTATCGCTAAATAAAGCTCATAATCGTGATTTTCCACTTTGCCACAATATTCACTG

CCACGGTCGGTGAGAATACGCAACATCGGTAATCCTTGGGCTTCAAAGAACGGCAGTACTTTATGATTGAGC

ATATCTGCAGCGGCAATTGCGGTTTTCATTGTGTAGAGCTTTGCAAAAGCAACCTTACTATAAGTATCAACA

AATGTTTGCTGATAAATGCGTCCAACACCTTTTAAATTACCTACATAAAAGGTATCTTGTGAACCTAAATAG

CCCGGATGAGCGGTTTCAATTTCTCCACTCGATATATCATCCTCTTTCTTACGTTCTAGGGCTTGGACTTGA
```

FIG. 2C

CTTTCATTTAGAATAATGCCTTTCTCAGCCACTTCTTTCTCTAGTGCATTTAAACGCTGTTTAAAGTTAGTA

AGATTATGACGTAGCCAAATGGAACGAACACCACCGGCTGAAACAAACACACCTTGCTTGCGAAGTTCGTTA

CTCACTCGAACTTGTCCGTAAGCTGGAAAATCTAGAGCAAATTTTACAACAGCTTGCTCAATGTGCTCGTCT

ACTCGATTTTTGATATTCGGTACCCGACGAGTTTGCTTAAGTAATGCTTCAACACCGCCTTGCGCTACGGCT
(SEQ ID NO: 6)

FIG. 2D

GTAGATATTCTTTTAATATCAAACAACTATTGTTATTTGTCTGAGTGTAGATATGTAGCATTGTGTATTTCT

TTATTTACAACTCTAATCTTAATCTAAAAAGATTTCTATATTTTCTTTGTAAGAAATTTTGTTAAAATCCGA

CTAACTATATAATTAACGGTTCTTAAAGTGGATAAATAATAAAATTATGAGTTATAAAAATGTTAAAAATTT

AACAGATGATTTTACAACTTTAGGGCATATCGCTTGGTTGTGGGCTAATTCTCCGTTACATAAGGAGTGGTC

TATCTCTTTGTTTTACTAAGAATATTTTGCCAGCCATTCAACATGATCAATATATTTTACTTATGCGAGATG

AGTTCCCTGTAGCGTTTTGTAGTTGGGCAAATTTAACGTTAACTAATGAAGTGAAGTATGTACGTGATGTGA

CGTCATTGACTTTTGAAGATTGGAATTCAGGAGAACGAAAATGGTTGATCGACTGGATTGCGCCATTTGGGG

ATAACAATACGCTTTATAGATATATGCGTAAAAAATTTCCTAATGAAGTATTCCGGGCCATTCGAGTATATC

CTGGTTCTACAGAAGCGAAAATCATTCATGTTCAAGGAGGACAAATTAATAAATTTACAGCTAAAAAATTAA

TACAACAATATCAGGAAGAACTTATTCAAGTTCTTAACAATCACAAAAAAATTGTAAGAGGATAAAATATGA
ClyIII A METSer

GTACTTGGTCAAGCATGTTAGCCGACTTAAAAAAACGGGCTGAAGAAGCCAAAAGACAAGCCAAAAAAGGCT
ThrTrpSerSerMETLeuAlaAspLeuLysLysArgAlaGluGluAlaLysArgGlnAlaLysLysGlyTyr

ACGATGTAACTAAAAATGGTTTGCAATATGGGGTGAGTCAAGCAAAATTACAAGCATTAGCAGCTGGTAAAG
AspValThrLysAsnGlyLeuGlnTyrGlyValSerGlnAlaLysLeuGlnAlaLeuAlaAlaGlyLysAla

CCGTTCAAAAGTACGGTAATAAATTAGTTTTAGTTATTCCAAAAGAGTATGACGGAAGTGTTGGTAACGGTT
ValGlnLysTyrGlyAsnLysLeuValLeuValIleProLysGluTyrAspGlySerValGlyAsnGlyPhe

TCTTTGATTTAGTAAAAGCAGCTGAGGAATTAGGCATTCAAGTTAAATATGTTAACCGTAATGAATTGGAAG
PheAspLeuValLysAlaAlaGluGluLeuGlyIleGlnValLysTyrValAsnArgAsnGluLeuGluVal

TTGCCCATAAAAGTTTAGGTACCGCAGACCAATTCTTGGGTTTAACAGAACGTGGACTTACTTTATTTGCAC
AlaHisLysSerLeuGlyThrAlaAspGlnPheLeuGlyLeuThrGluArgGlyLeuThrLeuPheAlaPro

CGCAACTAGATCAGTTCTTACAAAAACATTCAAAAATTTCTAACGTAGTGGGCAGTTCTACTGGTGATGCAG
GlnLeuAspGlnPheLeuGlnLysHisSerLysIleSerAsnValValGlySerSerThrGlyAspAlaVal

TAAGTAAACTTGCTAAGAGTCAAACTATTATTTCAGGAATTCAATCTGTATTAGGTACTGTATTAGCAGGTA
SerLysLeuAlaLysSerGlnThrIleIleSerGlyIleGlnSerValLeuGlyThrValLeuAlaGlyIle

TTAATCTTAATGAAGCTATTATTAGTGGCGGTTCAGAGCTCGAATTAGCTGAAGCTGGTGTTTCTTTAGCCT
AsnLeuAsnGluAlaIleIleSerGlyGlySerGluLeuGluLeuAlaGluAlaGlyValSerLeuAlaSer

CTGAGCTGCTTAGTAATATTGCTAAAGGTACAACAACAATAGATGCTTTCACTACACAAATCCAGAACTTTG
GluLeuLeuSerAsnIleAlaLysGlyThrThrThrIleAspAlaPheThrThrGlnIleGlnAsnPheGly

GGAAATTAGTGGAAAATGCTAAAGGGTTAGGTGGTGTTGGCCGCCAATTACAGAATATTTCAGGTTCTGCAT
LysLeuValGluAsnAlaLysGlyLeuGlyGlyValGlyArgGlnLeuGlnAsnIleSerGlySerAlaLeu

TAAGCAAAACTGGATTAGGTTTGGATATTATCTCAAGCTTACTTTCAGGAGTAACTGCAAGTTTTGCTTTAG
SerLysThrGlyLeuGlyLeuAspIleIleSerSerLeuLeuSerGlyValThrAlaSerPheAlaLeuAla

CGAATAAGAATGCTTCAACAAGCACTAAAGTTGCTGCTGGCTTTGAACTCTCAAATCAAGTAATTGGTGGTA
AsnLysAsnAlaSerThrSerThrLysValAlaAlaGlyPheGluLeuSerAsnGlnValIleGlyGlyIle

FIG. 3A

TTACGAAAGCAGTATCAAGCTATATTCTTGCACAGCGTTTAGCTGCTGGTTTATCTTCGACAGGTCCTGCTG
ThrLysAlaValSerSerTyrIleLeuAlaGlnArgLeuAlaAlaGlyLeuSerSerThrGlyProAlaAla

CAGCACTAATTGCGTCTAGTATTTCTTTAGCAATCAGTCCATTGGCGTTTTTACGTGTAGCTGATAATTTTA
AlaLeuIleAlaSerSerIleSerLeuAlaIleSerProLeuAlaPheLeuArgValAlaAspAsnPheAsn

ATCGTTCTAAAGAAATTGGCGAATTTGCTGAACGTTTCAAAAAATTGGGCTATGACGGCGATAAACTACTTT
ArgSerLysGluIleGlyGluPheAlaGluArgPheLysLysLeuGlyTyrAspGlyAspLysLeuLeuSer

CAGAGTTTTATCACGAAGCTGGTACTATTGATGCCTCAATTACTACAATTAGTACAGCACTTTCTGCTATCG
GluPheTyrHisGluAlaGlyThrIleAspAlaSerIleThrThrIleSerThrAlaLeuSerAlaIleAla

CAGCTGGAACGGCCGCCGCGAGTGCAGGTGCATTAGTTGGCGCACCAATTACTTTGTTGGTTACTGGTATCA
AlaGlyThrAlaAlaAlaSerAlaGlyAlaLeuValGlyAlaProIleThrLeuLeuValThrGlyIleThr

CAGGATTAATTTCTGGTATTTTAGAGTTCTCTAAACAACCAATGTTAGATCATGTTGCATCGAAAATTGGTA
GlyLeuIleSerGlyIleLeuGluPheSerLysGlnProMETLeuAspHisValAlaSerLysIleGlyAsn

ACAAAATTGACGAATGGGAGAAAAAATACGGTAAAAATTACTTCGAGAATGGCTATGATGCTCGTCATAAAG
LysIleAspGluTrpGluLysLysTyrGlyLysAsnTyrPheGluAsnGlyTyrAspAlaArgHisLysAla

CTTTCTTAGAAGATTCATTCTCATTATTGTCTAGTTTTAATAAACAATATGAAACTGAAAGAGCTGTTTTAA
PheLeuGluAspSerPheSerLeuLeuSerSerPheAsnLysGlnTyrGluThrGluArgAlaValLeuIle

TTACACAACAACGTTGGGATGAATATATTGGCGAACTTGCGGGTATTACTGGCAAAGGTGACAAACTCTCTA
ThrGlnGlnArgTrpAspGluTyrIleGlyGluLeuAlaGlyIleThrGlyLysGlyAspLysLeuSerSer

GTGGTAAGGCGTATGTAGATTACTTTCAAGAAGGTAAATTATTAGAGAAAAAACCTGATGACTTTAGCAAAG
GlyLysAlaTyrValAspTyrPheGlnGluGlyLysLeuLeuGluLysLysProAspAspPheSerLysVal

TAGTTTTCGATCCAACTAAGGGCGAAATTGATATTTCAAATAGCCAAACGTCAACGTTGTTAAAATTTGTTA
ValPheAspProThrLysGlyGluIleAspIleSerAsnSerGlnThrSerThrLeuLeuLysPheValThr

CGCCATTATTAACACCAGGTACAGAGTCACGTGAAAGAACTCAAACAGGTAATTATGAATATATCACGAAGT
ProLeuLeuThrProGlyThrGluSerArgGluArgThrGlnThrGlyLysTyrGluTyrIleThrLysLeu

TAGTTGTAAAAGGTAAAGATAAATGGGTTGTTAATGGCGTTAAAGATAAAGGTGCCGTTTATGATTATACTA
ValValLysGlyLysAspLysTrpValValAsnGlyValLysAspLysGlyAlaValTyrAspTyrThrAsn

ATTTAATTCAACATGCTCATATTAGTTCATCAGTAGCACGTGGTGAAGAATACCGTGAAGTTCGTTTGGTAT
LeuIleGlnHisAlaHisIleSerSerSerValAlaArgGlyGluGluTyrArgGluValArgLeuValSer

CTCATCTAGGCAATGGTAATGACAAAGTGTTCTTAGTCGCGGGTTCCGCAGAAATTCACGCTGGTGAAGGTC
HisLeuGlyAsnGlyAsnAspLysValPheLeuValAlaGlySerAlaGluIleHisAlaGlyGluGlyHis

ATGATGTGGTTTATTATGATAAAACCGATACAGGTCTTTTAGTAATTGATGGAACCAAAGCGACTGAACAAG
AspValValTyrTyrAspLysThrAspThrGlyLeuLeuValIleAspGlyThrLysAlaThrGluGlnGly

GGCGTTATTCTGTTACGCGCGAATTGAGTGGTGCTACAAAAATCCTGAGAGAAGTAATAAAAAATCAAAAAT
ArgTyrSerValThrArgGluLeuSerGlyAlaThrLysIleLeuArgGluValIleLysAsnGlnLysSer

CTGCTGTTGGTAAACGTGAAGAAACCTTGGAATATCGTGATTATGAATTAACGCAATCAGGTAATAGTAACC
AlaValGlyLysArgGluGluThrLeuGluTyrArgAspTyrGluLeuThrGlnSerGlyAsnSerAsnLeu

TAAAAGCACATGATGAATTACATTCAGTAGAAGAAATTATTGGAAGTAATCAGAGAGACGAATTTAAAGGTA
LysAlaHisAspGluLeuHisSerValGluGluIleIleGlySerAsnGlnArgAspGluPheLysGlySer

FIG. 3B

GTAAATTCAGAGATATTTTCCATGGTGCCGATGGTGATGATCTATTAAATGGTAATGATGGGGATGATATTC
LysPheArgAspIlePheHisGlyAlaAspGlyAspAspLeuLeuAsnGlyAsnAspGlyAspAspIleLeu

TATACGGTGATAAAGGTAACGATGAGTTAAGAGGTGATAATGGTAACGACCAACTTTATGGTGGTGAAGGTA
TyrGlyAspLysGlyAsnAspGluLeuArgGlyAspAsnGlyAsnAspGlnLeuTyrGlyGlyGluGlyAsn

ATGACAAACTATTAGGAGGTAATGGCAATAATTACCTCAGTGGTGGTGATGGCAATGATGAGCTTCAAGTCT
AspLysLeuLeuGlyGlyAsnGlyAsnAsnTyrLeuSerGlyGlyAspGlyAsnAspGluLeuGlnValLeu

TAGGCAAATGGTTTTTAATGTGCTTCGTGGCGGTAAAGGCGATGATAAACTTTATGGTAGCTCAGGTTCTGA
GlyLysTrpPheLeuMETCysPheValAlaValLysAlaMETIleAsnPheMETValAlaGlnValLeuIle

TTTACCTTGATGGTGGAGAAGGTAATGATTATCTAGAAGGAGGCGATGGTAGCGATTTTTATGTTTACTGTT
TyrLeuAspGlyGlyGluGlyAsnAspTyrLeuGluGlyGlyAspGlySerAspPheTyrValTyrCysSer

CCACTTCAGGTAATCATACTATTTATGATCAAGGTAAATCTAGTGATTTAGATAAACTATATTTGTCTGATT
ThrSerGlyAsnHisThrIleTyrAspGlnGlyLysSerSerAspLeuAspLysLeuTyrLeuSerAspPhe

TTTCCTTCGATCGTCTTCTTGTTGAGAAAGTTGATGATAACCTTGTACTTAGAAGTAATGAAAGTAGTCATA
SerPheAspArgLeuLeuValGluLysValAspAspAsnLeuValLeuArgSerAsnGluSerSerHisAsn

ATAATGGAGTACTCACAATCAAAGACTGGTTTAAAGAAGGGAATAAATATAACCATAAAATTGAACAAATTG
AsnGlyValLeuThrIleLysAspTrpPheLysGluGlyAsnLysTyrAsnHisLysIleGluGlnIleVal

TTGATAAAAATGGTAGAAAATTGACAGCAGAGAATTTAGGAACTTATTTCAAAAATGCTCCAAAAGCTGACA
AspLysAsnGlyArgLysLeuThrAlaGluAsnLeuGlyThrTyrPheLysAsnAlaProLysAlaAspAsn

ATTTGCTTAATTATGCAACTAAAGAAGATCAGAATGAAAGCAATTTATCTTCACTTAAAACTGAATTAAGTA
LeuLeuAsnTyrAlaThrLysGluAspGlnAsnGluSerAsnLeuSerSerLeuLysThrGluLeuSerLys

AAATTATTACTAATGCAGGTAATTTTGGTGTGGCAAAACAAGGTAATACTGGAATCAATACAGCTGCCTTGA
IleIleThrAsnAlaGlyAsnPheGlyValAlaLysGlnGlyAsnThrGlyIleAsnThrAlaAlaLeuAsn

ACAATGAAGTGAATAAAATCATTTCTTCTGCTAATACCTTTGCTACTTCACAATTGGGTGGCTCAGGGATGG
AsnGluValAsnLysIleIleSerSerAlaAsnThrPheAlaThrSerGlnLeuGlyGlySerGlyMETGly

GAACATTACCATCAACGAATGTAAATTCAATGATGCTAGGTAACCTAGCTAGAGCAGCTTAATCATCTGCAT
ThrLeuProSerThrAsnValAsnSerMETMETLeuGlyAsnLeuAlaArgAlaAla---

AATCAATAGCAATCCTATGGCTATTCTAGGATTGCTATTTTATTTATGGAGTCACAAATGCCTTTTAACGAA

AAAATAGATTACGGATTACATGCATTGGTAATTCTCGCGCAATATCACAATGTTGCCGTAAACCCTGAAGAG

GTAAAACATAAATTTGATCTTGATGGCAAAGGATTGGATCTTGTTGCTTGGTTATTAGCAGCAAAATCATTA

GAATTAAAAGCCAAACGAGTAAAAAAGAGTATTGAGCGTTTACCATTTATTCATCTTCCTGCTTTAATCTGG

CGAGATGATGGTCAA
(SEQ ID NO: 9)

FIG. 3C

RECOMBINANT VACCINE FOR PREVENTION AND/OR TREATMENT OF PLEUROPNEUMONIA INFECTIONS

RELATED APPLICATIONS

This application is a continuation of U.S. application Ser. No. 08/488,706, filed Jun. 9, 1995, now U.S. Pat. No. 5,994,525,which is a divisional of U.S. application Ser. No. 08/138,609, filed Oct. 15, 1993, now abandoned, which is a continuation of U.S. application Ser. No. 07/722,971, filed Jun. 28, 1991, now abandoned.

FIELD OF THE INVENTION

The present invention is in the veterinary field. More specifically, the invention relates to the prophylaxis and therapy of pleuropneumonia in pigs.

BACKGROUND OF THE INVENTION

Pleuropneumonia is a major respiratory disease in pigs and causes severe economic losses in pig farming in many countries including the United States and Canada. The disease is caused by the bacterium *Actinobacillus pleuropneumoniae* (previously also referred to as *Haemophilus pleuropneumoniae*) and is considered to be one of the most important disorders of the bronchial tubes in pigs. Frequently, the disease is fatal. *Actinobacillus pleuropneumoniae* is known to exist in twelve infective serotypes.

Since pleuropneumonia can be induced by inoculating pigs with sterile culture supernatants of *A. pleuropneumoniae*, extracellular toxic proteins are assumed to be involved in the development of the pneumonic lesions. There is growing evidence that qualitative or quantitative differences in toxic activities exist between the twelve serotypes of *A. pleuropreumoniae*. Hemolytic and cytotoxic activities have been reviewed by T. A. Bertam, *Can. J. Vet. Res.* 54: S53–S56 (1990). Two different hemolytic activities were reported by Frey and Nicolet, *J. Clin. Microbiol.* 28: 232–236 (1990), whereas four antigenically different activities were distinguished by Kamp and Van Leengoed, *J. Clin. Microbiol.* 27: 1187–1191 (1989). Whether such activities are functions of one or more molecules is not known.

Vaccines proposed thus far for preventing infections by *Actinobacillus pleuropneumoniae* are mostly based on whole live cells, attenuated cells, lysates, culture supernatants, or extracts of *A. pleuropneumoniae*. WO-A-80,02113 (or Canadian Patent 1,189,790) teaches a vaccine for controlling pleuropneumonia in pigs, containing *A. pleuropneumoniae* cells, cell fragments etc. and, as an adjuvant, material derived from *Bordetella pertussis*. EP-A-420,743 proposes a vaccine containing inactivated toxin of serotype 1 and optionally an inactivated toxin of another serotype of *A. pleuropneumoniae*; it provides protection against serotype 1 and partial protection against other serotypes. EP-A-354,628 discloses a universal vaccine against *A. pleuropneumoniae*, which contains extracellular proteins from two different serotypes, and is effective against all *A. pleuropneumoniae* serotypes. Although these known vaccines provide protection against some or even all of the field strains of *A. pleuropneumoniae*, the active compounds are not known. As a result, control, verification, and standardisation of vaccines is difficult, since the ratio between active components cannot be optimized and inactive and sometimes adverse components are always present in the vaccines.

SUMMARY OF THE INVENTION

The present invention, in one aspect, provides a vaccine for the prevention and/or the treatment of infection by

*Actinobacillus pleuropneumoniae* containing at least an immunogenic part of at least one polypeptide selected from the group consisting of cytolytic proteins of *A. pleuropneumoniae* produced by recombinant DNA technology, and detoxified derivatives thereof.

It has been found according to the invention that *Actinobacillus pleuropneumoniae* produces three hemolytic and/or cytotoxic proteins (toxins), hereinafter referred to as cytolytic proteins: Cytolysins I, II and III (ClyI, ClyII and ClyIII). Where the term "Cytolysin" (Cly) is used in the present specification, this shall thus be understood to comprise any extracellular protein produced by any strain of *A. pleuropneumoniae* and producing any adverse effect (be it hemolytic, cytotoxic or other or both) on cells or tissues of an infected animal; where appropriate it shall be understood also to comprise immunogenically active parts of these proteins or derivatives thereof having diminished adverse effects. Protection against infections by any of the known serotypes of *A. pleuropneumoniae* is conferred to an animal by administering an effective amount of all three cytolysins, and partial or complete protection against specific serotypes is conferred by administering one or two of the cytolysins, depending on the serotype or serotypes in question.

Thus, the vaccine of the invention contains at least one of the three cytolysins I, II and III, preferably two, and more preferably three. The cytolysins may be present in the vaccine as the naturally occurring proteins, or they may be present as derivatives containing at least an immunogenic part of the proteins, or as a detoxified equivalent. Detoxification shall be understood to mean that the toxic activity of the proteins has been removed to a sufficient degree or for a sufficient number of the protein molecules to provide a vaccine which does not produce an unacceptable toxic reaction in the producing host and/or in the vaccinated animal, whereas it provides a sufficient immune response. Detoxification can be brought about by chemical, physical or enzymatic treatment of the proteins or by substitution, insertion or deletion of one or more nucleotides in the cytolysin genes resulting in the substitution, insertion or deletion of one or more amino acids in the protein. Detoxification can also be achieved by expression of the toxin gene in the absence of the activator gene.

It was found that the cytolysins are encoded by operons wherein the structural toxin gene is flanked at the 5' end by a gene encoding a peptide required to activate the toxin, hereinafter referred to as the activator protein. The cytolysins may be present in the vaccine in the activated or non-activated form.

The cytolysins or their derivatives present in the vaccine are preferably obtained by expression of recombinant DNA encoding the proteins mentioned above. The detoxified cytolysins constitute a further embodiment of the present invention.

In another aspect of the invention a process for producing a cytolytic protein of *Actinobacillus pleuropneumoniae* or an immunogenic and/or detoxified derivative thereof is provided, which process comprises the steps of:

a) selecting at least one nucleotide sequence coding for at least an immunogenic part of said cytolytic protein (toxin) optionally including an activator protein, or a derivative thereof;

b) inserting the nucleotide sequence(s) selected in step a) in a vector or an expression vector;

c) transforming a host cell, preferably a host cell that is capable of secreting said cytolytic protein, with the vector obtained in step b);

d) cultivating the host cell of step c) to express the nucleotide sequence(s) of step a), e) recovering and optionally purifying the protein from the culture;

f) optionally modifying the protein to produce a detoxified protein.

In yet another aspect, the invention is concerned with a process of producing a vaccine wherein at least one, and preferably two, and more preferably three, of the cytolysins or immunogenic parts thereof, thus produced, are combined with an immunologically acceptable carrier and optionally a suitable adjuvant.

The host cell referred to in the process of producing the cytolysins or their derivatives may be a microorganism, preferably a non-pathogenic microorganism capable of expressing at least one nucleotide sequence encoding the cytolysins by having a strong promoter inducing high expression levels or by allowing the introduction of an exogenous promoter system to induce such high expression levels. A suitable host cell is *Escherichia coli.*

In a further aspect, the invention provides a nucleotide sequence encoding at least an immunogenic part of a polypeptide selected from cytolytic proteins of *Actinobacillus pleuropneumoniae* optionally including activator proteins and transport proteins, the latter ones being proteins that assist in the secretion of the cytolytic proteins to the periplasma or the medium. The invention also relates to a system that expresses and secretes said nucleotide sequence and to a vector containing at least one of said nucleotide sequences each one preferably operatively linked to a promoter and optionally an enhancer.

In yet another aspect the invention relates to a host cell containing at least one nucleotide sequence encoding the cytolytic proteins or their derivatives, and capable of expressing them, the nucleotide sequence(s) either being contained as such or as said vector and being either present in the host cell in the genome of the host or as a plasmid. Preferably, the host cell contains nucleotide sequences encoding at least two of the cytolysins, and more preferably it contains the sequences encoding all three cytolysins. The host cell is preferably derived from *E. coli.*

The invention also provides a vaccine for prophylaxis and therapy of infections by *A. pleuropneumoniae* containing a microorganism carrying one or more nucleotide sequences encoding at least an immunogenic part of at least one cytolytic proteins of *A. pleuropneumoniae* or a detoxified derivative thereof. The microorganism may be an attenuated microorganism such as an attenuated virus or a bacterium. Administration of the vaccine results in multiplication of the microorganism and thus in production of the immunogen.

The invention further relates to diagnostic means for detecting infection by *A. pleuropneumoniae*. Specifically, the invention is concerned with an antibody, preferably a monoclonal antibody, raised against one of the native cytolysins and useful as a component of a diagnostic kit for detecting infection by *A. pleuropneumoniae*; antibodies raised against modified cytolysins are useful for determining protection by these modified cotylysins. Antibodies raised against native or modified cytolysins can also be used for passive immunisation of infected animals.

In another aspect, the invention provides a DNA-probe comprising at least a part of a nucleotide sequence encoding a cytolysin of *Actinobacillus pleuropneumoniae* which may be used in a diagnostic method and a diagnostic kit for detecting infection by *A. pleuropneumoniae*. Another method of diagnosing an *A. pleuropneumoniae* infection is to determine the presence of *A. pleuropneumoniae* cytolysins in a subject whereby protein pattern is indicative of the infective serotype or group of serotypes.

BRIEF DESCRIPTION OF THE DRAWINGS

In the appended drawings, which form a part of the present disclosure,

FIG. 1 shows the nucleotide sequence of the cytolysin I gene and its activator gene of *Actinobacillus pleuropneumoniae* serotype 9 (reference strain CVI 13261) (SEQ ID NO: 1) and the corresponding sequence of amino acid residues (SEQ ID NOS: 2–5);

FIG. 2 shows the nucleotide sequence of the cytolysin II gene and its activator and transport genes of *Actinobacillus pleuropneumoniae* strain serotype 9 (reference strain CVI 13261) (SEQ ID NO: 6), and the corresponding sequence of amino acid residues (SEQ ID NOS: 7 and 8);

FIG. 3 shows the preliminary nucleotide sequence of the cytolysin III gene of *Actinobacillus pleuropneumoniae* serotype 8 (reference strain CVI 405) (SEQ ID NO: 9), and the corresponding sequence of amino acid residues (SEQ ID NO: 10);

DETAILED DESCRIPTION OF THE INVENTION

Figure 4:
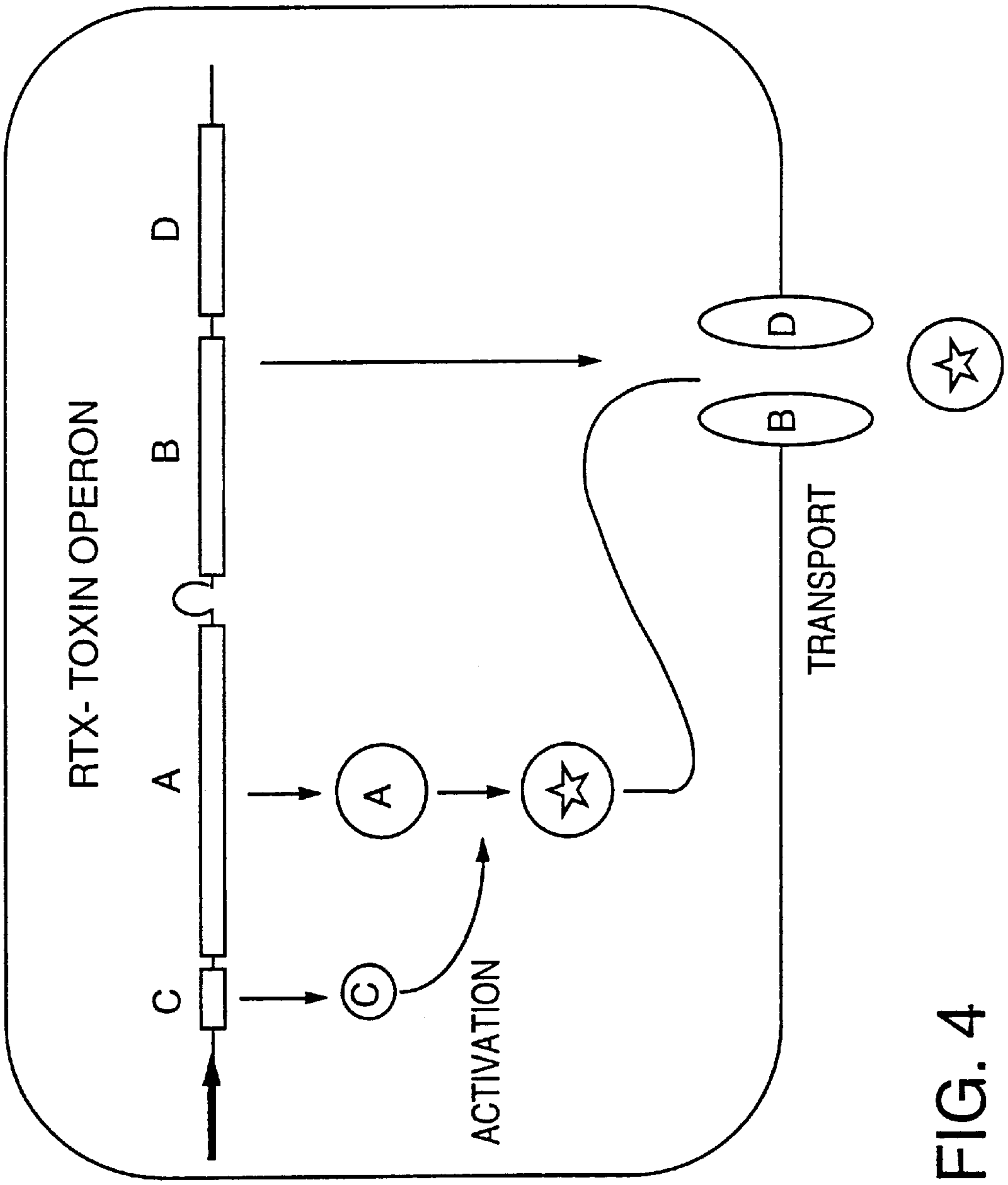
FIG. 4 schematically shows a RTX-toxin operon comprising the toxin gene (A), the activator gene (C), and the transporter genes (B, D) as well as the operation of the gene products thereof.

According to the invention it has been found that pathogenesis of *Actinobacillus pleuropneumoniae* infections can be attributed to three extracellular proteins. These proteins have approximate molecular weights of 105,000, 103,000, and 120,000 respectively. The 105,000 and 103,000 dalton proteins are immunologically related to each other. These proteins found to be excellent tools for providing protection of animals, in particular pigs, against *A. pleuropneumoniae* infections of any serotype. Although factors that were thought to be responsible for the pathogenicity of *A. pleuropneumoniae* were referred to in the prior art as hemolysins and cytotoxins, it has been found now that both cytotoxic and hemolytic activities can result from a single molecule, and hence these proteins are denoted herein as cytolysins (Cly's): the 105 kDa protein as ClyI, the 103 kDa protein as ClyII, and the 120 kDa protein as ClyIII. The nucleotide sequence of the clyI and clyII genes and the preliminary sequence of clyIII is given in FIGS. 1, 2 and 3, respectively.

In FIG. 1 the amino acid sequences of the ClyI C protein (activator), ClyI A protein (cytolytic protein ClyI), ClyI B protein (transport protein), and ClyI D protein (transport protein) are indicated below the nucleotide sequence (SEQ ID NO: 1).

In FIG. 2 the amino acid sequences of the ClyII C protein (activator) and ClyII A protein (cytolytic protein ClyII), are indicated below the nucleotide sequence (SEQ ID NO: 2).

In FIG. 3 the amino acid sequence of the ClyIII A protein (cytolytic protein ClyII) is indicated below the nucleotide sequence (SEQ ID NO: 3).

For the cloning and characterization of the genetic determinants for these proteins three different screening techniques were used: hybridization with an lkt DNA probe, selection for hemolytic activity, and reacion with monoclonal antibodies. On the basis of the reaction pattern with a set of MAbs it was concluded that ClyII is responsible for what has been described by others as HlyII activity (Frey, J., and J. Nicolet (1990) *J. Clin. Microb.* 28: 232–236). ClyI is identical to HlyI. Since we found no differences between the ClyII amino acid sequence of serotype 9 and that of an RTX toxin identified in serotype 5, the latter also must be responsible for HlyII activity and not for HlyI as has been suggested by others (Chang, Y. et al. (1989) *DNA*, 8: 635–647; MacInnes, J. I. et al. (1990) *J. Bacteriol.* 172: 4587–4592). For ClyII we now have shown, for the first time, that both a (weak) hemolytic activity as well as a (moderate) cytotoxic activity are clearly confined in a single protein.

ClyI, ClyII and ClyIII are members of the RTX cytotoxin family. This finding is not only based on immunological data but also on the similarities between primary sequences, hydropathy profiles and the secretion of active toxin by the hlyBD genes of *E. coli.* The sequenced areas of the ClyI, ClyII and ClyIII encoding operons possess all the general characteristics of other RTX toxin operons (cf. Strathdee, C. A., and R. Y. C. Lo. (1989) *J. Bacteriol.* 171: 916–928).

With respect to the genetic organization of the ClyII operon we found a striking difference with other RTX operons. The ClyII operon does not contain secretion genes contiguous to the toxin gene. Sequence alignment studies suggested that in an ancestral clyII operon a recombination event occured at position 3490 thereby disrupting the ancestral clyIIB gene. Intact secretion genes are, however, present elsewhere in the genomes of *A. pleuropneumoniae* serotypes. These secretion genes, however, belong to intact (serotypes 1, 5, 9, 10, 11) or disrupted (serotypes 2, 4. 7, 8, 12) ClyI operons. This is based on sequence data and on the observation that a 7.4 kb NsiI/HindIII DNA fragment covering the clyB gene and approximately 4.5 kb of upstream sequences of serotype 9 encodes a 105 kDa protein indistinguishable from ClyI. This means that the ancestral clyIIBD genes have been lost from the serotype 9 genome. In addition these data indicate that secretion of both ClyI and ClyII is dependent on only a single set of secretion genes. Since these secretion genes belong to the ClyI operon, these genes are referred to herein as clyIBD. Three extra nucleotides are present in front of clyIBD in a region which forms a rho-independent transcription termination signal in other RTX determinants (cf. Strathdee, C. A., and R. Y. C. Lo. (1989) *J. Bacteriol.* 171: 5955–5962). Furthermore the row of seven T residues which is present in these signals has been changed in clyI to the sequence TTTATTT. These nucleotide changes might affect the efficiency of transcription termination or the regulation of this process leading to another level of clyBD expression.

The finding that the primary amino acid sequence of the serotype 9 ClyII is completely identical to the serotype 5 hemolysin and also the finding that (almost) completely identical clyIICA genes are present in serotypes 1, 2, 3. 4, 7, 8, 11 and 12, suggests an important role for ClyII in pathogenesis. The observation that ClyII is produced in all serotypes except serotype 10 and that ClyII is the only extracellular cytolysin of serotypes 6, 7, and 12, supports this view.

The ClyII determinant of the reference strains of all twelve *A. pleuropneumoniae* serotypes were studied and it was demonstrated, by southern hybridization, that clyIICA sequences are present in all serotypes, except 10. This is in agreement with the observation that serotype 10 is the only serotype not secreting ClyII. PCR amplification of the clyIICA sequences of the serotypes carrying these genes resulted in equally sized products for all serotypes, except 6. The clyIICA genes of the serotypes 1, 2, 3, 4, 5, 7, 8, 9, 11 and 12, giving equally sized PCR fragments, were compared by extensive RFLP studies. For these studies we used four different restriction enzymes, which together have 57 recognition sites in the clyIICA sequence of serotype 9 and are therefore very suitable for a detailed comparative study. These studies showed very similar restriction patterns of clyIICA for the ten serotypes examined. These results give strong evidence that the clyIICA genes of the serotypes 1, 2, 3, 4, 5, 7, 8, 9, 11 and 12 have a very similar primary structure. Only three differences among the clyIICA genes of the 10 serotypes were found in these RFLP studies, and this low number is illustrative for the high degree of similarity between the clyII genes. Compared to the serotype 9 sequence additional sites were found for Sau3AI in serotype 5 at position −94, and for RsaI in serotype 7 close to position 2818 or 3143. Furthermore a small deletion between position 510 and 690 was found in serotype 8 by HinfII digestion. Sequence comparison of the serotype 5 and 9 clyIICA sequences showed this additional Sau3AI site in serotype 5. From this comparison it was also expected that in serotype 5 an additional HpaII site at position 209, a three basepair deletion at position 51 and a single base-pair deletion at position 44 would be present. No evidence was found either for the additional HpaII site, when analysing the clyIICA fragments of serotype 5 and 9, after digestion with this enzyme, or for the deletions when analyzing the sizes of the restriction fragments generated by AluI, HinfII, RsaI or Sau3AI. The absence of these sequence differences shows that the serotype 5 and 9 clyIICA sequences are even more similar to each other than expected from the published DNA sequences.

Intact transporter genes, clyIIBD, contiguous with the clyIICA genes were not found among the twelve serotypes. Hybridization of the proposed clyIBD sequences of serotype 9 to genomic DNA of the twelve serotypes showed hybridization to all serotypes, excluding 3 and 6. This indicates that all serotypes, but 3 and 6, do contain the clyIBD transporter genes. The translation products of these genes may act in trans and account for the transmembrane transport of ClyII. The transporter proteins for ClyII of serotypes 3 and 6 however remain to be identified. To our knowledge the proposed complementation of the RTX transporter genes of two RTX operons is the first evidence that these transporter genes are exchangeable in a naturally occurring organism.

The fact that most serotypes secrete ClyII, and that serotype 7 and 12 secrete ClyII as the only cytolysin illustrates the role of this toxin in porcine pleuropneumonia. Immunization with ClyII will induce antibodies directed against ClyII of all serotypes. Furthermore, the very similar clyIICA genes may be the targets of choice for diagnosis of *A. pleuropneumoniae* infection, since their sequences are present and highly similar in all serotypes, except serotype 10. There is good evidence that field strains of most, if not all, serotypes produce the same cytolytic activities as the reference strains.

Table A shows the extracellular protein pattern and their hemolytic and cytotoxic activity for the various serotypes of *Actinobacillus pleuropneumoniae*. Table B shows the same protein and activity pattern wherein the immunologically related serotypes are grouped together.

TABLE A

| Strain | 1 | 2 | 3 | 4 | 5 | 6 | 7 | 8 | 9 | 10 | 11 | 12 |
|---|---|---|---|---|---|---|---|---|---|---|---|---|
| 120 kDa = ClyIII | | ■ | ■ | ■ | | ■ | | ■ | | | | |
| 105 kDa = ClyI | ■ | | | | ■ | | | ■ | ■ | ■ | ■ | |
| 103 kDa = ClyII | ■ | ■ | ■ | ■ | ■ | ■ | ■ | ■ | ■ | | ■ | ■ |
| Hemolytic | S | W | W | W | S | N | W | W | S | S | S | W |
| Cytotoxic | S | S | S | S | S | N | M | S | S | S | S | M |

S = strong activity;
M = moderate activity;
W = weak activity;
N = none
■ = protein band is present

TABLE B

| Serotype | 1 | 5 | 9 | 11 | 2 | 3 | 4 | 8 | 7 | 12 | 10 |
|---|---|---|---|---|---|---|---|---|---|---|---|
| 120 kDa = ClyIII | | | | | ■ | ■ | ■ | ■ | | | |
| 105 kDa = ClyI | ■ | ■ | ■ | ■ | | | | | | | ■ |
| 103 kDa = ClyII | ■ | ■ | ■ | ■ | ■ | ■ | ■ | ■ | ■ | ■ | |
| Hemolytic | S | S | S | S | W | W | W | W | W | W | S |
| Cytotoxic | S | S | S | S | S | S | S | S | M | M | S |

S = strong activity;
M = moderate activity;
W = weak activity;
N = none
■ = protein band is present A vaccine containing ClyII or an immunogenic part thereof or a detoxified derivative thereof will provide protection against infections by *Actinobacillus pleuropneumoniae* serotypes 7 and 12, whereas it might provide partial protection against other serotypes except 10. Similarly, a vaccine containing ClyI or an effective part or derivative thereof will provide protection against serotype 10 and partial protection against serotypes 1, 5, 9 and 11, whereas a vaccine containing ClyIII or an effective part or derivative thereof will provide partial protection against serotypes 2, 3, 4, 6 and 8. Further a vaccine containing ClyII and ClyI or effective parts or derivatives thereof will provide protection against infection by serotypes 1, 5, 7, 9, 10, 11 and 12, and partial protection against the other serotypes; a vaccine containing ClyII and ClyIII or effective parts or derivatives thereof will provide protection against infection by serotypes 2, 3, 4, 6, 7, 8 and 12, and partial protection against the other serotypes except 10; a vaccine containing ClyI and ClyIII or effective parts or derivatives thereof provide protection against infection by serotypes 10, and partial protection against the other serotypes except 7 and 12. A preferred form of the vaccine contains ClyI, ClyII and ClyIII or immogenic parts or detoxified derivatives thereof, and is effective against all known and probably also against any still unknown serotype of *A. pleuropneumoniae.*

The vaccine of the invention contains the polypeptide or polypeptide derivatives in immunogenically effective amounts, for example between 0.1 and 1000 $\mu$g, more particularly between 1 and 100 pg of protein per dosage unit. An important advantage of the invention is that both the absolute and the relative amounts of the immunogens can be adjusted according to the intended use. In contrast, all prior art vaccines contain immunogenic factors in fixed ratios, since they were produced by live *A. pleuropneumoniae* cells, and separation of the factors was not contemplated and hardly possible. The optimum levels and ratios depend on the nature of the infection against which protect is required, the characteristics of the animals to be protected and other factors known to the skilled person. The vaccine may be administered in a conventional way, such as intravenously, intramuscularly, subcutaneously, intraperitoneally, intranasally or orally.

In addition to the cytolysin or part or derivative thereof, the vaccine may comprise an immunologically acceptable carrier, such as aqueous diluents, suspending aids, buffers; furthermore, excipients and adjuvants known in the art may be present. Suitable adjuvants include aluminum hydroxide, Freund's adjuvant (complete or incomplete), bacteria such as *Bordetella pertussis* or *E. coli* or bacterium derived matter, immune stimulating complex (iscom), oil, saponin, oligopeptides or other adjuvants known to those skilled in the art. The protein may also be coupled to an acceptable carrier molecule, particularly a natural or synthetic polymer such as polypeptides, polysaccharides, polystyrene, etc. The vaccine may also contain other immunogens related to other diseases in a prophylactically or therapeutically effective amount, to obtain a multivalent vaccine.

The cytolysin or part or derivative thereof may also be fused to another polypeptide; such other polypeptide may be a carrier polypeptide or, advantageously, a second and possibly a third cytolysin or part or derivative thereof. In a preferred embodiment, the vaccine contains a fused polypeptide comprising immunogenic parts of two or three cytolysins. Such a fused polypeptide may be prepared by coupling of the relevant polypeptides, or by fusing the nucleotide sequences encoding said polypeptides followed by suitable expression of the fused nucleotide sequence.

In the process of producing a cytolytic protein of *A. pleuropneumoniae* or a part or a derivative thereof, suitable for use in the vaccine as described above, in step a) a nucleotide sequence encoding a cytolysin is selected and optionally modified by insertion, substitution or deletion of nucleotides to obtain a sequence encoding an immunogenically active and/or a detoxified protein. The selection of the nucleotide sequence may be performed by screening the gene library of *A. pleuropneumoniae* using established methods, as illustrated in the examples to the present specification. The nucleotide sequence may then be cloned and isolated; alternatively, the nucleotide sequence may be synthesized. The sequence preferably comprises the sequence encoding an activator protein for the cytolysin, which may be the activator of the cytolysin itself; in the latter case for example, the nucleotide sequence may comprise the clyIICA gene.

The nucleotide sequence is then inserted in a suitable vector in step b). Such a vector may or may not comprise a promoter and optionally an enhancer. The promoter can be selcted to obtain the desired level of expression. Modification of the nucleotide sequence may be performed in the vector, instead of before insertion as explained above. Suitable vectors are art-known.

Step c) can be carried out using standard techniques (see for example: Maniatis, T. et al, (1982) Molecular Cloning, A Laboratory Manual, Cold Spring Harbor Laboratory). The host cell in which the vector containing the nucleotide sequence is transferred preferably also produces transport proteins allowing the cytolysin or part or derivative thereof to pass the host cell membrane and even be secreted into the medium, and thus to be easily harvested. The transport proteins may be derived from *A. pleuropneumoniae* or from the host cell or from another organism. The host cell is advantageously *E. coli.*

The nucleotide sequence to be used for producing the cytolysin can be derived from the sequence shown in FIGS.

1, 2 and 3, relating to the clyI, clyII, and clyIII genes respectively. The nucleotide sequence can comprise the entire gene, or part thereof encoding at least an epitope of the protein. The nucleotide sequence can be modified by deletions, substitutions or insertions, in particular those which result in a sequence encoding a detoxified derivative of the cytolysin, or those which result in a sequence which, although modified, still encodes the amino acid sequence of the cytolysin or derivative thereof.

Another advantageous type of vaccine provided by the present invention is a vaccine which does not contain the immunogenic protein or proteins as described above, but which contains a recombinant expression system such as a microorganism, carrying a nucleotide sequence encoding said immunogenic protein, for example integrated in its genome or present as an expression vector. Immunization is then induced by administration of the vaccine containing this expression system and subsequent replication and expression in the vaccinated animal. Examples of microorganisms that can be used for this purpose include bacteria such as Salmonella or *E. coli*, bacteriophages, and viruses, such as vaccinia virus, adenovirus, baculovirus, SV40 retrovirus, hepatitis B virus and pseudorabies virus; other examples are cells which have been transformed with one of these viruses or with other vectors and cells wherein these viruses replicate. These recombinant expression systems constitute an aspect of the present invention.

Monoclonal antibodies to the cytolysins or immunogenic parts or derivatives thereof may be produced in a known manner, e.g. by immunizing a suitable animal with the cytolysin or an appropriate epitope thereof, fusing the resulting cells producing the antibody to the cytolysin with myeloma cells, selecting and cloning the resulting hybridoma cells to produce the antibody. The antibodies to cytolysin I, II and III or to parts of these proteins can be used in a diagnostic method for assaying an infection with *A. pleuropneumoniae*. The antibodies may be employed in an agglutination assay wherein the antibody may be coupled to a solid particle. The antibodies may be labeled by an enzyme, a luminescent substance, a radioactive isotope, a complexing agent, or by other known means; they may be used in a sandwich assay with a second antibody, one of the two being labeled. The antibodies may be a part of a diagnostic kit, which further contains conventional components for carrying out an immunoassay.

The antibodies are also useful as a means of passive immunization of an animal against *A. pleuropneumoniae* wherein the antibody inhibits the activity of cytolysins that are introduced by infection. A vaccine to be used for this purpose comprises antibodies to one or more, preferably three different, cytolysins, optionally together with suitable carriers and adjuvants.

The nucleotide sequences illustrated in FIGS. 1, 2 and 3 or in particular suitable parts thereof are also useful as diagnostic tools. Such DNA probes can be used for determining the presence of *A. pleuropneumoniae* in biological samples of animals. The DNA probes of the invention are used according to known techniques for sampling, hybridization, possible amplification and detection. The DNA probes can be part of a diagnostic kit, which may further contain usual components, such as filters, labeling substances, diluents, amplification or detection aids, etc.

EXAMPLE 1

Gene Cloning and Identification of Cytolysins I, and II

Materials and Methods:

Bacterial strains, plasmids and cloning vectors. The reference strain CVI 13261 of *A. pleuropneumoniae* serotype 9 was used as DNA source. The gene library was made in bacteriophage lambda Gem11 (Promega) and propagated in *E. coli* LE 392 (Sambrook, J., E. F. Fritsch, and T. Maniatis. (1989). Molecular cloning. A laboratory manual. Second edition. Cold Spring Harbor Laboratory Press. Cold Spring Harbor. N.Y.). Specific DNA fragments were (sub)cloned in pKUN plasmid vectors (Konings, R. N. H., et al. (1987) *Methods Enzymol.* 153: 12–34) and transformed into *E. coli* JM101 (Sambrook, supra). Plasmid pLKT 52, containing the RTX determinant of *P. haemolytica*, was prepared by Dr. R. Lo (Strathdee, C. A., and R. Y. C. Lo. (1989) *J. Bacteriol.* 171: 916–928). Plasmid pLG575, a pACYC184 based plasmid containing the hlyB and hlyD secretion genes of *E. coli* was prepared by Dr. C. Hughes (Gygi, D., C. Hughes, et al (1990) *Mol. Microbiol.* 4: 123–128).

Construction and screening of the DNA library.

High molecular weight DNA was isolated by SDS/proteinase K lysis, phenol and phenol/chloroform extractions, and precipitation with ethanol (Sambrook, supra). With this DNA a library was constructed in lambda Gem11 according to the methods recommended by the supplier of the vector arms (Promega). Plaque lifts from this library were hybridized with appropriate restriction fragments which were labelled in advance with [$^{32}$P]dATP (Amersham) using the nick translation kit of Boehringer, Mannheim. Plaques that hybridized were visualized by exposure to X-ray film (Eastman Kodak). The library was also screened for the presence of hemolytic plaques. For that purpose plaques, grown at 37° C. on a Luria broth agarplate, were overlaid with 0.8% agarose containing 5% sheep erythrocytes, 10% Serum Plus (Hazelton) and 0.5 times Eagle's minimal essential medium (Flow laboratories, Irvin, England) in phosphate buffered saline. The plates were incubated at 37° C. for 6 to 12 hr. Selected plaques were purified to homogenicity by at least two cycles of plating and screening.

DNA manipulation and sequence analysis.

DNAs were digested to completion with restriction enzymes according to the specifications of the enzyme supplier (Pharmacia LKB, Sweden). The resulting fragments were separated by electrophoresis on 0.8% agarose gels. Desired fragments were electrophoretically eluted from gel slices and further purified by extractions with phenol and chloroform and precipitation with ethanol. Fragments were (sub)cloned in pKUN plasmid vectors (Konings, supra) by standard molecular biological techniques (Sambrook, supra). Progressive unidirectional deletions were made with the Erase-a-base system from Promega. Nucleotide sequences were determined by the dideoxy chain termination method (Sanger, F. et al (1977) *Proc. Natl. Acad. Sci. USA*. 74: 5463–5467). The sequences were analyzed using the PCGENE (Intel ligenetics Corp., Mountain View, Calif.) and Wisconsin GCG (University of Wisconsin) analysis software packages.

Gene Screen Plus nylon membranes (Du Pont NEN) were used for Southern blot analysis. The blots were hybridized with DNA probes, labelled as described above, according to the instructions of the membrane supplier. Before exposure the blots were washed a final time with 0.1×SSC, 0.1% SDS for 30 min at 65° C. for homologous probes and with 1×SSC, 0.1% SDS for 30 min at 50° C. for heterologous probes. All other DNA manipulations were done with standard molecular biological techniques (Sambrook, supra).

Immunoblotting, monoclonal antibodies (MAbs) and toxin bioassays.

Proteins present in recombinant plaques, cells or supernatants of stationary growth cultures were electrophoresed through reducing and denaturing 6% polyacrylamide gels (Laemmli, U. K. (1970) *Nature* (London) 227: 680–685). The separated proteins were stained with silver or blotted onto nitrocellulose with a semidry blotting apparatus (Biorad Laboratories Inc.). The blots were incubated according to the method of Towbin (Towbin, H., et al (1979) *Proc. Natl. Acad. Sci. USA*. 76: 4350–4354) with convalescent swine serum derived from an *A. pleuropneumoniae* serotype 9 infected pig or with MAbs specific for ClyI and/or ClyII. MAb CVI-ApCly 9.1 and 9.2 recognize ClyI, MAb CVI-ApCly 9.3 ClyII, and MAb CVI-ApCly 9.4 reacts with ClyI and ClyII (see example 3). Bound antibodies were detected with an anti mouse or anti swine immunoglobulin G-alkaline phosphatase conjugate (Zymed Laboratories Inc.) and color development with the substrates nitroblue tetrazolium (Merck) and 5-bromo-4-chloro-3-indolyl phosphate (Boehringer Mannheim).

Recombinant toxin, isolated from logarithmic growing cultures, was tested for hemolytic and cytotoxic activity as described earlier (Kamp, E. M., and L. A. M. G. van Leengoed (1989) *J. Clin. Microbiol.* 27: 1187–1191). Hemolytic and cytotoxic titers were expressed as the reciprocal of the highest dilution showing at least 50% lysis of the target cells.

Results

Gene cloning.

To determine whether *A. pleuropneumoniae* serotype 9 encoded for toxins related to the RTX cytotoxin family, a 3.7 kilobasepairs (kb) PvuI/SalI DNA fragment derived from the leukotoxin (lkt) determinant of *P. haemolytica* (Stathdee, C. A. and R. Y. C. Lo. (1987) Infect. Immun. 55: 3233–3236) and containing lktA, the 3'-end of lktC and the 5'-end of lktB (lktCAB) was hybridized to genomic DNA. Three specific DNA fragments were found to be homologous to the probe. The lktCAB probe was then used to screen a library of the *A. pleuropneumoniae* serotype 9 DNA which was prepared in the vector lambda Gem11. Forty recombinants reacted as strongly positive. To determine whether recombinants with cytolytic activity but without any detectable homology to lkt DNA existed, the library was also screened for the presence of recombinants capable of hemolysis of sheep red blood cells. Three recombinant plaques showed clear hemolytic activity. These hemolytic clones hybridized however with the lktCAB probe, indicating that they shared identical sequences with the clones that were found to be positive with the lkt probe. The hemolytic clones expressed a 103 kDa protein that was absent in non-hemolytic clones. This 103 kDa protein reacted with MAbs specific for ClyII and not with MAbs specific for ClyI (see below). These data indicated that we had cloned the ClyII gene.

To localize the ClyII gene in the 9–21 kb long inserts of the selected recombinants, we digested the DNA of 23 positive clones, including the hemolytic ones, with the restriction enzyme HindIII. The resulting fragments were electrophoresed, blotted onto nylon membranes and hybridized with the lktCAB probe. All recombinants contained a 2.4 kb fragment homologous to the probe. Several recombinants also contained a 4.4 kb fragment that hybridized. Others contained a hybridizing fragment of variable length in addition to the 2.4 kb fragment. Apparently only a part of the 4.4 kb HindIII fragment is present in the latter clones and has been ligated to one of the vector arms. These data provided a location for the ClyII gene (clyIIA).

Although the lktCAB probe used for screening contained approximately 300 bp of the lktB secretion gene, it appeared that none of the 9–21 kb inserts of the selected clones contained intact B and/or D genes. To investigate whether such sequences were present elsewhere in the genome, a 1.2 and a 0.7 kb EcoRV DNA fragment, covering both the 3' end of the lktB gene and the 5' end of the lktD gene of *P. haemolytica* (lktBD, 24), were hybridized with genomic DNA. A 4.3 kb HindIII fragment hybridized. This fragment was absent from the three hemolytic clones and all the clones that were selected with the lktCAB probe. From these data we concluded that the genome of *A. pleuropneumoniae* does contain sequences related to the RTX B and D secretion genes but that these sequences are not contiguous to the ClyII toxin gene.

In order to clone the RTX B and D related DNA, HindIII digested and size fractionated genomic DNA of strain CVI 13261 was ligated into a HindIII digested pKUN plasmid. After transformation into *E. coli* and colony hybridization with lktBD we were able to isolate a clone that contained the 4.3 kb HindIII fragment. Using this fragment we also isolated a 7.0 kb BglII/EcoRV fragment that overlapped the 4.3 kb HindIII fragment at the 5'-end, and a 4.2 kb BamHI fragment that overlapped the 4.3 kb HindIII fragment at the 3'-end. Restriction analysis and Southern hybridization provided a location for the postulated secretion genes clyBD.

Nucleotide sequence analysis.

The clyIICA locus and the clyBD locus were subjected to nucleotide sequence analysis. The established sequences and the derived amino acid sequences of the major open reading frames are shown in FIG. 2. Both loci contained two major open reading frames; these were named clyIIC, clyIIA, clyB and clyD (see also FIG. 1 and FIG. 2). The maps of restriction sites deduced from the sequences correlated well with the maps of restriction sites as determined from the cloned DNA and the genomic DNA (data not shown). Thus no detectable rearrangements had occurred during the cloning procedure. The sequences were numbered starting at −231 (clyIICA locus) and −592 (clyBD locus) to correspond to the orientation and location of the major open reading frames. In clyIICA the open reading frame from 1 to 477 (clyIIC) codes for a polypeptide of 159 amino acids (18.5 kDa) and the frame from 519 to 3386 (clyIIA) for a polypeptide of 956 amino acids (102.5 kDa). The latter protein is the ClyII toxin and, as other RTX toxins, contains glycine rich repeats near the carboxy terminus. In clyBD the frame from 1 to 2133 (clyB) codes for a polypeptide of 711 amino acids (80.2 kDa) and the frame from 2142 to 3575 (clyD) for a polypeptide of 478 amino acids (54.9 kDa).

These protein sequences were very similar to the protein sequences of the RTX determinants of *E. coli, P. haemolytica* and *A. pleuroponeumoniae* serotype 5. Their mutual hydropathy profiles (Kyte, J. and R. Doolittle (1982) *J. Mol. Biol.* 157: 105–132) were also quite similar. The ClyIIC and ClyIIA proteins were more homologous to the LktC and LktA proteins of *P. haemolytica* than to the HlyC and HlyA proteins of *E. coli* (Stathdee, C. A. and R. Y. C. Lo (1987) *Infect. Immun.* 55: 3233–3236). In addition the ClyIIA toxin was identical to the 105 kDa toxin identified by Chang et al. in serotype 5 (Chang, Y. et al (1989) DNA 8: 635–647). The ClyIIC protein differed however from its counterpart in serotype 5 at three positions; at amino acid position 5 (extra residue), between residues 41 and 47 (frameshift due to an insertion and deletion of nucleotide residues at positions 125 and 138) and around amino acid position 65 (nucleotide sequence of TGGGCC in serotype 9 and TCCCGG in serotype 5).

The sequence of clyIICA was highly homologous to that of other RTX sequences up to position 3490. This position corresponded to amino acid residue 12/13 of known RTX B secretion proteins. Instead of RTX B protein related sequences we found an open reading frame in the opposite DNA strand downstream this position. This finding confirmed that in serotype 9 no RTX-B related sequences were contiguous with the toxin gene. Probably a recombination occured at position 3490 (amino acid position 12/13 of the truncated RTX-B homolgue) in the clyII operon.

Identification and secretion of ClyII.

A 2.7 kb DNA fragment extending from the 5' end of the insert of one of the selected recombinants up to the KpnI site downstream clyIIA was ligated into pUC18 DNA. *E. coli* cells that contained this plasmid produced a 103 kDa protein. This protein reacted with a convalescent swine serum, with MAbs specific for ClyII, and not with MAbs specific for ClyI. To provide additional evidence that clyIIA encodes for the 103 kDa ClyII, we electrophoresed the proteins present in clyIICA containing *E. coli* cells and the proteins present in culture supernatants of serotype 9 alongside a mixture of both preparations. The data clearly indicated that the clyIIA encoded protein comigrates with ClyII.

To assess whether the ClyII toxin also shared functional related-ness with the enterobacterial RTX cytolysins, *E. coli* cells carrying the clyIICA genes were cotransformed with a compatible plasmid coding for the *E. coli* hlyBD secretion proteins. The intra- and extracellular proteins of these cells and also of cells that contained either one of these plasmids were assayed for the presence of ClyII. ClyII was only secreted from the cells when the secretion genes were present in trans. These data therefore demonstrated htyBD mediated export of ClyII across *E. coli* membranes and a functional relationship between ClyII and the RTX toxin family.

To study the biological activity of ClyII, culture supernatants and cell lysates of the same set of cells were tested for hemolytic and cytotoxic activity. The cytolytic activities in these supernatants and cell extracts perfectly matched with the presence of the ClyII protein among these preparations. These data also indicated that ClyII had two activities: a moderate cytotoxic activity and a weak hemolytic activity. These activities are schematically represented in Tables A and B.

Identification of ClyI.

Figure 8:
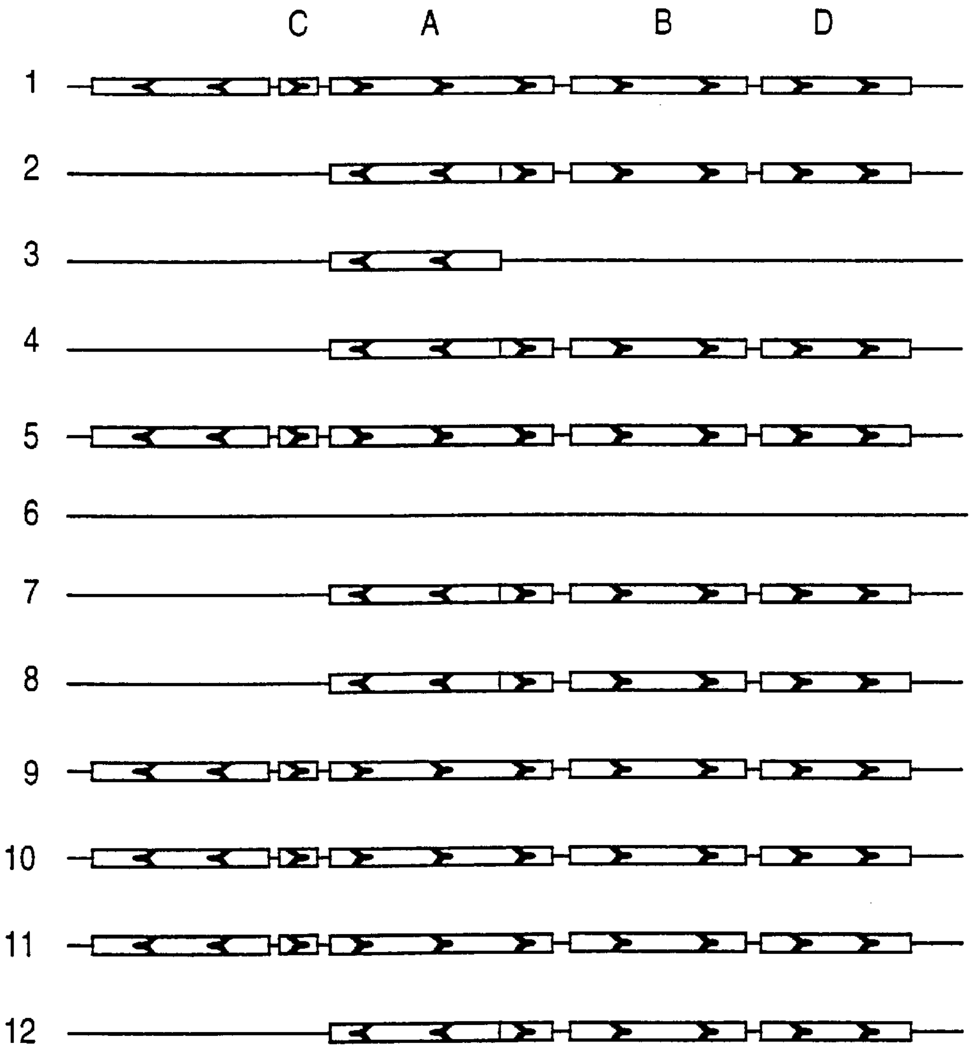
FIG. 8 shows the ClyI determinant organization of the *A. pleuropneumoniae* serotypes 1–12.

A 7.4 kb NsiI/HindIII DNA fragment containing the clyB gene and approximately 4.5 kbp of upstream sequences (FIG. 1) was ligated into pUC18 DNA. The proteins produced by cells that contained this plasmid were electrophoresed in parallel with culture supernatant of *A. pleuropneumoniae* serotype 9 and of ClyII secreting *E. coli* cells. After blotting we screened for the presence of ClyII, ClyI and ClyII+ClyI. The data demonstrated that the 7.4 kb NsiI/HindIII fragment encodes a 105 kDa protein which is indistinguishable from ClyI and which is clearly different from ClyII. This ClyI protein could also be secreted from *E. coli* cells when they contained the hlyBD secretion genes in trans. From these data we concluded that the clyBD genes form part of an RTX operon that codes for ClyI. Since the secretion genes belong to the ClyI operon, these genes are now referred to as clyIBD. The upstream sequence of clyIBD containing the clyICA genes was sequenced as described before. The sequence is shown FIG. 1. The genomic organization of the ClyI determinant was determined for the 12 serotypes of *Actinobacillus pleuropneumoniae* and is depicted in FIG. 8.

Cloning of the Gene Encoding ClyIII

Genomic DNA of *Actinobacillus pleuropneumoniae* serotype 8 was partially digested with the restriction enzyme Sau3A to fragments with an average size of about 1000 basepairs. These fragments were partially filled in using Klenow DNA polymerase and dGTP and dATP. The plasmid expression vector pUEX2 (Bressan, G. M. and K. K. Stanley (1987) *Nucl. Acid Res.* 15: 10056) was digested with the restriction enzyme SalI and partially filled in using Klenow DNA polymerase and DCTP and dTTP. The modified fragments were ligated into the linearized vector and *E. coli* strain LE392 was transformed with this ligation mixture. Approximately 90,000 independent recombinants were grown at 37° C. and after two hours of induction of the synthesis of β-galactosidase fusion proteins at 42° C., the proteins present in the recombinants were bound to nitrocellulose membranes. The membranes were screened with MAb 2.2 (see example 3), and immunoreactive clones were visualized using rabbit anti mouse serum conjugated with alkaline phosphatase. Three immunoreactive clones were found, 3.4, 5.4, and 7.4. Clones 3.4 and 7.4 contained a 400 base-pair fragment of *A. pleuropneumoniae* serotype 8, clone 5.4. contained a 1000 bp fragment. Since these fragments cross-hybridized, they contained similar DNA sequences. Sequence analysis of one of these fragments demonstrated that it did not contain the complete clyIII gene. To obtain the complete clyIII gene, genomic DNA of *A. pleuropneumoniae* serotype 8 was digested to completion with the restriction enzyme HindIII. The resulting fragments were separated on a 0.75% agarose gel and after transfer to nitrocellulose they were hybridized with the DNA fragment present in clone 7.4 which had been labeled with $^{32}P$. A 3200 bp fragment hybridized. This fragment was eluted from the gel and cloned into HindIII restricted plasmid pGEM7Z(+) (Promega) by standard molecular biological techniques. One of the resulting clones, clone 5.2, was shown to harbor the 3200 bp fragment. The nucleotide sequence of this fragment was determined and analysis of the sequence revealed an open reading frame of a distal part of a gene coding for a protein homologous to the *E. coli* α-hemolysin, and the proximal part of a gene coding for a protein homologous to Hly B of *E. coli.* It was concluded that the 3200 bp fragment of clone 5.2 comprises sequences of an RTX-toxin operon and hence that ClyIII is a member of the RTX-toxin family. Thus clone 5.2 contained the distal part of an RTX A-gene (toxin gene) and the proximal part of an RTX B-gene (coding for a transport protein). The full length sequence of the putative clyIII gene was obtained by the cloning and sequencing of a 4200 bp NsiI/XbaI fragment (clone 6.1) that hybridized with a 1200 bp HindIII/XbaI fragment of clone 5.2 and overlapped with the 5'-end of the fragment in clone 5.2. The nucleotide sequence showed the open reading frame of a gene coding for the proximal part of a RTX A protein and a complete RTX C protein.

For expression purposes we constructed a plasmid that contained an XbaI/XhoI fragment made by combining the 4200 bp NsiI/XbaI insert of clone 6.1 with a 1300 bp XbaI/XhoI fragment of clone 5.2. *E. coli* cells that contained this plasmid produced a protein with a molecular weight of about 120,000 dalton that reacted with the ClyIII specific MAb 2.2. This demonstrated that we had cloned the gene encoding ClyIII.

Cotransformation of these cells with plasmid pLG575, carrying the Hly B and D transport proteins of the *E. coli* hemolysin determinant, resulted in the secretion of the 120,000 dalton protein. The secreted protein had a strong cytotoxic activity for porcine lung macrophages. It did not show any hemolytic activity to sheep erythrocytes.

In conclusion, the 120,000 dalton protein is demonstrated to be the ClyIII protein since it has the same size, the same immunological properties, and the same biological activity as the ClyIII protein of *A. pleuropneumoniae*. Furthermore from hybridization studies we know that sequences homologous to the ClyIII coding gene are only present in the serotypes 2, 3, 4, and 8, the only serotypes that produce ClyIII.

The nucleotide sequence of the ClyIII gene was determined essentially as described above. The sequence is shown in FIG. 3.

EXAMPLE 2

Heterogeneity in the Cytolysin II Genetic Determinant of *Actinobacillus pleuropneumoniae* Serotypes Materials and methods Bacterial strains, genomic DNA, plasmids and oligonucleotides.

The reference strains for the twelve serotypes of *A. pleuropneumoniae* were used as source of genomic DNA. The reference strains for the serotypes 1 to 12 were respectively S4047, 1536, 1421, M62, K17, Femo, WF83, 405, 13261, D13039, 56153 and 8329. High molecular weight DNA was isolated by proteinase K/SDS lysis, phenol/chloroform extractions and precipitation with ethanol (Maniatis, T. et al (1982) Molecular Cloning, A Laboratory Manual, Cold Spring Harbor Laboratory). DNA fragments were cloned with the plasmid pGEM7Zf(+) (Promega Corporation, Madison, Wis.) in *E. coli* strain JM101, using standard molecular biology techniques (Maniatis, supra). Sequences of oligonucleotides used for the PCR are given. Their position in serotype 9 clyIICA is indicated between brackets. Position 1 is the first base of the clyIIC reading frame (see Example 1).

Oligo 283: CCATTACAGAACGTTGGTAC (−232 to −208) (SEQ ID NO: 6),

Oligo 284: ATTAAT<u>GCGGCCGC</u>AGGACCAG (1414 to 1435) (SEQ ID NO: 11),

Oligo 285: ACAAAA<u>GCGGCCGC</u>ATCTTACA (1356 to 1377) (SEQ ID NO: 12),

Oligo 286: CTACAGCTAAACCAAAGATCCT (3473 to 3493) (SEQ ID NO: 13),

Oligo 158: CGTAGGTGTTGCCCC (2033 to 2052) (SEQ ID NO: 14),

Oligo 322: ATTCAAT<u>AAGCTT</u>GAGCCGC (3366 to 3385) (SEQ ID NO: 15).

Underlined sequences are recognition sites for the restriction enzymes HindIII in oligonucleotide 322 and NotI in 284 and 285. These sites were introduced for cloning purposes (NotI was not used in this study) by the modification of one (322), two (285) or three (284) bases of the original serotype 9 clyIICA sequence.

Southern blots and dot-blots.

Southern blots of restriction fragments of genomic DNA, separated on 0.8% agarose gel and dot-blots of high molecular weight genomic DNA were made with Genescreen plus membranes (NEN Research Products, Boston, Mass.). For the Southern blots 1 μg of DNA per lane was used, and for the dotblots 50 ng per dot. The blots were hybridized overnight in a Hybaid hybridization oven at 65° C. DNA with a$^{32}$P dCTP (Amersham, UK) labeled DNA prepared by random prime labeling (Random Primed DNA labeling kit, Boehringer Mannheim, Mannheim, FRG). The blots were washed with a final stringency of 0.2 SSC (1×SSC is 0.15 M sodium chloride, 0.015 M sodium citrate) and 1% Sodium Dodecyl Sulphate (SDS) for 15 min at 65° C. Radioactivity was detected by autoradiography using intensifying screens on X-omat AR film (Eastman Kodak, Rochester, N.Y.).

Amplification and radiolabeling of DNA by the PCR.

The clyIICA sequences were amplified by the PCR using genomic DNA from the *A. pleuropneumoniae* reference strains as a template. The PCR was done in a volume of 50 ml containing approximately 100 ng template DNA, 1 μM of each of two specific oligonucleotides, 1 U Taq DNA polymerase (Perkin Elmer Cetus, Norwalk, Conn.), 0.2 mM of each of four deoxynucleotide triphosphates (dNTP), 25 mM Tris/HCl, pH 8.7, 2.5 mM $MgCl_2$ and 0.05% gelatin. The reaction mixture was covered with a drop of mineral oil to prevent evaporation and subjected to 30 PCR cycles of 1 min at 92° C., 1 min at 55° C. and 3 min at 74° C. in a Thermal Cycler (Perkin Elmer Cetus). Amplified DNA fragments were separated by agarose gel electrophoresis and extracted from the gel with GeneClean (Bio 101 LaJolla, Calif.). Two to four nanogrammes of the purified DNA fragments were radiolabeled in a successive PCR with a dNTP concentration of 0.05 mM each, and 5 mCi a$^{32}$P dCTP. Unincorporated dNTPs were removed by precipitating the radiolabeled DNA from the phenol/chloroform extracted reaction mixture with ethanol in the presence of 2.5 M ammonium acetate. The relatively high concentration of unlabeled dNTPs used in this PCR will decrease the specific activity of the synthesized DNA, but will favor the fidelity and complete extension of the PCR products, desirable for RFLP studies (Jansen, R. and F. D. Ledley (1989) *Gene Anal. Techn.* 6: 79–83).

Inverse PCR, cloning and sequence analysis.

Inverse PCR (Ochman, H. et al (1988) *Genetics* 120: 621–625) was done under the same conditions as the PCR described above, except that the extension reaction was 90 sec at 74° C. The templete DNA for the inverse PCR was prepared as follows: HindIII digested genomic DNA was size fractionated by agarose gel electrophoresis and extracted from the gel with GeneClean. These fragments were circularized by self-ligation with T4 ligase in a volume of 50 μl containing approximately 100 ng of DNA fragments. One tenth of the ligation product was used as a template in the inverse PCR. The inverse PCR resulted in a high background of a specific products. The desired amplification products were size fractionated by agarose gel electrophoresis and extracted from the gel with GeneClean. Reamplification of these fragments was done in a subsequent PCR using the same oligonucleotides and reaction conditions. The resulting fragments were cloned into pGEM7Zf(+), using the HindIII site resulting from the circularization reaction and an artificial HindIII site in oligonucleotide 322. Sequence analysis of the cloned fragments was done with the T7 sequencing kit (Pharmacia, Uppsala, Sweden) by using oligonucleotides specific for the SP6 and T7 promotors (Promega).

Restriction fragment analysis.

Radiolabeled DNA fragments were separately digested with the restriction enzymes AluI, Sau3AI, RsaI and HinfII. The resulting DNA fragments were separated on a vertical 5% polyacrylamide (acryl:bisacryl is 19:1) gel with dimensions of 400×500×1.5 mm, buffered with 0.18 M Tris/boric acid (pH 7.8), 0.5 mM EDTA (TBE). The digestion products were visualized by autoradiography of the dried gel.

RESULTS

Figure 5:
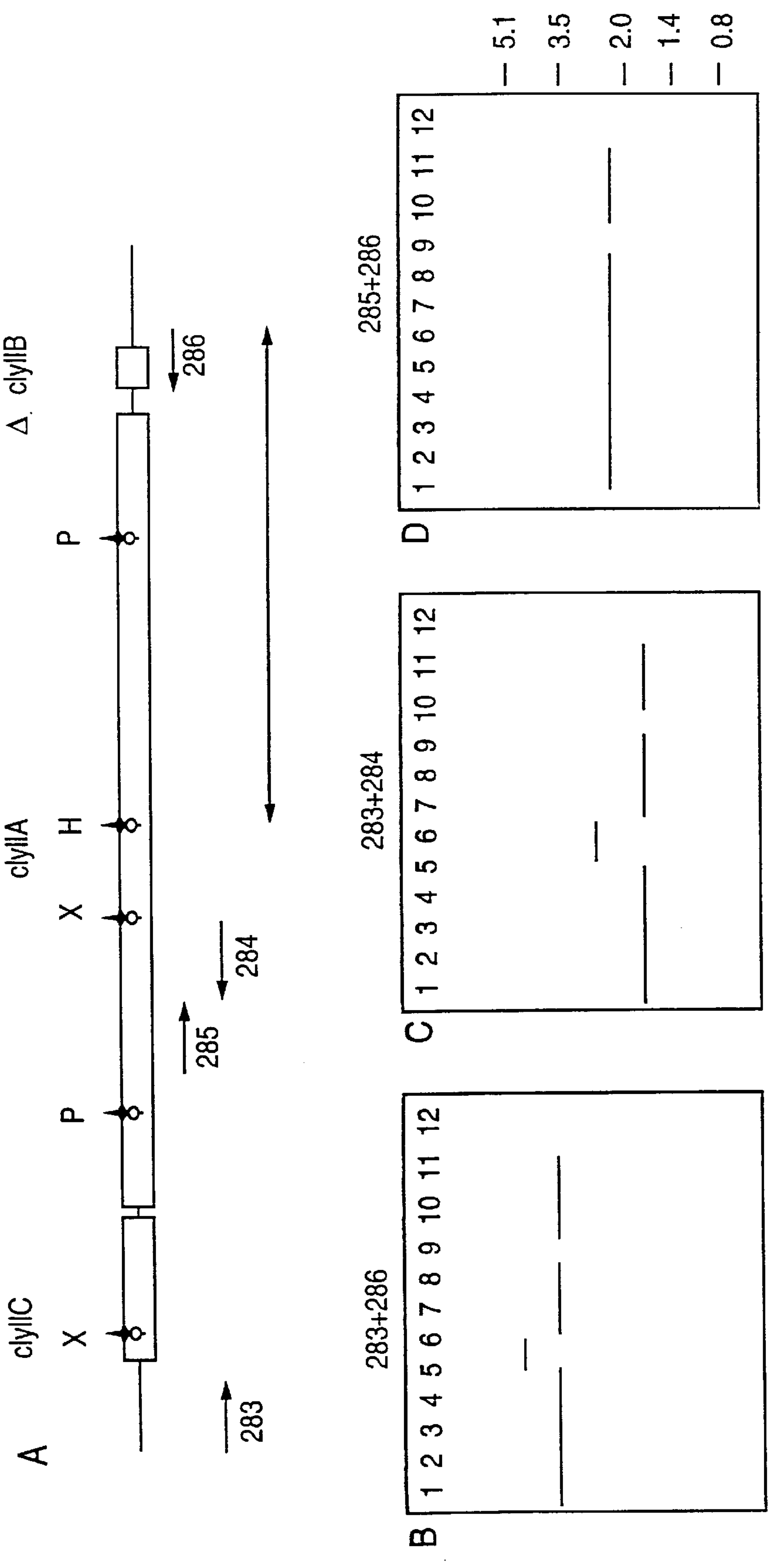
FIGS. 5A and 5B shows the clyIICA determinant of *A. pleuropneumoniae* serotype 9 and PCR amplification products.

Presence of clyIICA in the serotypes 1–12 and comparison of their sequences. The presence of clyIICA sequences in the genomic DNA of the twelve *A. pleuropneumoniae* serotypes was detected by using dot-blot hybridization with serotype 9 clyIICA sequences as a probe. This probe, comprising bases 315 to 3233, hybridized to the DNA of all serotypes, except serotype 10. Genomic DNA of the twelve serotypes was subjected to PCR using four oligonucleotides derived from the serotype 9 clyIICA genes. FIG. 5A shows the position of these oligomers in the two contiguous genes. Set 283/284 was used for amplification of the 5' region, 285/286 for the 3' region and 283/286 for-amplification of full length clyIICA. The PCR on the DNA of the serotypes 1, 2, 3, 4, 5, 7, 8, 11 and 12 resulted for each primer set in amplification products of the same size as obtained with serotype 9 DNA (1750 bp for set 283/284, 2050 bp for set 285/286 and 3200 bp for the set 283/286). The 3.2 kb full length fragments of the serotypes 1, 2, 3, 4, 5, 7, 8, 11 and 12, generated by using set 283/286, showed identical restriction maps for the enzymes HindIII, Xba I and Pst I as serotype 9 clyIICA. Serotype 6 gave an identically sized amplification product as serotype 9 for set 285/286, but amplification products which were approximately 1800 bp longer for the sets 283/284 and 283/286. Serotype 10 did not give visible amplification products using either set of oligonucleotides.

The degree of similarity between the clyIICA genes of the serotypes 1, 2, 3, 4, 5, 7, 8, 9, 11, and 12 was studied by RFLP analysis of the full length clyIICA sequences, generated in the PCR with the oligonucleotide set 283/286. The DNA fragments were labeled with $a^{32}P$ dCTP and digested with the restriction enzymes AluI, HinfII, RsaI or Sau3AI. The obtained restriction fragments were analyzed by gel electrophoresis and autoradiography. For each of the four restriction enzymes, the number and sizes of the DNA fragments obtained from clyIICA of the serotypes 1, 2, 3, 4, 5, 7, 8, 9, 11, and 12 appeared to be very similar. The RFLP studies on the serotype 12 clyIICA sequences were done in separate experiments.

Cloning and analysis of the sequences adjacent to clyIIA.

Figure 6:
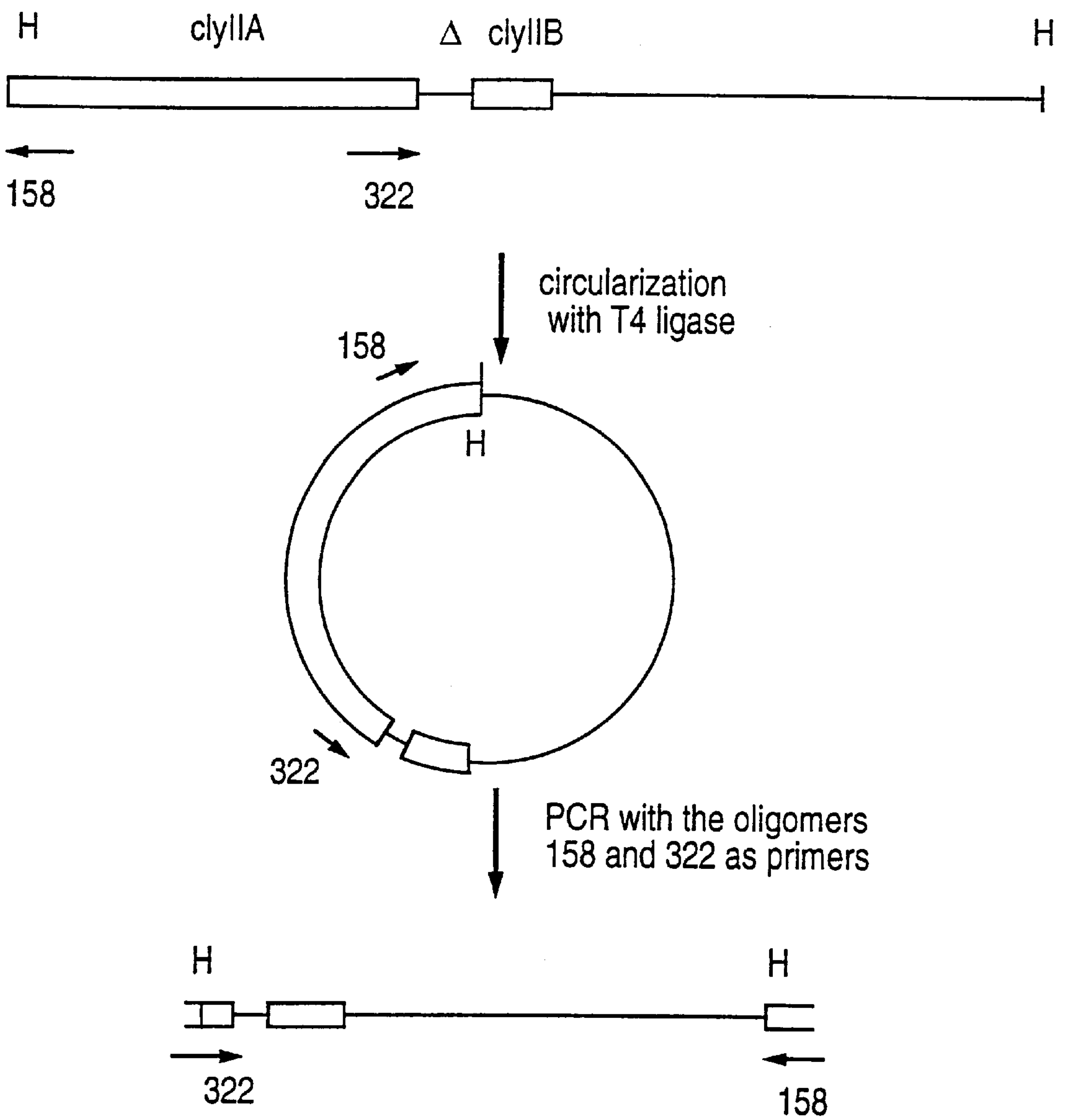
FIG. 6 schematically shows the amplification and cloning of the clyIICA 3' flanking sequence by inverse PCR.
Figure 7:
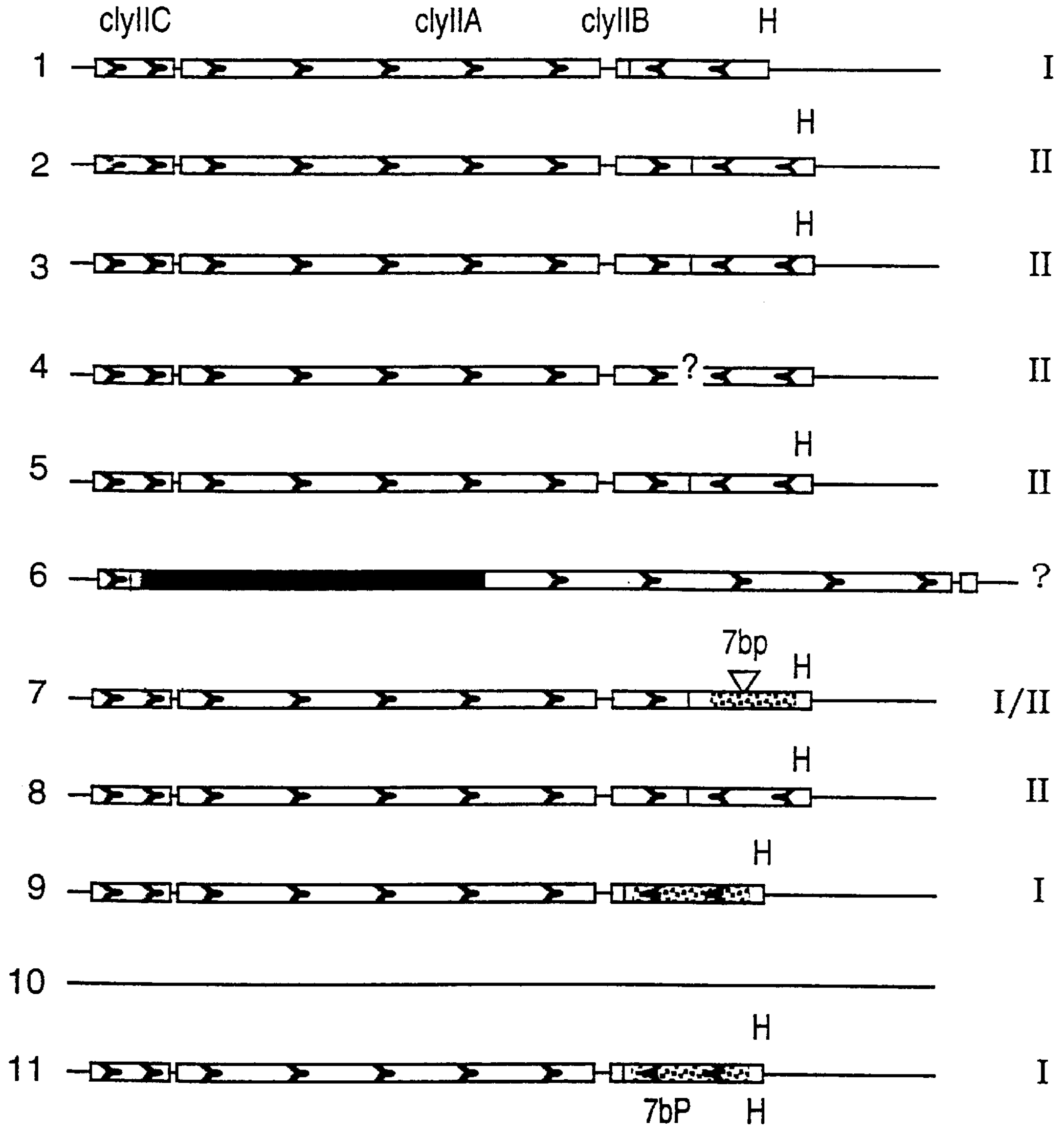
FIG. 7 shows the ClyII determinant organization of the *A. pleuropneumoniae* serotypes 1–12.

The proximal part of a putative clyIIB gene was found adjacent to clyIIA of serotype 5 and 9 (see example 1). In serotype 5 this sequence extended to at least 108 bases, but in serotype 9 it was truncated after 37 bases. To study the presence of this putative clyIIB gene in the other serotypes we cloned the sequences distal of clyIIA 3' by inverse PCR as outlined in FIG. 6. We chose HindIII digestion of the genomic DNA, since the genomic HindIII fragments of most serotypes containing these sequences have a workable size for inverse PCR amplification, and an unique HindIII site is present in clyIICA of all serotypes at base 2008. The probe used in this analysis comprised bases 2008 to 3493 of serotype 9 clyIICA. Among the twelve serotypes, four differently sized HindIII fragments hybridized to this probe. A 2.8 kb HindIII fragment in the serotypes 2, 3, 5, 7, and 8, a 2.3 kb fragment in the serotypes 1, 9, 11, and 12, a 10 kb fragment in serotype 4 and a 4.3 kb fragment in serotype 6. Inverse PCR using these HindIII fragments is expected to result in amplification products, approximately 1300 bases smaller (the number of bases between the oligonucleotides 158 and 322) than the hybridizing HindIII fragments. The inverse PCR resulted in the desired amplification products for all serotypes, except 4 and 6. The failure to get amplification products for serotypes 4 and 6 was probably due to the large sizes of the HindIII fragments, exceding the range of inverse PCR amplification in this system. We cloned the inverse PCR products of the serotypes 1, 2, 3, 5, 7, 8, 9, 11, and 12 into pGEM7Zf(+) and determined their nucleotide sequences. All these serotypes appeared to have a truncated clyIIB adjacent of clyIIA, and two different truncation points were identified, at base 37 and at base 501. We identified two major types of sequences downstream of clyIIB. Type I, present in the serotypes 1, 7, 9, 11, and 12, and type II present in the serotypes 2, 3, 5, and 8. A subtype of type I was identified in serotype 7 and 12, since both had seven additional bases, AACCACT, at position 3664. The sequence of type I was illustrated in example 1 as part (base 3490 to 4499) of the serotype 9 clyIICA sequence. The protein sequence derived from the 501 bases truncated clyIIB has a similarity of 71% to the serotype 9 clyIB (14), and 64% to the *P. haemolytica* lktB. The type I and II sequences did not show any similarity with each other or with RTX-CABD sequences. FIG. 7 shows a schematic presentation of the genomic structure of the clyIICA and the truncated clyIIB genes of the twelve serotypes. The type I sequences are represented by hatched boxes and type II sequences by dotted boxes. None of the twelve serotypes contained a clyII operon with intact genes for the B and D transporter proteins (see also example 1). Hybridization experiments demonstrated however the presence of clyIBD sequences in all serotypes except 3.

EXAMPLE 3

Identification of Hemolytic and Cytotoxic Proteins of *Actinobacillus pleuropneumoniae* by Monoclonal Antibodies Materials and Methods Bacterial strains. The sources and designations of the reference strains for *A. pleuropneumoniae* serotypes 1 to 12 were those mentioned in example 2. The field strain CVI 12946 was isolated in the Netherlands from the lung of a pig that died from pleuropneumonia. This strain was typed as serotype 2 by slide agglutination (Kamp, E. M. et al (1987) *Vet. Microbiol.* 13: 249–257).

Preparation of culture filtrates. *Actinobacillus pleuropneumoniae* strains were cultured in Eagle minimal essential medium plus Earle salts (Flow Laboratories, Irving, UK) and 10% Serum Plus (Hazelton Research Products, Lexena, Kan.) as described earlier (Kamp E. M. and A. M. G. van Leengoed (1989) *J. Clin. Microbiol.* 27 1187–1191). Cultures were centrifuged for 30 min at 10,000×g, and the supernatants were sterilized by passing them through membrane filters of 0.2 μm pore size (Gelman Sciences Inc., Ann Arbor, Mich.). Culture filtrates were stored in aliquots at −20° C. until further use.

Swine sera. Specific-pathogen-free 4-week-old pigs were endobronchially inoculated with 103 colony forming units of *A. pleuropneumoniae* 1536 (serotype 2) or 13261 (serotype 9). Blood samples were collected 2 months after inoculation. Blood was allowed to clot overnight at 4° C., serum was collected and heated for 60 min at 60° C. to inactivate complement. Sera were stored in aliquots at −20° C.

Monoclonal antibodies. Culture filtrates of strains CVI 12946 (serotype 2) and CVI 13261 (serotype 9) were detoxified with 0.5% formalin and used to immunize Balb/c mice. The immunization schedule and the preparation of hybridoma cell lines were as described in detail by van Zijderveld et al. (*Infect. Immun.* 57: 1192–1199). Hybridomas were tested for antibody in enzyme-linked immunosorbent assays (ELISA) using microtiter plates coated with culture medium or culture filtrates of strains CVI 12946 or CVI 13261. Hybridomas that tested positive with a culture filtrate and negative with the culture medium were cloned twice by limiting dilution. The resulting monoclonal cell lines were used to produce ascites fluid in pristane-primed Balb/c mice. Antibody was purified from the ascites fluid by precipitation with 40% ammonium sulfate and dialysis against phosphate-buffered saline, pH 7.2 (PBS). The MAbs were stored in aliquots containing 8 mg protein/ml at −20° C. The immunoglobulin isotype of the MAbs was determined in immuno- diffusion tests using mouse isotype-specific antisera (Nordic, Tilburg, The Netherlands).

ELISAs. The procedures for ELISA were as described in detail by Van Zijderveld et al. (supra). We used polystyrene microdilution plates coated with culture filtrates of either strain CVI 12946 or CVI 13261. The optimal dilutions for coating were determined by checkerboard titrations using the swine sera as positive sera. Coated plates were stored at −20° C.

Titers of the MAb preparations were determined in an indirect ELISA. Bound antibodies were detected with peroxidase labeled anti-mouse immunoglobulins (Dakopatts, Copenhagen, Denmark) and hydrogen peroxide mixed with 5-aminosalicylic acid. Titers were expressed as the logarithm of the reciprocal of the highest dilution giving an $A_{450}$ of 50% of the maximum obtainable absorbance value.

A competition ELISA was used to determine whether the MAbs recognized different epitopes. MAbs were conjugated to horseradish peroxidase (Boehringer, Mannheim, Federal Republic of Germany). Serial two-fold dilutions of 50 ml samples of non-conjugated MAbs were incubated in coated microdilution plates for 30 min at 37° C. Plates were not washed, and 50 ml of the optimal dilution of each of the peroxidase-conjugated MAbs was added per well. Plates were further incubated for 1 h, washed, and then incubated with the substrate.

Hemolysin assay. Serial five-fold dilutions of 1 ml of the culture filtrates were tested for hemolytic activity as described by Frey and Nicolet (1988, *FEMS Microbiol. Lett.* 55: 41–46); a suspension of 1% sheep erythrocytes in Tris-buffered saline, pH 7.2, with 10 mM CaCl2 was used.

Just before the determination of the $A_{540,\ 20}$ μl 0.1 N HCl was added to each tube to change the color of the phenol red in the medium to yellow. Hemolytic activities were expressed in hemolytic units; one hemolytic unit was defined as the absorbance value of a solution of 1 part of the 1% erythrocytes suspension and 3 parts distilled water.

Hemolysin inhibition assays. Inhibition of hemolytic activity was tested in two assays. The first assay was as described by Frey and Nicolet (supra); serial two-fold dilutions of 1 ml samples of all culture filtrates were incubated for 1 h at 37° C. with 10 μl samples of one of the MAbs, swine sera, or buffer. Then, 1 ml of a suspension of 1% sheep erythrocytes in Tris-buffered saline with $CaCl_2$ was added to each tube and from that point on the test was further performed as the hemolysin assay was. The hemolytic activity of the culture filtrates of serotypes 2, 3, 6, and 8 was too weak to determine inhibition. Therefore, we also tested inhibition of hemolytic activity by inoculating *A. pleuropneumoniae* serotypes 1 to 12 onto sheep blood agar plates that contained 0.05% nicotinamide adenine dinucleotide and a 1:100 dilution of one of the MAbs or a 1:200 dilution of the swine sera. Plates without antibodies were used as controls. The plates had a diameter of 5.5 cm and contained 5 ml medium each. Per serotype, one colony of an 18 hour old culture was suspended in 1 ml PBS. Very fine capillary tubes were used to inoculate the plates with these suspensions. After incubating the plates overnight at 37° C. in an atmosphere of 5% $CO_2$, hemolytic zones were measured and compared to those of the controls. Inhibition was expressed as when hemolytic zones were similar to those of the controls, as + when hemolytic zones were present but were more than 50% smaller than the controls, and as + when no hemolytic zones were detected.

Cytotoxin assay. The isolation of porcine alveolar macrophages and the cytotoxin assay have been described earlier in detail (Kamp, E. M. and L. A. M. G. van Leengoed (1989) *J. Clin. Microbiol.* 27: 1187–1191).

Cytotoxin inhibition assay. Serial two-fold dilutions of 50 μl samples of all culture filtrates (except serotype 6) were made in PBS in flat-bottomed microdilution plates (8 rows per serotype). Either PBS (control) or one of the MAbs or polyclonal swine sera were added to each row (50 μl per well). MAbs were used in a dilution of 1:100 and swine sera in a dilution of 1:200. Plates were sealed, shaken, and incubated for 1 h at 37° C. An amount of 50 μl alveolar macrophages was added to each well and from this point on, the test was performed as the cytotoxin assay was. Cytotoxin titers were determined and compared with the titer of the control. Inhibition was expressed as when cytotoxin titers were the same as the titer of the control, as + when titers were two to four-fold lower than the titer of the control, and as + when titers were more than four-fold lower than the titer of the control.

Sodium dodecyl polyacrylamide gel electrophoresis and Western blot analysis. Proteins in the culture filtrates were separated by sodium dodecyl sulfate polyacrylamide gel electrophoresis in a Mini Protean II slab cell according to the recommendations of the manufacturer (Bio-Rad, Richmond, Calif.). We used a 4% stacking gel with a 7.5% separating gel, an acrylamide/bisacrylamide ratio of 19/1, 0.75 mm spacers, and combs with 15 wells. Each well was loaded with 15 μl samples and electrophoresed at 25 V on ice. Proteins were transferred onto nitrocellulose filters electrophoretically according to the recommendations of the manufacturer of the Blot system (Novablot, LKB, Uppsala, Sweden). The blots were probed with a 1:200 dilution of the MAbs or a 1:400 dilution of the swine sera. Bound immunoglobulins were visualized by using peroxidase-labeled goat anti-mouse or goat antiswine immunoglobulins (Dakopatts) and HRP Color Development Reagent (Bio-Rad). Control blots were probed with buffer instead of MAb.

Results

Hemolytic and cytotoxic activities. Culture filtrates of all serotypes except of serotype 6 were cytotoxic and hemolytic (Table A). Hemolytic activity of culture filtrates of serotypes 2, 3, 4, 7, 8, and 12 were much weaker than those of serotypes 1, 5, 9, 10, and 11. All reference strains of *A. pleuropneumoniae* serotypes 1 to 12, including serotype 6, were hemolytic on blood agar. The hemolytic zones around colonies of serotypes 2, 3, 4, 7, 8, and 12 were much smaller than the zones around serotypes 1, 5, 9, 10, and 11. Hemolysis of serotype 6 could only be detected after removal of the colony.

Monoclonal antibodies and swine sera. For this study we selected five MAbs and two swine sera. MAb CVI-Apcly 2.2 was raised against serotype 2 and tested in ELISA positive with serotype 2 and negative with serotype 9. MAbs CVI-Apcly 9.1 and 9.2 were raised against serotype 9 and tested positive with serotype 9-and negative with serotype 2. In contrast, the two swine sera and MAbs CVI-Apcly 9.3 and 9.4, which were also raised against serotype 9, tested positive which both serotype 2 and 9. The MAbs did not block each other in a competition ELISA, indicating that they recognized different epitopes.

Inhibition of hemolytic and cytotoxic activity. MAbs and swine sera were tested for inhibition of hemolytic and cytotoxic activity of serotypes 1 to 12. MAb CVI-Apcly 9.1 and pig anti serotype 9 serum reduced the hemolytic activity of culture filtrates of serotypes 1, 5, 9, 10, and 11 with 80% or more. MAbs CVI-Apcly 9.3 and 9.4 and the swine sera against serotypes 2 and 9 totally reduced the hemolytic activity of the culture filtrates of serotypes 4, 7, and 12. Because the hemolytic activity of the culture filtrates of serotypes 2, 3, 6, and 8 was too weak to reliably determine inhibition of hemolysis in the liquid assay, we also tested the MAbs and swine sera for their ability to inhibit hemolysis on blood agar. The results of this test were similar to those of the liquid assay.

MAb CVI-Apcly 2.2 was raised against serotype 2 and inhibited cytotoxic activity of serotypes 2, 3, 4, and 8. MAb CVI-Apcly 9.1 was raised against serotype 9 and inhibited the hemolytic activity and the cytotoxic activity of serotypes 1, 5, 9, 10, and 11, suggesting that both activities are functions of the same protein. MAb CVI-Apcly 9.2 was also raised against serotype 9 and inhibited the cytotoxic but not the hemolytic activity of serotypes 1, 5, 9, 10, and 11. In contrast, MAbs CVI-Apcly 9.3 and 9.4, which were also raised against serotype 9, did not inhibit hemolytic or cytotoxic activity of these serotypes. Surprisingly, these two MAbs inhibited the hemolytic activity and cytotoxic activity of serotypes 7 and 12. This suggests that the hemolytic and cytotoxic activity of these serotypes are functions of the same protein. In addition, MAbs CVI-Apcly 9.3 and 9.4 inhibited the hemolytic but not the cytotoxic activity of serotypes 2, 3, 4, and 8.

Pig serum raised against serotype 2 inhibited the hemolytic and cytotoxic activity of serotypes 2, 3, 4, 6, 7, 8, and 12, whereas pig serum raised against serotype 9 inhibited the hemolytic and cytotoxic activity of serotypes 1, 5, 6, 7, 9, 10, 11, and 12 and the hemolytic but not the cytotoxic activity of serotypes 2, 3, 4, and 8.

Western blot analysis. The selected MAbs and swine sera were used to probe Western blots of the culture filtrates of serotypes 1 to 12. MAb CVI-Apcly 2.2 reacted with a protein of approximately 120 kDa in filtrates of serotypes 2, 3, 4, and 8. MAbs CVI-Apcly 9.1 and 9.2 reacted with a protein of approximately 105 kDa in filtrates of serotypes 1, 5, 9, 10, and 11 and MAb CVI-Apcly 9.3 reacted with a protein also of approximately 105 kDa in filtrates of all serotypes except serotype 10. The reaction of MAb CVI-Apcly 9.3 with the proteins of serotypes 3, 6, and 8 was very weak and not always visible.

To test whether MAbs CVI-Apcly 2.2, 9.1, 9.2, and 9.3 recognized different proteins, we probed a blot with one MAb, washed the blot thoroughly, and then tested it with another MAb. This procedure was repeated until all four MAbs were tested. Three proteins became visible. One protein of approximately 120 kDa was detected by MAb CVI-Apcly 2.2 in serotypes 2, 3, 4, and 8; a second protein of approximately 105 kDa was detected by MAbs CVI-Apcly 9.1 and 9.2 in serotypes 1, 5, 9, 10, and 11; and a third protein of approximately 103 kDa was detected by MAb CVI-Apcly 9.3 in all serotypes except serotype 10 (Table A).

MAb CVI-Apcly 9.4 reacted with the 105 kDa protein and the 103 kDa protein, indicating that these two proteins have epitopes in common.

Western blot analysis using the swine sera confirmed the distribution of the three proteins among the 12 serotypes. Pig serum raised against serotype 2 recognized a protein of approximately 120 kDa in serotypes 2, 3, 4, and 8 and a protein of approximately 103 kDa in all serotypes except serotype 10. Pig serum raised serotype 9 recognized a protein of approximately 105 kDa in serotypes 1, 5, 9, 10, and 11, and a protein of approximately 103 kDa in all serotypes except serotype 10.

EXAMPLE 4

Production of Cytolysins and Preparation of a Recombinant Vaccine

Figure 9:
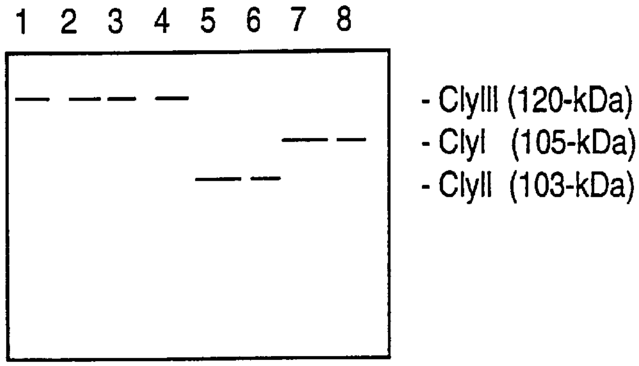
FIG. 9 illustrates the expression and secretion of cytolysins I, II, and III in recombinant *E. coli.*

Cells of *E. coli* strain LE 392 that contained plasmid pLG 575 (Gygi, D. et al. (1990) *Mol. Microbiol.* 4: 123–128) were transformed with plasmids that contained ClyI, ClyII, or ClyIII encoding genes. These cells were grown at 37° C. in Luria Broth medium, supplemented with the appropriate antibiotics and preferably with 10% Feutal Calf Serum, for about 6–8 h to an optical density at 620 nanometer of approximately 0.5. The culture was centrifuged, the supernatant was sterilized by treatment with a bacteriostaticum and stored. The proteins present in the culture supernatants and that reacted with a mixture of Mabs 9.1, 9.3 and 2.2 are shown in FIG. 9. The purified Cly proteins from those supernatants, or preferably the crude supernatants, are mixed in a predetermined ratio and subsequently mixed with an appropriate adjuvant and used for vaccination.

FIG. 9 is a diagrammatic representation of a Western blot showing expression and secretion of ClyIII (lanes 1–4), ClyII (lanes 5, 6) and ClyI (lanes 7, 8) by recombinant *E. coli* cells that contain the cytolysin gene in question together with transport genes of *E. coli* itself. The proteins were electrophoresed on SDS-PAGE, blotted on nitrocellulose and visualized with MAb 2.2, 9.1 and 9.3.

What is claimed is:

1. A vaccine comprising at least three isolated *Actinobacillus pleuropneumoniae* cytolysin proteins wherein at least one of the proteins is a ClyII protein having the amino acid sequence set forth in SEQ ID NO: 7 or 8, at least one of the proteins is a ClyI protein having the amino acid sequence set forth in SEQ ID NO: 2, 3, 4 or 5 and at least one of the proteins is a ClyIII protein having the sequence set forth in SEQ ID NO: 10.

2. The vaccine according to claim 1 wherein said at least one full-length isolated protein having a sequence from ClyI further has the sequence identified in SEQ ID NO. 2.

3. The vaccine according to claim 1 wherein said at least one full-length isolated protein having a sequence from ClyI further has the sequence identified in SEQ ID NO. 3.

4. The vaccine according to claim 1 wherein said at least one full-length isolated protein having a sequence from ClyI further has the sequence identified in SEQ ID NO. 4.

5. The vaccine according to claim 1 wherein said at least one full-length isolated protein having a sequence from ClyI further has the sequence identified in SEQ ID NO. 5.

* * * * *

UNITED STATES PATENT AND TRADEMARK OFFICE
CERTIFICATE OF CORRECTION

PATENT NO. : 6,500,435 B1 
DATED : December 31, 2002
INVENTOR(S) : Elbarte Margriet Kamp It is certified that error appears in the above-identified patent and that said Letters Patent is hereby corrected as shown below:

Title page,
Item [56], References Cited, OTHER PUBLICATIONS,"Strathdee" Reference "55:121" should read -- 55:12 --.

Column 4,
Line 27, "FIGS. 5A and 5B shows" should read -- FIGS. 5A and 5B show --.

Column 5,
Line 37, "4." should read -- 4, --;
Line 60, "3." should read -- 3, --.

Column 7,
Table A Column 8 Row 105 kDa = delete "-".

Column 13,
Line 33, "htyBD" should read -- hlyBD --.

Column 15,
Line 62, "$a^{32}P$" should read -- $\alpha^{32}P$ --.

Column 16,
Line 20, "$a^{32}P$" should read -- $\alpha^{32}P$ --.
Line 42, "a specific" should read -- aspecific --.

Column 17,
Line 8, "for-amplifiecation" should read -- for amplification --.
Line 27 "$a^{32}P$" should read -- $\alpha^{32}P$ --.

Column 19,
Line 35, "$A_{540, 20}$" should read -- $A_{540}$, 20 --.

UNITED STATES PATENT AND TRADEMARK OFFICE

CERTIFICATE OF CORRECTION

PATENT NO. : 6,500,435 B1
DATED : December 31, 2002
INVENTOR(S) : Elbarte Margriet Kamp It is certified that error appears in the above-identified patent and that said Letters Patent is hereby corrected as shown below:

Column 20,
Line 59, "which both" should read -- with both --.

Signed and Sealed this

Fifteenth Day of July, 2003

JAMES E. ROGAN
*Director of the United States Patent and Trademark Office*

SEQUENCE LISTING

```
<160> NUMBER OF SEQ ID NOS: 15

<210> SEQ ID NO 1
<211> LENGTH: 8370
<212> TYPE: DNA
<213> ORGANISM: Actinobacillus pleuropneumonia
<220> FEATURE:
<221> NAME/KEY: CDS
<222> LOCATION: (166)...(681)
<221> NAME/KEY: CDS
<222> LOCATION: (694)...(3732)
<221> NAME/KEY: CDS
<222> LOCATION: (3842)...(5962)
<221> NAME/KEY: CDS
<222> LOCATION: (5974)...(7410)

<400> SEQUENCE: 1
```

-continued

```
agattaatga gcgatattgt tataaaatca taatgtaaac ctcatttgta atgaattggt      60

aaattatata aataatcaaa aaacttactt ttttttattt ttatcggtaa gtatttacaa     120

tcaagtcaga caaacggcaa tattgttata aatctggggg gatga atg agt aaa aaa     177
                                                  Met Ser Lys Lys
                                                   1

att aat gga ttt gag gtt tta gga gag gtg gca tgg tta tgg gca agt       225
Ile Asn Gly Phe Glu Val Leu Gly Glu Val Ala Trp Leu Trp Ala Ser
 5                  10                  15                  20

tct cct tta cat cga aag tgg ccg ctt tct ttg tta gca att aat gtg       273
Ser Pro Leu His Arg Lys Trp Pro Leu Ser Leu Leu Ala Ile Asn Val
                25                  30                  35

cta cct gcg att gag agt aat caa tat gtt ttg tta aag cgt gac ggt       321
Leu Pro Ala Ile Glu Ser Asn Gln Tyr Val Leu Leu Lys Arg Asp Gly
            40                  45                  50

ttt cct att gca ttt tgt agc tgg gca aat ttg aat ttg gaa aat gaa       369
Phe Pro Ile Ala Phe Cys Ser Trp Ala Asn Leu Asn Leu Glu Asn Glu
        55                  60                  65

att aaa tac ctt gat gat gtt gcc tcg cta gtt gcg gat gat tgg act       417
Ile Lys Tyr Leu Asp Asp Val Ala Ser Leu Val Ala Asp Asp Trp Thr
    70                  75                  80

tcc ggc gat cgt cga tgg ttt ata gat tgg ata gca ccg ttc gga gac       465
Ser Gly Asp Arg Arg Trp Phe Ile Asp Trp Ile Ala Pro Phe Gly Asp
 85                  90                  95                 100

agt gcc gca tta tac aaa cat atg cga gat aac ttc ccg aat gag ctg       513
Ser Ala Ala Leu Tyr Lys His Met Arg Asp Asn Phe Pro Asn Glu Leu
                105                 110                 115

ttt agg gct att cga gtt gat ccg gac tct cga gta ggg aaa att tca       561
Phe Arg Ala Ile Arg Val Asp Pro Asp Ser Arg Val Gly Lys Ile Ser
            120                 125                 130

gaa ttt cat gga gga aaa att gat aag aaa ctg gca agt aaa att ttt       609
Glu Phe His Gly Gly Lys Ile Asp Lys Lys Leu Ala Ser Lys Ile Phe
        135                 140                 145

caa caa tat cac ttt gaa tta atg agt gag cta aaa aat aaa caa aat       657
Gln Gln Tyr His Phe Glu Leu Met Ser Glu Leu Lys Asn Lys Gln Asn
    150                 155                 160

ttt aaa ttt tca tta gta aat agc taaggagaca ac atg gct aac tct cag     708
Phe Lys Phe Ser Leu Val Asn Ser               Met Ala Asn Ser Gln
165                 170                                175

ctc gat aga gtc aaa gga ttg att gat tca ctt aat caa cat aca aaa       756
Leu Asp Arg Val Lys Gly Leu Ile Asp Ser Leu Asn Gln His Thr Lys
        180                 185                 190

agt gca gct aaa tca ggt gcc ggc gca tta aaa aat ggt ttg gga cag       804
Ser Ala Ala Lys Ser Gly Ala Gly Ala Leu Lys Asn Gly Leu Gly Gln
    195                 200                 205

gtg aag caa gca ggg cag aaa tta att tta tat att ccg aaa gat tat       852
Val Lys Gln Ala Gly Gln Lys Leu Ile Leu Tyr Ile Pro Lys Asp Tyr
210                 215                 220                 225

caa gct agt acc ggc tca agt ctt aat gat tta gtg aaa gcg gcg gag       900
Gln Ala Ser Thr Gly Ser Ser Leu Asn Asp Leu Val Lys Ala Ala Glu
                230                 235                 240

gct tta ggg atc gaa gta cat cgc tcg gaa aaa aac ggt acc gca cta       948
Ala Leu Gly Ile Glu Val His Arg Ser Glu Lys Asn Gly Thr Ala Leu
            245                 250                 255

gcg aaa gaa tta ttc ggt aca acg gaa aaa cta tta ggt ttc tcg gaa       996
Ala Lys Glu Leu Phe Gly Thr Thr Glu Lys Leu Leu Gly Phe Ser Glu
        260                 265                 270

cga ggc atc gca tta ttt gca cct cag ttt gat aag tta ctg aat aag      1044
Arg Gly Ile Ala Leu Phe Ala Pro Gln Phe Asp Lys Leu Leu Asn Lys
```

-continued

```
    275                 280                 285

aac caa aaa tta agt aaa tcg ctc ggc ggt tca tcg gaa gca tta gga      1092
Asn Gln Lys Leu Ser Lys Ser Leu Gly Gly Ser Ser Glu Ala Leu Gly
290                 295                 300                 305

caa cgt tta aat aaa acg caa acg gca ctt tca gcc tta caa agt ttc      1140
Gln Arg Leu Asn Lys Thr Gln Thr Ala Leu Ser Ala Leu Gln Ser Phe
                310                 315                 320

tta ggt acg gct att gcg ggt atg gat ctt gat agc ctg ctt cgt cgc      1188
Leu Gly Thr Ala Ile Ala Gly Met Asp Leu Asp Ser Leu Leu Arg Arg
            325                 330                 335

cgt aga aac ggt gag gac gac agt ggt tcg gaa tta gct aaa gca ggt      1236
Arg Arg Asn Gly Glu Asp Asp Ser Gly Ser Glu Leu Ala Lys Ala Gly
        340                 345                 350

gtg gat cta gcc gct cag tta gtg gat aac att gca agt gca acg ggt      1284
Val Asp Leu Ala Ala Gln Leu Val Asp Asn Ile Ala Ser Ala Thr Gly
    355                 360                 365

acg gtg gag gcg ttt gcc gaa caa tta ggt aaa ttg ggc aat gcc tta      1332
Thr Val Glu Ala Phe Ala Glu Gln Leu Gly Lys Leu Gly Asn Ala Leu
370                 375                 380                 385

tct aac act cgc tta agc ggt tta gca agt aag tta aat aac ctt cca      1380
Ser Asn Thr Arg Leu Ser Gly Leu Ala Ser Lys Leu Asn Asn Leu Pro
                390                 395                 400

gat tta agc ctt gca gga cct ggg ttt gat gcc gta tca ggt atc tta      1428
Asp Leu Ser Leu Ala Gly Pro Gly Phe Asp Ala Val Ser Gly Ile Leu
            405                 410                 415

tct gtt gtt tcg gct tca ttc att tta agt aat aaa gat gcc gat gca      1476
Ser Val Val Ser Ala Ser Phe Ile Leu Ser Asn Lys Asp Ala Asp Ala
        420                 425                 430

ggt aca aaa gcg gcg gca ggt att gaa atc tca act aaa atc tta ggc      1524
Gly Thr Lys Ala Ala Ala Gly Ile Glu Ile Ser Thr Lys Ile Leu Gly
    435                 440                 445

aat atc ggt aaa gcg gtt tct caa tat att att gcg caa cgt gtg gcg      1572
Asn Ile Gly Lys Ala Val Ser Gln Tyr Ile Ile Ala Gln Arg Val Ala
450                 455                 460                 465

gca ggc tta tcc aca act gcg gca acc ggt ggt tta atc ggt tcg gtc      1620
Ala Gly Leu Ser Thr Thr Ala Ala Thr Gly Gly Leu Ile Gly Ser Val
                470                 475                 480

gta gca tta gcg att agc ccg ctt tcg ttc tta att gtt gcg gat aag      1668
Val Ala Leu Ala Ile Ser Pro Leu Ser Phe Leu Ile Val Ala Asp Lys
            485                 490                 495

ttt gaa cgt gcg aaa cag ctt gaa caa tat tcg gag cgc ttt aaa aag      1716
Phe Glu Arg Ala Lys Gln Leu Glu Gln Tyr Ser Glu Arg Phe Lys Lys
        500                 505                 510

ttc ggt tat aaa ggt gat agt tta tta gct tca ttc tac cgt gaa acc      1764
Phe Gly Tyr Lys Gly Asp Ser Leu Leu Ala Ser Phe Tyr Arg Glu Thr
    515                 520                 525

ggt gcg att gaa gcg gca tta acc acg att aac agt gtg tta agt gcg      1812
Gly Ala Ile Glu Ala Ala Leu Thr Thr Ile Asn Ser Val Leu Ser Ala
530                 535                 540                 545

gct tcc gca ggt gtt ggg gct gct gca acc ggc tca tta gtc ggt gcg      1860
Ala Ser Ala Gly Val Gly Ala Ala Ala Thr Gly Ser Leu Val Gly Ala
                550                 555                 560

ccg gta gca gct tta gtt agt gca atc acc ggt att att tca ggt att      1908
Pro Val Ala Ala Leu Val Ser Ala Ile Thr Gly Ile Ile Ser Gly Ile
            565                 570                 575

tta gat gct tct aaa cag gca atc ttc gaa cga gtt gca acg aaa tta      1956
Leu Asp Ala Ser Lys Gln Ala Ile Phe Glu Arg Val Ala Thr Lys Leu
        580                 585                 590

gcg aat aag att gac gaa tgg gag aaa aaa cac ggt aaa aac tat ttt      2004
```

-continued

```
Ala Asn Lys Ile Asp Glu Trp Glu Lys Lys His Gly Lys Asn Tyr Phe
    595                 600                 605

gaa aac ggt tat gac gcc cgc cat tcc gca ttc tta gaa gat acc ttt      2052
Glu Asn Gly Tyr Asp Ala Arg His Ser Ala Phe Leu Glu Asp Thr Phe
610                 615                 620                 625

gaa ttg tta tca caa tac aat aaa gag tat tcg gta gag cgt gtc gtt      2100
Glu Leu Leu Ser Gln Tyr Asn Lys Glu Tyr Ser Val Glu Arg Val Val
                630                 635                 640

gct att acg caa cag cgt tgg gat gtc aat atc ggt gaa ctt gcc ggc      2148
Ala Ile Thr Gln Gln Arg Trp Asp Val Asn Ile Gly Glu Leu Ala Gly
            645                 650                 655

att act cgc aaa ggt tct gat acg aaa agc ggt aaa gct tac gtt gat      2196
Ile Thr Arg Lys Gly Ser Asp Thr Lys Ser Gly Lys Ala Tyr Val Asp
        660                 665                 670

ttc ttt gaa gaa gga aaa ctt tta gag aaa gaa ccg gat cgt ttt gat      2244
Phe Phe Glu Glu Gly Lys Leu Leu Glu Lys Glu Pro Asp Arg Phe Asp
    675                 680                 685

aaa aaa gtg aaa gat ccg ctt gaa ggt aaa atc gac ctt tct tca att      2292
Lys Lys Val Lys Asp Pro Leu Glu Gly Lys Ile Asp Leu Ser Ser Ile
690                 695                 700                 705

aac aaa acc act tta ttg aaa ttt gtt acc ccg gtc ttt acc gca ggt      2340
Asn Lys Thr Thr Leu Leu Lys Phe Val Thr Pro Val Phe Thr Ala Gly
                710                 715                 720

gaa gag att cgt gag cgt aag caa acc ggt aaa tac gaa tat atg acc      2388
Glu Glu Ile Arg Glu Arg Lys Gln Thr Gly Lys Tyr Glu Tyr Met Thr
            725                 730                 735

gaa tta ttc gtt aaa ggt aaa gaa aaa tgg gtg gta acc ggt gtg cag      2436
Glu Leu Phe Val Lys Gly Lys Glu Lys Trp Val Val Thr Gly Val Gln
        740                 745                 750

tca cat aat gcg att tat gac tat acg aat ctt atc caa tta gcg ata      2484
Ser His Asn Ala Ile Tyr Asp Tyr Thr Asn Leu Ile Gln Leu Ala Ile
    755                 760                 765

gat aaa aaa ggt gaa aaa cgt caa gtg acc att gaa tct cat ttg ggt      2532
Asp Lys Lys Gly Glu Lys Arg Gln Val Thr Ile Glu Ser His Leu Gly
770                 775                 780                 785

gag aaa aat gat cgt ata tat ctt tca tcc ggt tca tct atc gta tat      2580
Glu Lys Asn Asp Arg Ile Tyr Leu Ser Ser Gly Ser Ser Ile Val Tyr
                790                 795                 800

gcg ggt aac gga cat gat gta gca tat tac gat aaa acc gat aca ggt      2628
Ala Gly Asn Gly His Asp Val Ala Tyr Tyr Asp Lys Thr Asp Thr Gly
            805                 810                 815

tac tta aca ttt gac gga caa agt gca cag aaa gcc ggt gaa tat att      2676
Tyr Leu Thr Phe Asp Gly Gln Ser Ala Gln Lys Ala Gly Glu Tyr Ile
        820                 825                 830

gtc act aaa gaa ctt aaa gct gat gta aaa gtt tta aaa gaa gtg gtt      2724
Val Thr Lys Glu Leu Lys Ala Asp Val Lys Val Leu Lys Glu Val Val
    835                 840                 845

aaa act cag gat att tca gtt gga aaa cgc agt gaa aaa tta gaa tat      2772
Lys Thr Gln Asp Ile Ser Val Gly Lys Arg Ser Glu Lys Leu Glu Tyr
850                 855                 860                 865

cgt gat tat gag tta agc cca ttc gaa ctt ggg aac ggt atc aga gct      2820
Arg Asp Tyr Glu Leu Ser Pro Phe Glu Leu Gly Asn Gly Ile Arg Ala
                870                 875                 880

aaa gat gaa tta cat tct gtt gaa gaa att atc ggt agt aat cgt aaa      2868
Lys Asp Glu Leu His Ser Val Glu Glu Ile Ile Gly Ser Asn Arg Lys
            885                 890                 895

gac aaa ttc ttt ggt agt cgc ttt acc gat att ttc cat ggt gcg aaa      2916
Asp Lys Phe Phe Gly Ser Arg Phe Thr Asp Ile Phe His Gly Ala Lys
        900                 905                 910
```

-continued

```
ggc gat gat gaa atc tac ggt aat gac ggc cac gat atc tta tac gga     2964
Gly Asp Asp Glu Ile Tyr Gly Asn Asp Gly His Asp Ile Leu Tyr Gly
    915                 920                 925

gac gac ggt aat gat gta atc cat ggc ggt gac ggt aac gac cat ctt     3012
Asp Asp Gly Asn Asp Val Ile His Gly Gly Asp Gly Asn Asp His Leu
930                 935                 940                 945

gtt ggt ggt aac gga aac gac cga tta atc ggc gga aaa ggt aat aat     3060
Val Gly Gly Asn Gly Asn Asp Arg Leu Ile Gly Gly Lys Gly Asn Asn
                950                 955                 960

ttc ctt aat ggc ggt gat ggt gac gat gag ttg cag gtc ttt gag ggt     3108
Phe Leu Asn Gly Gly Asp Gly Asp Asp Glu Leu Gln Val Phe Glu Gly
            965                 970                 975

caa tac aac gta tta tta ggt ggt gcg ggt aat gac att ctg tat ggc     3156
Gln Tyr Asn Val Leu Leu Gly Gly Ala Gly Asn Asp Ile Leu Tyr Gly
        980                 985                 990

agc gat ggt act aac tta ttt gac ggt ggt gta ggc aat gac aaa atc     3204
Ser Asp Gly Thr Asn Leu Phe Asp Gly Gly Val Gly Asn Asp Lys Ile
     995                1000                1005

tac ggt ggt tta ggt aag gat att tat cgc tac agt aag gag tac ggt     3252
Tyr Gly Gly Leu Gly Lys Asp Ile Tyr Arg Tyr Ser Lys Glu Tyr Gly
1010                1015                1020                1025

cgt cat atc att att gag aaa ggc ggt gat gat gat acg tta ttg tta     3300
Arg His Ile Ile Ile Glu Lys Gly Gly Asp Asp Asp Thr Leu Leu Leu
                1030                1035                1040

tcg gat ctt agt ttt aaa gat gta gga ttt atc aga atc ggt gat gat     3348
Ser Asp Leu Ser Phe Lys Asp Val Gly Phe Ile Arg Ile Gly Asp Asp
            1045                1050                1055

ctt ctt gtg aat aaa aga atc gga gga aca ctg tat tac cat gaa gat     3396
Leu Leu Val Asn Lys Arg Ile Gly Gly Thr Leu Tyr Tyr His Glu Asp
        1060                1065                1070

tac aat ggg aat gcg ctc acg att aaa gat tgg ttc aag gaa ggt aaa     3444
Tyr Asn Gly Asn Ala Leu Thr Ile Lys Asp Trp Phe Lys Glu Gly Lys
    1075                1080                1085

gaa gga caa aat aat aaa att gaa aaa atc gtt gat aaa gat gga gct     3492
Glu Gly Gln Asn Asn Lys Ile Glu Lys Ile Val Asp Lys Asp Gly Ala
1090                1095                1100                1105

tat gtt tta agc caa tat ctg act gaa ctg aca gct cct gga aga ggt     3540
Tyr Val Leu Ser Gln Tyr Leu Thr Glu Leu Thr Ala Pro Gly Arg Gly
                1110                1115                1120

atc aat tac ttt aat ggg tta gaa gaa aaa ttg tat tat gga gaa gga     3588
Ile Asn Tyr Phe Asn Gly Leu Glu Glu Lys Leu Tyr Tyr Gly Glu Gly
            1125                1130                1135

tat aat gca ctt cct caa ctc aga aaa gat att gaa caa atc att tca     3636
Tyr Asn Ala Leu Pro Gln Leu Arg Lys Asp Ile Glu Gln Ile Ile Ser
        1140                1145                1150

tct acg ggt gca ttt acc ggt gac cac gga aaa gta tct gta ggc tca     3684
Ser Thr Gly Ala Phe Thr Gly Asp His Gly Lys Val Ser Val Gly Ser
    1155                1160                1165

ggc gga ccg tta gtc tat aat aac tca gct aac aat gta gca att ctt     3732
Gly Gly Pro Leu Val Tyr Asn Asn Ser Ala Asn Asn Val Ala Ile Leu
1170                1175                1180                1185

tgagttattc tttagcacaa gcagcttaag atagttattt ttagatgata aatagcaatc   3792

ctatatatat taggtgtgta ggattgctat tttatttatg gaggagcaa atg gat ttt   3850
                                                      Met Asp Phe

tat cgg gaa gaa gac tac gga tta tac gca ctg acg att tta gcc cag     3898
Tyr Arg Glu Glu Asp Tyr Gly Leu Tyr Ala Leu Thr Ile Leu Ala Gln
    1190                1195                1200

tac cat aat att gct gta aat ccg gaa gaa cta aaa cat aaa ttc gac     3946
Tyr His Asn Ile Ala Val Asn Pro Glu Glu Leu Lys His Lys Phe Asp
```

-continued 1205 1210 1215 1220 ctt gaa gga aaa ggc tta gat cta acc gct tgg cta tta gcc gca aaa 3994
Leu Glu Gly Lys Gly Leu Asp Leu Thr Ala Trp Leu Leu Ala Ala Lys
1225 1230 1235 tca tta gaa ctt aaa gca aaa caa gta aaa aaa gcg att gat cgt ttg 4042
Ser Leu Glu Leu Lys Ala Lys Gln Val Lys Lys Ala Ile Asp Arg Leu
1240 1245 1250 gcg ttt atc gga cta ccg gca ctt gta tgg cga gaa gac ggt aaa cat 4090
Ala Phe Ile Gly Leu Pro Ala Leu Val Trp Arg Glu Asp Gly Lys His
1255 1260 1265 ttt att ttg act aaa att gat aat gaa gca aaa aaa tat tta att ttt 4138
Phe Ile Leu Thr Lys Ile Asp Asn Glu Ala Lys Lys Tyr Leu Ile Phe
1270 1275 1280 gat ttg gaa acg cat aat cct cgc att ttg gaa caa gcg gaa ttc gag 4186
Asp Leu Glu Thr His Asn Pro Arg Ile Leu Glu Gln Ala Glu Phe Glu
1285 1290 1295 1300 agc tta tac caa gga aaa ctg att tta gtt gca tca aga gct tcc atc 4234
Ser Leu Tyr Gln Gly Lys Leu Ile Leu Val Ala Ser Arg Ala Ser Ile
1305 1310 1315 gta ggt aag ctg gca aag ttt gac ttc act tgg ttt ata ccg gcg gta 4282
Val Gly Lys Leu Ala Lys Phe Asp Phe Thr Trp Phe Ile Pro Ala Val
1320 1325 1330 att aag tat cgt aag att ttt att gaa acg tta att gtt tca att ttt 4330
Ile Lys Tyr Arg Lys Ile Phe Ile Glu Thr Leu Ile Val Ser Ile Phe
1335 1340 1345 ttg caa att ttc gca cta att aca ccg ctt ttt ttc caa gtc gtg atg 4378
Leu Gln Ile Phe Ala Leu Ile Thr Pro Leu Phe Phe Gln Val Val Met
1350 1355 1360 gat aaa gtc ttg gta cac cga ggt ttt tca acc tta aat gtg att acg 4426
Asp Lys Val Leu Val His Arg Gly Phe Ser Thr Leu Asn Val Ile Thr
1365 1370 1375 1380 gtg gca tta gcg atc gtc gtg ctg ttt gaa att gtg cta aac ggt tta 4474
Val Ala Leu Ala Ile Val Val Leu Phe Glu Ile Val Leu Asn Gly Leu
1385 1390 1395 cgt acc tat att ttt gcg cat agt acc agc cgt att gat gtg gag ttg 4522
Arg Thr Tyr Ile Phe Ala His Ser Thr Ser Arg Ile Asp Val Glu Leu
1400 1405 1410 gga gca aga tta ttc aga cat tta tta gca ctc cca atc tct tat ttt 4570
Gly Ala Arg Leu Phe Arg His Leu Leu Ala Leu Pro Ile Ser Tyr Phe
1415 1420 1425 gaa aat cgt cga gtc ggc gat acg gtg gct cgt gta cga gaa ctc gat 4618
Glu Asn Arg Arg Val Gly Asp Thr Val Ala Arg Val Arg Glu Leu Asp
1430 1435 1440 caa att cgt aac ttc tta acc ggg cag gca ctt act tcc gtg ttg gat 4666
Gln Ile Arg Asn Phe Leu Thr Gly Gln Ala Leu Thr Ser Val Leu Asp
1445 1450 1455 1460 tta atg ttt tcc ttt atc ttc ttt gca gtg atg tgg tat tac agc cct 4714
Leu Met Phe Ser Phe Ile Phe Phe Ala Val Met Trp Tyr Tyr Ser Pro
1465 1470 1475 aaa ctt act ctt gtg att tta ggc tcg tta ccg ttt tat atg ggg tgg 4762
Lys Leu Thr Leu Val Ile Leu Gly Ser Leu Pro Phe Tyr Met Gly Trp
1480 1485 1490 tcg att ttt atc agc cct att tta cgt cgc cgt tta gat gaa aaa ttc 4810
Ser Ile Phe Ile Ser Pro Ile Leu Arg Arg Arg Leu Asp Glu Lys Phe
1495 1500 1505 gca cgt ggt gcg gac aat cag tca ttc tta gtg gaa tcg gtg act gca 4858
Ala Arg Gly Ala Asp Asn Gln Ser Phe Leu Val Glu Ser Val Thr Ala
1510 1515 1520 atc aat acg att aaa gcg ttg gcg gtt acc cct caa atg act aat acc 4906

-continued

```
Ile Asn Thr Ile Lys Ala Leu Ala Val Thr Pro Gln Met Thr Asn Thr
1525                1530                1535                1540

tgg gat aag caa tta gcc agc tat gta tcg gcg gga ttc cgt gta acc      4954
Trp Asp Lys Gln Leu Ala Ser Tyr Val Ser Ala Gly Phe Arg Val Thr
                1545                1550                1555

aca tta gct act atc gga cag caa ggt gta caa ttt att caa aaa gtc      5002
Thr Leu Ala Thr Ile Gly Gln Gln Gly Val Gln Phe Ile Gln Lys Val
            1560                1565                1570

gtg atg gtt att acc tta tgg cta ggc gca cat tta gtg att tca ggc      5050
Val Met Val Ile Thr Leu Trp Leu Gly Ala His Leu Val Ile Ser Gly
        1575                1580                1585

gat tta agt atc gga caa tta atc gca ttt aat atg tta tcc ggt caa      5098
Asp Leu Ser Ile Gly Gln Leu Ile Ala Phe Asn Met Leu Ser Gly Gln
    1590                1595                1600

gtg att gca ccg gtg att cgt tta gcg caa ctt tgg caa gat ttc caa      5146
Val Ile Ala Pro Val Ile Arg Leu Ala Gln Leu Trp Gln Asp Phe Gln
1605                1610                1615                1620

caa gtg gga att tcg gta acg cgt tta ggt gat gtt tta aac tct ccg      5194
Gln Val Gly Ile Ser Val Thr Arg Leu Gly Asp Val Leu Asn Ser Pro
                1625                1630                1635

acc gag agc tat caa gga aaa ttg gcg tta ccg gaa att aaa ggc gat      5242
Thr Glu Ser Tyr Gln Gly Lys Leu Ala Leu Pro Glu Ile Lys Gly Asp
            1640                1645                1650

att acc ttc cgt aat ata cgc ttc cgc tac aaa ccg gat gcg ccg ctc      5290
Ile Thr Phe Arg Asn Ile Arg Phe Arg Tyr Lys Pro Asp Ala Pro Leu
        1655                1660                1665

att tta aat gat gtg aat tta tcg att cag caa ggt gaa gtg atc ggt      5338
Ile Leu Asn Asp Val Asn Leu Ser Ile Gln Gln Gly Glu Val Ile Gly
    1670                1675                1680

atc gta gga cgt tca ggc tca ggg aag agc acc tta acg aaa tta att      5386
Ile Val Gly Arg Ser Gly Ser Gly Lys Ser Thr Leu Thr Lys Leu Ile
1685                1690                1695                1700

caa cgt ttt tat att ccg gaa aac ggt cag gta tta ata gat ggg cat      5434
Gln Arg Phe Tyr Ile Pro Glu Asn Gly Gln Val Leu Ile Asp Gly His
                1705                1710                1715

gat tta gca ttg gcg gat ccg aac tgg cta cgt cgt caa gtc ggg gtg      5482
Asp Leu Ala Leu Ala Asp Pro Asn Trp Leu Arg Arg Gln Val Gly Val
            1720                1725                1730

gta tta caa gat aac gta cta tta aat cgt agt att cga gat aat att      5530
Val Leu Gln Asp Asn Val Leu Leu Asn Arg Ser Ile Arg Asp Asn Ile
        1735                1740                1745

gcc tta gcg gat ccg ggt atg cca atg gaa aaa att gtc cat gcg gca      5578
Ala Leu Ala Asp Pro Gly Met Pro Met Glu Lys Ile Val His Ala Ala
    1750                1755                1760

aaa tta gcc ggc gca cat gaa ttt att tct gaa ttg cgt gag gga tat      5626
Lys Leu Ala Gly Ala His Glu Phe Ile Ser Glu Leu Arg Glu Gly Tyr
1765                1770                1775                1780

aac acg att gtt ggt gag caa ggt gcg ggg cta tct ggc ggg caa cgc      5674
Asn Thr Ile Val Gly Glu Gln Gly Ala Gly Leu Ser Gly Gly Gln Arg
                1785                1790                1795

caa cgt att gcg att gca cgc gct ttg gtg aat aac ccg aaa atc tta      5722
Gln Arg Ile Ala Ile Ala Arg Ala Leu Val Asn Asn Pro Lys Ile Leu
            1800                1805                1810

att ttt gat gaa gcg acc agc gca tta gat tat gaa tcc gag cat atc      5770
Ile Phe Asp Glu Ala Thr Ser Ala Leu Asp Tyr Glu Ser Glu His Ile
        1815                1820                1825

atc atg cgc aat atg cac cag att tgt aaa ggg aga acg gta att atc      5818
Ile Met Arg Asn Met His Gln Ile Cys Lys Gly Arg Thr Val Ile Ile
    1830                1835                1840
```

-continued

```
att gca cac cgt tta tct acg gta aaa aat gcc gac cgt att att gtg     5866
Ile Ala His Arg Leu Ser Thr Val Lys Asn Ala Asp Arg Ile Ile Val
1845                1850                1855                1860

atg gaa aaa ggt cag att gtg gaa caa ggt aag cat aaa gag ctg ctt     5914
Met Glu Lys Gly Gln Ile Val Glu Gln Gly Lys His Lys Glu Leu Leu
                1865                1870                1875

gct gat cca aac ggc tta tat cac tac tta cac caa tta caa tcg gaa     5962
Ala Asp Pro Asn Gly Leu Tyr His Tyr Leu His Gln Leu Gln Ser Glu
            1880                1885                1890

taggaggact t atg aaa act tgg cta atg ggt tta tat gag ttt ttc caa    6012
             Met Lys Thr Trp Leu Met Gly Leu Tyr Glu Phe Phe Gln
                     1895                1900                1905

cgc tat aaa acg gtt tgg acg gag atc tgg aaa att cgt cat caa ttg     6060
Arg Tyr Lys Thr Val Trp Thr Glu Ile Trp Lys Ile Arg His Gln Leu
                1910                1915                1920

gat acg ccg gat cga gaa aag gat gaa aat gaa ttt tta cct gca cac     6108
Asp Thr Pro Asp Arg Glu Lys Asp Glu Asn Glu Phe Leu Pro Ala His
            1925                1930                1935

tta gag ctg att gaa aca ccg gtg tca aaa aaa ccg aga ttg atc gct     6156
Leu Glu Leu Ile Glu Thr Pro Val Ser Lys Lys Pro Arg Leu Ile Ala
        1940                1945                1950

tat tta att atg ctg ttc cta ttt ttg gca tta gtt att tca att gtc     6204
Tyr Leu Ile Met Leu Phe Leu Phe Leu Ala Leu Val Ile Ser Ile Val
    1955                1960                1965

agt cac gta gaa att gtg gcg acc gca acg ggt aaa tta gcg ttt agc     6252
Ser His Val Glu Ile Val Ala Thr Ala Thr Gly Lys Leu Ala Phe Ser
1970                1975                1980                1985

gac cgt agc aaa gaa att aag ccg att gaa aac gcc ttg gtt aaa gaa     6300
Asp Arg Ser Lys Glu Ile Lys Pro Ile Glu Asn Ala Leu Val Lys Glu
                1990                1995                2000

atc ttt gtg caa gac gga caa ttt gtt gag aaa gat cag ttg ctg tta     6348
Ile Phe Val Gln Asp Gly Gln Phe Val Glu Lys Asp Gln Leu Leu Leu
            2005                2010                2015

cac ttg acc gca ttg gga gcc gat gcg gat caa caa aaa acc aaa agt     6396
His Leu Thr Ala Leu Gly Ala Asp Ala Asp Gln Gln Lys Thr Lys Ser
        2020                2025                2030

tcg tta tcg ctg act aaa ttg gaa cgt tat cgt tat gaa att tta tta     6444
Ser Leu Ser Leu Thr Lys Leu Glu Arg Tyr Arg Tyr Glu Ile Leu Leu
    2035                2040                2045

gag gcg gtt gcg gcg gat agg ttg ccg ctc att gaa ctg aca aag gat     6492
Glu Ala Val Ala Ala Asp Arg Leu Pro Leu Ile Glu Leu Thr Lys Asp
2050                2055                2060                2065

gaa ttt aaa cat gct acg gaa gaa gat aaa acc aga att cgc tat ttg     6540
Glu Phe Lys His Ala Thr Glu Glu Asp Lys Thr Arg Ile Arg Tyr Leu
                2070                2075                2080

atc acc gag caa ttt gaa gct tgg caa aag caa aag tat caa aaa gaa     6588
Ile Thr Glu Gln Phe Glu Ala Trp Gln Lys Gln Lys Tyr Gln Lys Glu
            2085                2090                2095

tta gct ttg caa cgt aga gaa gca gaa aaa caa acg gtt cta gct aat     6636
Leu Ala Leu Gln Arg Arg Glu Ala Glu Lys Gln Thr Val Leu Ala Asn
        2100                2105                2110

att cgt aaa tat gag gga atc agt cga gtt gaa aat gaa aga tta aaa     6684
Ile Arg Lys Tyr Glu Gly Ile Ser Arg Val Glu Asn Glu Arg Leu Lys
    2115                2120                2125

gat ctt aaa aaa tta ttt aat tcg aaa tcg act tct aaa cat gat gtc     6732
Asp Leu Lys Lys Leu Phe Asn Ser Lys Ser Thr Ser Lys His Asp Val
2130                2135                2140                2145

ttg act caa gaa aat cgt cat atc gaa gcg gta aat gag ttg gcg gtg     6780
Leu Thr Gln Glu Asn Arg His Ile Glu Ala Val Asn Glu Leu Ala Val
                2150                2155                2160
```

-continued

```
tat aaa tct cgg ttg aat gaa gtg gaa agt gac tta cgt caa gcc aaa     6828
Tyr Lys Ser Arg Leu Asn Glu Val Glu Ser Asp Leu Arg Gln Ala Lys
            2165                2170                2175

gag gaa ata cat tta ata act cag ttg ttt aga gcc gat att ctg gag     6876
Glu Glu Ile His Leu Ile Thr Gln Leu Phe Arg Ala Asp Ile Leu Glu
        2180                2185                2190

aag ttg aaa caa aat gtt gaa gcg gag aaa cag ctt tcg ctc gaa tta     6924
Lys Leu Lys Gln Asn Val Glu Ala Glu Lys Gln Leu Ser Leu Glu Leu
    2195                2200                2205

gaa aaa aat gag cag cgt caa att gct tcg gtg att cgt gcg ccg gtt     6972
Glu Lys Asn Glu Gln Arg Gln Ile Ala Ser Val Ile Arg Ala Pro Val
2210                2215                2220                2225

tcc ggt acg gtt cag caa ctt aaa acc cat acg gta ggc ggc gtc gtg     7020
Ser Gly Thr Val Gln Gln Leu Lys Thr His Thr Val Gly Gly Val Val
                2230                2235                2240

acg act gcc gaa acc ttg atg gta att gct ccg gaa gat gat gtt tta     7068
Thr Thr Ala Glu Thr Leu Met Val Ile Ala Pro Glu Asp Asp Val Leu
            2245                2250                2255

gag gta acg gcg tta att caa aat aag gat atc ggt ttt atc gag gtc     7116
Glu Val Thr Ala Leu Ile Gln Asn Lys Asp Ile Gly Phe Ile Glu Val
        2260                2265                2270

ggt cag gat gcg gtg att aaa gta gaa act ttt cct tat act cgt tac     7164
Gly Gln Asp Ala Val Ile Lys Val Glu Thr Phe Pro Tyr Thr Arg Tyr
    2275                2280                2285

ggc tat tta atg ggt aaa gta aaa aat atc acg ctg gaa gcc atc gaa     7212
Gly Tyr Leu Met Gly Lys Val Lys Asn Ile Thr Leu Glu Ala Ile Glu
2290                2295                2300                2305

cat ccg caa ctc ggt cta att ttt aac tcg att att tct att gat aga     7260
His Pro Gln Leu Gly Leu Ile Phe Asn Ser Ile Ile Ser Ile Asp Arg
                2310                2315                2320

aaa act tta tcc ggc aaa gac ggc aaa gaa att gaa ctt gga tca ggt     7308
Lys Thr Leu Ser Gly Lys Asp Gly Lys Glu Ile Glu Leu Gly Ser Gly
            2325                2330                2335

atg agt gtg acc gcg gaa att aaa act gga gaa cgt agc gtt att agt     7356
Met Ser Val Thr Ala Glu Ile Lys Thr Gly Glu Arg Ser Val Ile Ser
        2340                2345                2350

tat tta ctc agt ccg ttg gaa gaa tcc gtt tcg gag agt tta aga gaa     7404
Tyr Leu Leu Ser Pro Leu Glu Glu Ser Val Ser Glu Ser Leu Arg Glu
    2355                2360                2365

cgc taa agcagataaa acaagcggcc atattttctt actttttgc aaaaaacgta      7460
Arg
2370

tgaaatatga ccgcttgtcg tttgtaaaag actatttatt tacaataatt ttagcaccgt   7520

tagaaaatac gatctgacga gcttcaaatt gagcggagag ctgtgcttgc gggtttagaa   7580

atacggcttg tgcttcttgc ggtaagtctg aaaccggtac gcaaaggcaa gttccgccgt   7640

ggtttggcgt tttaagttat ctttaaaggt aacgggcgca tcttgcgtga ggataacttt   7700

atcattgtaa acatagttta ccgcccattg aacgatacga atattgcgtt tggttttatt   7760

ttcaatactg tatttaaagc taaccatcgg ctgcccttct ttatttttag ccaattcata   7820

accgaaaaaa cgtaacccga tactgtcatt aaattgttta aggcgttttt ctttagccga   7880

aagaggtgca tttttcgtta ctgatttatg ttcaaccgtc ggttgaattt tattgccttc   7940

agcttgagca ttaaacgcta aaaagaatga tgctaccgcc gtgctaagta atttaatgtg   8000

tttcataatt cacctcgtaa tgagagctaa aagccgactt gatatattac gctatatatt   8060

gtcagattta cggcacagtt gcaatgaccg cataaccgtc cgattcggca ataatctcga   8120
```

-continued

```
cttggctttc cgccgcaatg aaaatcgctt cgccttgttg gagataaatg gactcttcac   8180

cgaggtcgat atagatactg cctttcatca ccaataagat acttgcacag tcggccgtaa   8240

agttttcttc gtcaaatgcg ttgaattgca tatgttgcaa tgcaaaatct ttcgcttcag   8300

gcgtcggata aagatgaatg aaaccgtcgt tttcttgata aggcggaata acttcggggt   8360

aatcgggcga                                                          8370


<210> SEQ ID NO 2
<211> LENGTH: 172
<212> TYPE: PRT
<213> ORGANISM: Actinobacillus pleuropneumonia

<400> SEQUENCE: 2

Met Ser Lys Lys Ile Asn Gly Phe Glu Val Leu Gly Glu Val Ala Trp
 1               5                  10                  15

Leu Trp Ala Ser Ser Pro Leu His Arg Lys Trp Pro Leu Ser Leu Leu
            20                  25                  30

Ala Ile Asn Val Leu Pro Ala Ile Glu Ser Asn Gln Tyr Val Leu Leu
        35                  40                  45

Lys Arg Asp Gly Phe Pro Ile Ala Phe Cys Ser Trp Ala Asn Leu Asn
    50                  55                  60

Leu Glu Asn Glu Ile Lys Tyr Leu Asp Asp Val Ala Ser Leu Val Ala
65                  70                  75                  80

Asp Asp Trp Thr Ser Gly Asp Arg Arg Trp Phe Ile Asp Trp Ile Ala
                85                  90                  95

Pro Phe Gly Asp Ser Ala Ala Leu Tyr Lys His Met Arg Asp Asn Phe
            100                 105                 110

Pro Asn Glu Leu Phe Arg Ala Ile Arg Val Asp Pro Asp Ser Arg Val
        115                 120                 125

Gly Lys Ile Ser Glu Phe His Gly Gly Lys Ile Asp Lys Lys Leu Ala
    130                 135                 140

Ser Lys Ile Phe Gln Gln Tyr His Phe Glu Leu Met Ser Glu Leu Lys
145                 150                 155                 160

Asn Lys Gln Asn Phe Lys Phe Ser Leu Val Asn Ser
                165                 170


<210> SEQ ID NO 3
<211> LENGTH: 1013
<212> TYPE: PRT
<213> ORGANISM: Actinobacillus pleuropneumonia

<400> SEQUENCE: 3

Met Ala Asn Ser Gln Leu Asp Arg Val Lys Gly Leu Ile Asp Ser Leu
 1               5                  10                  15

Asn Gln His Thr Lys Ser Ala Ala Lys Ser Gly Ala Gly Ala Leu Lys
            20                  25                  30

Asn Gly Leu Gly Gln Val Lys Gln Ala Gly Gln Lys Leu Ile Leu Tyr
        35                  40                  45

Ile Pro Lys Asp Tyr Gln Ala Ser Thr Gly Ser Ser Leu Asn Asp Leu
    50                  55                  60

Val Lys Ala Ala Glu Ala Leu Gly Ile Glu Val His Arg Ser Glu Lys
65                  70                  75                  80

Asn Gly Thr Ala Leu Ala Lys Glu Leu Phe Gly Thr Thr Glu Lys Leu
                85                  90                  95

Leu Gly Phe Ser Glu Arg Gly Ile Ala Leu Phe Ala Pro Gln Phe Asp
            100                 105                 110
```

-continued

```
Lys Leu Leu Asn Lys Asn Gln Lys Leu Ser Lys Ser Leu Gly Gly Ser
        115                 120                 125

Ser Glu Ala Leu Gly Gln Arg Leu Asn Lys Thr Gln Thr Ala Leu Ser
    130                 135                 140

Ala Leu Gln Ser Phe Leu Gly Thr Ala Ile Ala Gly Met Asp Leu Asp
145                 150                 155                 160

Ser Leu Leu Arg Arg Arg Arg Asn Gly Glu Asp Asp Ser Gly Ser Glu
                165                 170                 175

Leu Ala Lys Ala Gly Val Asp Leu Ala Ala Gln Leu Val Asp Asn Ile
            180                 185                 190

Ala Ser Ala Thr Gly Thr Val Glu Ala Phe Ala Glu Gln Leu Gly Lys
        195                 200                 205

Leu Gly Asn Ala Leu Ser Asn Thr Arg Leu Ser Gly Leu Ala Ser Lys
    210                 215                 220

Leu Asn Asn Leu Pro Asp Leu Ser Leu Ala Gly Pro Gly Phe Asp Ala
225                 230                 235                 240

Val Ser Gly Ile Leu Ser Val Val Ser Ala Ser Phe Ile Leu Ser Asn
                245                 250                 255

Lys Asp Ala Asp Ala Gly Thr Lys Ala Ala Ala Gly Ile Glu Ile Ser
            260                 265                 270

Thr Lys Ile Leu Gly Asn Ile Gly Lys Ala Val Ser Gln Tyr Ile Ile
        275                 280                 285

Ala Gln Arg Val Ala Ala Gly Leu Ser Thr Thr Ala Ala Thr Gly Gly
    290                 295                 300

Leu Ile Gly Ser Val Val Ala Leu Ala Ile Ser Pro Leu Ser Phe Leu
305                 310                 315                 320

Ile Val Ala Asp Lys Phe Glu Arg Ala Lys Gln Leu Glu Gln Tyr Ser
                325                 330                 335

Glu Arg Phe Lys Lys Phe Gly Tyr Lys Gly Asp Ser Leu Leu Ala Ser
            340                 345                 350

Phe Tyr Arg Glu Thr Gly Ala Ile Glu Ala Ala Leu Thr Thr Ile Asn
        355                 360                 365

Ser Val Leu Ser Ala Ala Ser Ala Gly Val Gly Ala Ala Ala Thr Gly
    370                 375                 380

Ser Leu Val Gly Ala Pro Val Ala Ala Leu Val Ser Ala Ile Thr Gly
385                 390                 395                 400

Ile Ile Ser Gly Ile Leu Asp Ala Ser Lys Gln Ala Ile Phe Glu Arg
                405                 410                 415

Val Ala Thr Lys Leu Ala Asn Lys Ile Asp Glu Trp Glu Lys Lys His
            420                 425                 430

Gly Lys Asn Tyr Phe Glu Asn Gly Tyr Asp Ala Arg His Ser Ala Phe
        435                 440                 445

Leu Glu Asp Thr Phe Glu Leu Leu Ser Gln Tyr Asn Lys Glu Tyr Ser
    450                 455                 460

Val Glu Arg Val Val Ala Ile Thr Gln Gln Arg Trp Asp Val Asn Ile
465                 470                 475                 480

Gly Glu Leu Ala Gly Ile Thr Arg Lys Gly Ser Asp Thr Lys Ser Gly
                485                 490                 495

Lys Ala Tyr Val Asp Phe Phe Glu Glu Gly Lys Leu Leu Glu Lys Glu
            500                 505                 510

Pro Asp Arg Phe Asp Lys Lys Val Lys Asp Pro Leu Glu Gly Lys Ile
        515                 520                 525
```

-continued

```
Asp Leu Ser Ser Ile Asn Lys Thr Thr Leu Leu Lys Phe Val Thr Pro
    530                 535                 540

Val Phe Thr Ala Gly Glu Glu Ile Arg Glu Arg Lys Gln Thr Gly Lys
545                 550                 555                 560

Tyr Glu Tyr Met Thr Glu Leu Phe Val Lys Gly Lys Glu Lys Trp Val
                565                 570                 575

Val Thr Gly Val Gln Ser His Asn Ala Ile Tyr Asp Tyr Thr Asn Leu
            580                 585                 590

Ile Gln Leu Ala Ile Asp Lys Lys Gly Glu Lys Arg Gln Val Thr Ile
        595                 600                 605

Glu Ser His Leu Gly Glu Lys Asn Asp Arg Ile Tyr Leu Ser Ser Gly
    610                 615                 620

Ser Ser Ile Val Tyr Ala Gly Asn Gly His Asp Val Ala Tyr Tyr Asp
625                 630                 635                 640

Lys Thr Asp Thr Gly Tyr Leu Thr Phe Asp Gly Gln Ser Ala Gln Lys
                645                 650                 655

Ala Gly Glu Tyr Ile Val Thr Lys Glu Leu Lys Ala Asp Val Lys Val
            660                 665                 670

Leu Lys Glu Val Val Lys Thr Gln Asp Ile Ser Val Gly Lys Arg Ser
        675                 680                 685

Glu Lys Leu Glu Tyr Arg Asp Tyr Glu Leu Ser Pro Phe Glu Leu Gly
    690                 695                 700

Asn Gly Ile Arg Ala Lys Asp Glu Leu His Ser Val Glu Glu Ile Ile
705                 710                 715                 720

Gly Ser Asn Arg Lys Asp Lys Phe Phe Gly Ser Arg Phe Thr Asp Ile
                725                 730                 735

Phe His Gly Ala Lys Gly Asp Asp Glu Ile Tyr Gly Asn Asp Gly His
            740                 745                 750

Asp Ile Leu Tyr Gly Asp Asp Gly Asn Asp Val Ile His Gly Gly Asp
        755                 760                 765

Gly Asn Asp His Leu Val Gly Gly Asn Gly Asn Asp Arg Leu Ile Gly
    770                 775                 780

Gly Lys Gly Asn Asn Phe Leu Asn Gly Gly Asp Gly Asp Asp Glu Leu
785                 790                 795                 800

Gln Val Phe Glu Gly Gln Tyr Asn Val Leu Leu Gly Gly Ala Gly Asn
                805                 810                 815

Asp Ile Leu Tyr Gly Ser Asp Gly Thr Asn Leu Phe Asp Gly Gly Val
            820                 825                 830

Gly Asn Asp Lys Ile Tyr Gly Gly Leu Gly Lys Asp Ile Tyr Arg Tyr
        835                 840                 845

Ser Lys Glu Tyr Gly Arg His Ile Ile Ile Glu Lys Gly Gly Asp Asp
    850                 855                 860

Asp Thr Leu Leu Leu Ser Asp Leu Ser Phe Lys Asp Val Gly Phe Ile
865                 870                 875                 880

Arg Ile Gly Asp Asp Leu Leu Val Asn Lys Arg Ile Gly Gly Thr Leu
                885                 890                 895

Tyr Tyr His Glu Asp Tyr Asn Gly Asn Ala Leu Thr Ile Lys Asp Trp
            900                 905                 910

Phe Lys Glu Gly Lys Glu Gly Gln Asn Asn Lys Ile Glu Lys Ile Val
        915                 920                 925

Asp Lys Asp Gly Ala Tyr Val Leu Ser Gln Tyr Leu Thr Glu Leu Thr
    930                 935                 940

Ala Pro Gly Arg Gly Ile Asn Tyr Phe Asn Gly Leu Glu Glu Lys Leu
```

-continued

```
945                 950                 955                 960

Tyr Tyr Gly Glu Gly Tyr Asn Ala Leu Pro Gln Leu Arg Lys Asp Ile
                965                 970                 975

Glu Gln Ile Ile Ser Ser Thr Gly Ala Phe Thr Gly Asp His Gly Lys
            980                 985                 990

Val Ser Val Gly Ser Gly Gly Pro Leu Val Tyr Asn Asn Ser Ala Asn
        995                 1000                1005

Asn Val Ala Ile Leu
    1010


<210> SEQ ID NO 4
<211> LENGTH: 707
<212> TYPE: PRT
<213> ORGANISM: Actinobacillus pleuropneumonia

<400> SEQUENCE: 4

Met Asp Phe Tyr Arg Glu Glu Asp Tyr Gly Leu Tyr Ala Leu Thr Ile
 1               5                  10                  15

Leu Ala Gln Tyr His Asn Ile Ala Val Asn Pro Glu Glu Leu Lys His
            20                  25                  30

Lys Phe Asp Leu Glu Gly Lys Gly Leu Asp Leu Thr Ala Trp Leu Leu
        35                  40                  45

Ala Ala Lys Ser Leu Glu Leu Lys Ala Lys Gln Val Lys Lys Ala Ile
    50                  55                  60

Asp Arg Leu Ala Phe Ile Gly Leu Pro Ala Leu Val Trp Arg Glu Asp
65                  70                  75                  80

Gly Lys His Phe Ile Leu Thr Lys Ile Asp Asn Glu Ala Lys Lys Tyr
                85                  90                  95

Leu Ile Phe Asp Leu Glu Thr His Asn Pro Arg Ile Leu Glu Gln Ala
            100                 105                 110

Glu Phe Glu Ser Leu Tyr Gln Gly Lys Leu Ile Leu Val Ala Ser Arg
        115                 120                 125

Ala Ser Ile Val Gly Lys Leu Ala Lys Phe Asp Phe Thr Trp Phe Ile
    130                 135                 140

Pro Ala Val Ile Lys Tyr Arg Lys Ile Phe Ile Glu Thr Leu Ile Val
145                 150                 155                 160

Ser Ile Phe Leu Gln Ile Phe Ala Leu Ile Thr Pro Leu Phe Phe Gln
                165                 170                 175

Val Val Met Asp Lys Val Leu Val His Arg Gly Phe Ser Thr Leu Asn
            180                 185                 190

Val Ile Thr Val Ala Leu Ala Ile Val Val Leu Phe Glu Ile Val Leu
        195                 200                 205

Asn Gly Leu Arg Thr Tyr Ile Phe Ala His Ser Thr Ser Arg Ile Asp
    210                 215                 220

Val Glu Leu Gly Ala Arg Leu Phe Arg His Leu Leu Ala Leu Pro Ile
225                 230                 235                 240

Ser Tyr Phe Glu Asn Arg Arg Val Gly Asp Thr Val Ala Arg Val Arg
                245                 250                 255

Glu Leu Asp Gln Ile Arg Asn Phe Leu Thr Gly Gln Ala Leu Thr Ser
            260                 265                 270

Val Leu Asp Leu Met Phe Ser Phe Ile Phe Phe Ala Val Met Trp Tyr
        275                 280                 285

Tyr Ser Pro Lys Leu Thr Leu Val Ile Leu Gly Ser Leu Pro Phe Tyr
    290                 295                 300
```

-continued

Met Gly Trp Ser Ile Phe Ile Ser Pro Ile Leu Arg Arg Arg Leu Asp
305 310 315 320

Glu Lys Phe Ala Arg Gly Ala Asp Asn Gln Ser Phe Leu Val Glu Ser
325 330 335

Val Thr Ala Ile Asn Thr Ile Lys Ala Leu Ala Val Thr Pro Gln Met
340 345 350

Thr Asn Thr Trp Asp Lys Gln Leu Ala Ser Tyr Val Ser Ala Gly Phe
355 360 365

Arg Val Thr Thr Leu Ala Thr Ile Gly Gln Gln Gly Val Gln Phe Ile
370 375 380

Gln Lys Val Val Met Val Ile Thr Leu Trp Leu Gly Ala His Leu Val
385 390 395 400

Ile Ser Gly Asp Leu Ser Ile Gly Gln Leu Ile Ala Phe Asn Met Leu
405 410 415

Ser Gly Gln Val Ile Ala Pro Val Ile Arg Leu Ala Gln Leu Trp Gln
420 425 430

Asp Phe Gln Gln Val Gly Ile Ser Val Thr Arg Leu Gly Asp Val Leu
435 440 445

Asn Ser Pro Thr Glu Ser Tyr Gln Gly Lys Leu Ala Leu Pro Glu Ile
450 455 460

Lys Gly Asp Ile Thr Phe Arg Asn Ile Arg Phe Arg Tyr Lys Pro Asp
465 470 475 480

Ala Pro Leu Ile Leu Asn Asp Val Asn Leu Ser Ile Gln Gln Gly Glu
485 490 495

Val Ile Gly Ile Val Gly Arg Ser Gly Ser Gly Lys Ser Thr Leu Thr
500 505 510

Lys Leu Ile Gln Arg Phe Tyr Ile Pro Glu Asn Gly Gln Val Leu Ile
515 520 525

Asp Gly His Asp Leu Ala Leu Ala Asp Pro Asn Trp Leu Arg Arg Gln
530 535 540

Val Gly Val Val Leu Gln Asp Asn Val Leu Leu Asn Arg Ser Ile Arg
545 550 555 560

Asp Asn Ile Ala Leu Ala Asp Pro Gly Met Pro Met Glu Lys Ile Val
565 570 575

His Ala Ala Lys Leu Ala Gly Ala His Glu Phe Ile Ser Glu Leu Arg
580 585 590

Glu Gly Tyr Asn Thr Ile Val Gly Glu Gln Gly Ala Gly Leu Ser Gly
595 600 605

Gly Gln Arg Gln Arg Ile Ala Ile Ala Arg Ala Leu Val Asn Asn Pro
610 615 620

Lys Ile Leu Ile Phe Asp Glu Ala Thr Ser Ala Leu Asp Tyr Glu Ser
625 630 635 640

Glu His Ile Ile Met Arg Asn Met His Gln Ile Cys Lys Gly Arg Thr
645 650 655

Val Ile Ile Ile Ala His Arg Leu Ser Thr Val Lys Asn Ala Asp Arg
660 665 670

Ile Ile Val Met Glu Lys Gly Gln Ile Val Glu Gln Gly Lys His Lys
675 680 685

Glu Leu Leu Ala Asp Pro Asn Gly Leu Tyr His Tyr Leu His Gln Leu
690 695 700

Gln Ser Glu
705

-continued

<210> SEQ ID NO 5
<211> LENGTH: 478
<212> TYPE: PRT
<213> ORGANISM: Actinobacillus pleuropneumonia

<400> SEQUENCE: 5

```
Met Lys Thr Trp Leu Met Gly Leu Tyr Glu Phe Phe Gln Arg Tyr Lys
 1               5                  10                  15

Thr Val Trp Thr Glu Ile Trp Lys Ile Arg His Gln Leu Asp Thr Pro
            20                  25                  30

Asp Arg Glu Lys Asp Glu Asn Glu Phe Leu Pro Ala His Leu Glu Leu
        35                  40                  45

Ile Glu Thr Pro Val Ser Lys Lys Pro Arg Leu Ile Ala Tyr Leu Ile
    50                  55                  60

Met Leu Phe Leu Phe Leu Ala Leu Val Ile Ser Ile Val Ser His Val
65                  70                  75                  80

Glu Ile Val Ala Thr Ala Thr Gly Lys Leu Ala Phe Ser Asp Arg Ser
                85                  90                  95

Lys Glu Ile Lys Pro Ile Glu Asn Ala Leu Val Lys Glu Ile Phe Val
            100                 105                 110

Gln Asp Gly Gln Phe Val Glu Lys Asp Gln Leu Leu Leu His Leu Thr
        115                 120                 125

Ala Leu Gly Ala Asp Ala Asp Gln Gln Lys Thr Lys Ser Ser Leu Ser
    130                 135                 140

Leu Thr Lys Leu Glu Arg Tyr Arg Tyr Glu Ile Leu Leu Glu Ala Val
145                 150                 155                 160

Ala Ala Asp Arg Leu Pro Leu Ile Glu Leu Thr Lys Asp Glu Phe Lys
                165                 170                 175

His Ala Thr Glu Glu Asp Lys Thr Arg Ile Arg Tyr Leu Ile Thr Glu
            180                 185                 190

Gln Phe Glu Ala Trp Gln Lys Gln Lys Tyr Gln Lys Glu Leu Ala Leu
        195                 200                 205

Gln Arg Arg Glu Ala Glu Lys Gln Thr Val Leu Ala Asn Ile Arg Lys
    210                 215                 220

Tyr Glu Gly Ile Ser Arg Val Glu Asn Glu Arg Leu Lys Asp Leu Lys
225                 230                 235                 240

Lys Leu Phe Asn Ser Lys Ser Thr Ser Lys His Asp Val Leu Thr Gln
                245                 250                 255

Glu Asn Arg His Ile Glu Ala Val Asn Glu Leu Ala Val Tyr Lys Ser
            260                 265                 270

Arg Leu Asn Glu Val Glu Ser Asp Leu Arg Gln Ala Lys Glu Glu Ile
        275                 280                 285

His Leu Ile Thr Gln Leu Phe Arg Ala Asp Ile Leu Glu Lys Leu Lys
    290                 295                 300

Gln Asn Val Glu Ala Glu Lys Gln Leu Ser Leu Glu Leu Glu Lys Asn
305                 310                 315                 320

Glu Gln Arg Gln Ile Ala Ser Val Ile Arg Ala Pro Val Ser Gly Thr
                325                 330                 335

Val Gln Gln Leu Lys Thr His Thr Val Gly Gly Val Val Thr Thr Ala
            340                 345                 350

Glu Thr Leu Met Val Ile Ala Pro Glu Asp Asp Val Leu Glu Val Thr
        355                 360                 365

Ala Leu Ile Gln Asn Lys Asp Ile Gly Phe Ile Glu Val Gly Gln Asp
    370                 375                 380
```

-continued

Ala Val Ile Lys Val Glu Thr Phe Pro Tyr Thr Arg Tyr Gly Tyr Leu
385 390 395 400

Met Gly Lys Val Lys Asn Ile Thr Leu Glu Ala Ile Glu His Pro Gln
405 410 415

Leu Gly Leu Ile Phe Asn Ser Ile Ile Ser Ile Asp Arg Lys Thr Leu
420 425 430

Ser Gly Lys Asp Gly Lys Glu Ile Glu Leu Gly Ser Gly Met Ser Val
435 440 445

Thr Ala Glu Ile Lys Thr Gly Glu Arg Ser Val Ile Ser Tyr Leu Leu
450 455 460

Ser Pro Leu Glu Glu Ser Val Ser Glu Ser Leu Arg Glu Arg
465 470 475

<210> SEQ ID NO 6
<211> LENGTH: 4731
<212> TYPE: DNA
<213> ORGANISM: Actinobacillus pleuropneumonia
<220> FEATURE:
<221> NAME/KEY: CDS
<222> LOCATION: (233)...(709)
<221> NAME/KEY: CDS
<222> LOCATION: (751)...(3618)

<400> SEQUENCE: 6
cttaaccatt acagaacgtt ggtacaaaaa attttacagg aaaatgatgg atagtcctta 60
acaaaaatta atgttttatt tcctataaaa catccgacca gtattatttt tgattaaaaa 120
aagaacaaac agatcatgac aaacgtttgc cttgttttcc ttcacaaaaa tattatggtt 180
ttttatttag aataaattat ctatattcat tttttaggga atgggaggga tg atg cta 238
Met Leu
1 aaa aat gat ttt aac gta ttg gga caa att gct tgg tta tgg gca aat 286
Lys Asn Asp Phe Asn Val Leu Gly Gln Ile Ala Trp Leu Trp Ala Asn
5 10 15 tct cca atg cac cga aat tgg tca gtt tca ctg tta atg aag aat gtt 334
Ser Pro Met His Arg Asn Trp Ser Val Ser Leu Leu Met Lys Asn Val
20 25 30 att cct gca att gaa aat gac caa tat ttg tta cta gtt gat gat ggt 382
Ile Pro Ala Ile Glu Asn Asp Gln Tyr Leu Leu Leu Val Asp Asp Gly
35 40 45 50 ttt cct att gca tat tgc agt tgg gcc aaa tta act cta gag agt gag 430
Phe Pro Ile Ala Tyr Cys Ser Trp Ala Lys Leu Thr Leu Glu Ser Glu
55 60 65 gct cgc tat gta aag gac acc aat tca tta aaa ata gat gat tgg aat 478
Ala Arg Tyr Val Lys Asp Thr Asn Ser Leu Lys Ile Asp Asp Trp Asn
70 75 80 gca gga gat cgt ata tgg atc att gat tgg att gcc cca ttc ggg gat 526
Ala Gly Asp Arg Ile Trp Ile Ile Asp Trp Ile Ala Pro Phe Gly Asp
85 90 95 tca tct cta ttg tat aaa cat atg aga caa cgt ttt cca tac gat att 574
Ser Ser Leu Leu Tyr Lys His Met Arg Gln Arg Phe Pro Tyr Asp Ile
100 105 110 gga agg gca att aga atc tat cct agc aaa aaa gat act gga aaa atc 622
Gly Arg Ala Ile Arg Ile Tyr Pro Ser Lys Lys Asp Thr Gly Lys Ile
115 120 125 130 ata tat tta aaa gga gga aaa ata aca aaa aaa gta gct gaa aag aca 670
Ile Tyr Leu Lys Gly Gly Lys Ile Thr Lys Lys Val Ala Glu Lys Thr
135 140 145 ttt ctt cag tat gag caa gag tta ata aca gct cta caa taatatcttt 719
Phe Leu Gln Tyr Glu Gln Glu Leu Ile Thr Ala Leu Gln
150 155

-continued

```
aaatgatcaa ttatataaag gagactcttt t atg tca aaa atc act ttg tca       771
                                   Met Ser Lys Ile Thr Leu Ser
                                   160                 165

tca tta aaa tcg tcc tta caa caa gga ttg aaa aat ggg aaa aac aag       819
Ser Leu Lys Ser Ser Leu Gln Gln Gly Leu Lys Asn Gly Lys Asn Lys
            170                 175                 180

tta aat caa gca ggt aca aca ctg aag aat ggt tta act caa act ggt       867
Leu Asn Gln Ala Gly Thr Thr Leu Lys Asn Gly Leu Thr Gln Thr Gly
        185                 190                 195

cat tct cta cag aat ggg gct aaa aaa tta atc tta tat att cct caa       915
His Ser Leu Gln Asn Gly Ala Lys Lys Leu Ile Leu Tyr Ile Pro Gln
    200                 205                 210

ggc tat gat tcg ggt caa gga aat gga gtt caa gat tta gtt aaa gct       963
Gly Tyr Asp Ser Gly Gln Gly Asn Gly Val Gln Asp Leu Val Lys Ala
215                 220                 225                 230

gct aat gat tta ggt att gaa gta tgg cga gaa gaa cgc agc aat ttg      1011
Ala Asn Asp Leu Gly Ile Glu Val Trp Arg Glu Glu Arg Ser Asn Leu
            235                 240                 245

gac att gca aaa act agc ttt gat aca act cag aaa att cta ggt ttt      1059
Asp Ile Ala Lys Thr Ser Phe Asp Thr Thr Gln Lys Ile Leu Gly Phe
            250                 255                 260

act gat aga gga att gta tta ttt gca cct cag cta gat aat tta tta      1107
Thr Asp Arg Gly Ile Val Leu Phe Ala Pro Gln Leu Asp Asn Leu Leu
        265                 270                 275

aag aag aat cct aaa att ggc aat aca tta gga agt gct tct agc atc      1155
Lys Lys Asn Pro Lys Ile Gly Asn Thr Leu Gly Ser Ala Ser Ser Ile
    280                 285                 290

tca caa aat ata ggt aaa gcc aat act gta tta ggt ggt att caa tct      1203
Ser Gln Asn Ile Gly Lys Ala Asn Thr Val Leu Gly Gly Ile Gln Ser
295                 300                 305                 310

att tta gga tct gtt tta tct gga gta aat ctg aat gaa tta ctt caa      1251
Ile Leu Gly Ser Val Leu Ser Gly Val Asn Leu Asn Glu Leu Leu Gln
            315                 320                 325

aat aaa gat cct aat caa tta gaa ctt gca aaa gca ggg cta gaa ctg      1299
Asn Lys Asp Pro Asn Gln Leu Glu Leu Ala Lys Ala Gly Leu Glu Leu
            330                 335                 340

act aat gaa tta gtt ggt aat att gct agc tcg gtg caa act gta gat      1347
Thr Asn Glu Leu Val Gly Asn Ile Ala Ser Ser Val Gln Thr Val Asp
        345                 350                 355

gca ttt gca gaa caa ata tct aaa cta ggt tca cat tta cag aat gtg      1395
Ala Phe Ala Glu Gln Ile Ser Lys Leu Gly Ser His Leu Gln Asn Val
    360                 365                 370

aaa gga tta gga gga ttg agt aat aaa tta caa aat cta cca gat cta      1443
Lys Gly Leu Gly Gly Leu Ser Asn Lys Leu Gln Asn Leu Pro Asp Leu
375                 380                 385                 390

gga aaa gca agt tta ggt ttg gac att atc tct ggt tta ctt tct gga      1491
Gly Lys Ala Ser Leu Gly Leu Asp Ile Ile Ser Gly Leu Leu Ser Gly
            395                 400                 405

gca tct gca ggt ctc att tta gca gat aaa gag gct tca aca gaa aag      1539
Ala Ser Ala Gly Leu Ile Leu Ala Asp Lys Glu Ala Ser Thr Glu Lys
            410                 415                 420

aaa gct gcc gca ggt gta gaa ttt gct aac caa att ata ggt aat gta      1587
Lys Ala Ala Ala Gly Val Glu Phe Ala Asn Gln Ile Ile Gly Asn Val
        425                 430                 435

aca aaa gcg gtc tca tct tac att ctt gcc caa cga gtc gct tca ggt      1635
Thr Lys Ala Val Ser Ser Tyr Ile Leu Ala Gln Arg Val Ala Ser Gly
    440                 445                 450

ttg tct tca act ggt cct gtc gct gca tta atc gca tct aca gtt gca      1683
Leu Ser Ser Thr Gly Pro Val Ala Ala Leu Ile Ala Ser Thr Val Ala
```

-continued

```
455                 460                 465                 470

cta gct gtt agc cct ctt tca ttc tta aat gta gct gat aag ttt aaa     1731
Leu Ala Val Ser Pro Leu Ser Phe Leu Asn Val Ala Asp Lys Phe Lys
            475                 480                 485

caa gct gat tta atc aaa tca tat tct gaa cgc ttc caa aaa tta gga     1779
Gln Ala Asp Leu Ile Lys Ser Tyr Ser Glu Arg Phe Gln Lys Leu Gly
            490                 495                 500

tat gat gga gat cgt tta tta gct gat ttt cac cgt gag aca gga act     1827
Tyr Asp Gly Asp Arg Leu Leu Ala Asp Phe His Arg Glu Thr Gly Thr
        505                 510                 515

att gat gct tct gta aca aca att aac act gct tta gca gct atc tcc     1875
Ile Asp Ala Ser Val Thr Thr Ile Asn Thr Ala Leu Ala Ala Ile Ser
    520                 525                 530

ggt gga gtt gga gct gca agc gcg ggt tct cta gtc gga gct cca gtt     1923
Gly Gly Val Gly Ala Ala Ser Ala Gly Ser Leu Val Gly Ala Pro Val
535                 540                 545                 550

gcg tta ctc gtt gct ggt gtt acg gga ctt att aca act att cta gaa     1971
Ala Leu Leu Val Ala Gly Val Thr Gly Leu Ile Thr Thr Ile Leu Glu
            555                 560                 565

tat tct aaa caa gcc atg ttt gaa cat gtt gca aat aag gtt cat gac     2019
Tyr Ser Lys Gln Ala Met Phe Glu His Val Ala Asn Lys Val His Asp
            570                 575                 580

aga ata gtt gaa tgg gag aaa aaa cat aat aaa aac tat ttt gag caa     2067
Arg Ile Val Glu Trp Glu Lys Lys His Asn Lys Asn Tyr Phe Glu Gln
        585                 590                 595

ggt tat gat tct cgt cat tta gct gat tta caa gac aat atg aag ttt     2115
Gly Tyr Asp Ser Arg His Leu Ala Asp Leu Gln Asp Asn Met Lys Phe
    600                 605                 610

ctt atc aat tta aat aaa gaa ctt cag gct gaa cgc gta gta gct att     2163
Leu Ile Asn Leu Asn Lys Glu Leu Gln Ala Glu Arg Val Val Ala Ile
615                 620                 625                 630

acc caa caa aga tgg gat aac caa att gga gac cta gcg gca att agc     2211
Thr Gln Gln Arg Trp Asp Asn Gln Ile Gly Asp Leu Ala Ala Ile Ser
            635                 640                 645

cgt aga acg gat aaa att tcc agt gga aaa gct tat gtg gat gct ttt     2259
Arg Arg Thr Asp Lys Ile Ser Ser Gly Lys Ala Tyr Val Asp Ala Phe
            650                 655                 660

gag gag ggg caa cac cag tcc tac gat tca tcc gta cag cta gat aac     2307
Glu Glu Gly Gln His Gln Ser Tyr Asp Ser Ser Val Gln Leu Asp Asn
        665                 670                 675

aaa aac ggt att att aat att agt aat aca aat aga aag aca caa agt     2355
Lys Asn Gly Ile Ile Asn Ile Ser Asn Thr Asn Arg Lys Thr Gln Ser
    680                 685                 690

gtt tta ttc aga act cca tta cta act cca ggt gaa gag aat cgg gaa     2403
Val Leu Phe Arg Thr Pro Leu Leu Thr Pro Gly Glu Glu Asn Arg Glu
695                 700                 705                 710

cgt att cag gaa ggt aaa aat tct tat att aca aaa tta cat ata caa     2451
Arg Ile Gln Glu Gly Lys Asn Ser Tyr Ile Thr Lys Leu His Ile Gln
            715                 720                 725

aga gtt gac agt tgg act gta aca gat ggt gat gct agc tca agc gta     2499
Arg Val Asp Ser Trp Thr Val Thr Asp Gly Asp Ala Ser Ser Ser Val
            730                 735                 740

gat ttc act aat gta gta caa cga atc gct gtg aaa ttt gat gat gca     2547
Asp Phe Thr Asn Val Val Gln Arg Ile Ala Val Lys Phe Asp Asp Ala
        745                 750                 755

ggt aac att ata gaa tct aaa gat act aaa att atc gca aat tta ggt     2595
Gly Asn Ile Ile Glu Ser Lys Asp Thr Lys Ile Ile Ala Asn Leu Gly
    760                 765                 770

gct ggt aac gat aat gta ttt gtt ggg tca agt act acc gtt att gat     2643
```

-continued

```
Ala Gly Asn Asp Asn Val Phe Val Gly Ser Ser Thr Thr Val Ile Asp
775                 780                 785                 790

ggc ggg gac gga cat gat cga gtt cac tac agt aga gga gaa tat ggc      2691
Gly Gly Asp Gly His Asp Arg Val His Tyr Ser Arg Gly Glu Tyr Gly
                795                 800                 805

gca tta gtt att gat gct aca gcc gag aca gaa aaa ggc tca tat tca      2739
Ala Leu Val Ile Asp Ala Thr Ala Glu Thr Glu Lys Gly Ser Tyr Ser
            810                 815                 820

gta aaa cgc tat gtc gga gac agt aaa gca tta cat gaa aca att gcc      2787
Val Lys Arg Tyr Val Gly Asp Ser Lys Ala Leu His Glu Thr Ile Ala
        825                 830                 835

acc cac caa aca aat gtt ggt aat cgt gaa gaa aaa att gaa tat cgt      2835
Thr His Gln Thr Asn Val Gly Asn Arg Glu Glu Lys Ile Glu Tyr Arg
    840                 845                 850

cgt gaa gat gat cgt ttt cat act ggt tat act gtg acg gac tca ctc      2883
Arg Glu Asp Asp Arg Phe His Thr Gly Tyr Thr Val Thr Asp Ser Leu
855                 860                 865                 870

aaa tca gtt gaa gag atc att ggt tca caa ttt aat gat att ttc aaa      2931
Lys Ser Val Glu Glu Ile Ile Gly Ser Gln Phe Asn Asp Ile Phe Lys
                875                 880                 885

gga agc caa ttt gat gat gtg ttc cat ggt ggt aat ggt gta gac act      2979
Gly Ser Gln Phe Asp Asp Val Phe His Gly Gly Asn Gly Val Asp Thr
            890                 895                 900

att gat ggt aac gat ggt gac gat cat tta ttt ggt ggc gca ggc gat      3027
Ile Asp Gly Asn Asp Gly Asp Asp His Leu Phe Gly Gly Ala Gly Asp
        905                 910                 915

gat gtt atc gat gga gga aac ggt aac aat ttc ctt gtt gga gga acc      3075
Asp Val Ile Asp Gly Gly Asn Gly Asn Asn Phe Leu Val Gly Gly Thr
    920                 925                 930

ggt aat gat att atc tcg gga ggt aaa gat aat gat att tat gtc cat      3123
Gly Asn Asp Ile Ile Ser Gly Gly Lys Asp Asn Asp Ile Tyr Val His
935                 940                 945                 950

aaa aca ggc gat gga aat gat tct att aca gac tct ggc gga caa gat      3171
Lys Thr Gly Asp Gly Asn Asp Ser Ile Thr Asp Ser Gly Gly Gln Asp
                955                 960                 965

aaa ctg gca ttt tcg gat gta aat ctt aaa gac ctc acc ttt aag aaa      3219
Lys Leu Ala Phe Ser Asp Val Asn Leu Lys Asp Leu Thr Phe Lys Lys
            970                 975                 980

gta gat tct tct ctc gaa atc att aat caa aaa gga gaa aaa gtt cgt      3267
Val Asp Ser Ser Leu Glu Ile Ile Asn Gln Lys Gly Glu Lys Val Arg
        985                 990                 995

att ggg aat tgg ttc tta gaa gat gat ttg gct agc aca gtt gct aac      3315
Ile Gly Asn Trp Phe Leu Glu Asp Asp Leu Ala Ser Thr Val Ala Asn
    1000                1005                1010

tat aaa gct acg aat gac cga aaa att gag gaa att att ggt aaa gga      3363
Tyr Lys Ala Thr Asn Asp Arg Lys Ile Glu Glu Ile Ile Gly Lys Gly
1015                1020                1025                1030

gga gaa cgt att aca tca gaa caa gtt gat aaa ctg att aag gag ggt      3411
Gly Glu Arg Ile Thr Ser Glu Gln Val Asp Lys Leu Ile Lys Glu Gly
                1035                1040                1045

aac aat caa atc tct gca gaa gca tta tcc aaa gtt gtg aat gat tac      3459
Asn Asn Gln Ile Ser Ala Glu Ala Leu Ser Lys Val Val Asn Asp Tyr
            1050                1055                1060

aat acg agt aaa gat aga cag aac gta tct aat agc tta gca aaa ttg      3507
Asn Thr Ser Lys Asp Arg Gln Asn Val Ser Asn Ser Leu Ala Lys Leu
        1065                1070                1075

att tct tca gtc ggg agc ttt acg tct tcc tca gac ttt agg aat aat      3555
Ile Ser Ser Val Gly Ser Phe Thr Ser Ser Ser Asp Phe Arg Asn Asn
    1080                1085                1090
```

-continued

```
tta gga aca tat gtt cct tca tca ata gat gtc tcg aat aat att caa     3603
Leu Gly Thr Tyr Val Pro Ser Ser Ile Asp Val Ser Asn Asn Ile Gln
1095                1100                1105                1110

tta gct aga gcc gct taatattcaa atcatagcaa tcctatggtg taaattatag     3658
Leu Ala Arg Ala Ala
                1115

gattgttatt tttttaaagg agaagttatg gaacccaata aaaataagga tcttggttta   3718

gctgtagaaa atcaaaccta atctgacagt tcccgtttaa aattaccgtg tctgtcagat   3778

taatttgagc ttaaattctt ttctgcccaa atccgttttc catcaagtaa tgttgccatc   3838

ggtgttctgc cacagcacac ttttccttga tgtgttcgat ggtgattata atacattcat   3898

ctaaatcagc ttgtaatgtc gctaaatccg tatatatttt cttcctaaat gcgacttggt   3958

aaaattcttg taagatagtc ttatgaaaac gttcacagat accattcgtc tgtggatgct   4018

tcactttcgt tttagtatgc tctatgtcat ttatcgctaa ataaagctca taatcgtgat   4078

tttccacttt gccacaatat tcactgccac ggtcggtgag aatacgcaac atcggtaatc   4138

cttgggcttc aaagaacggc agtactttat gattgagcat atctgcagcg gcaattgcgg   4198

ttttcattgt gtagagcttt gcaaaagcaa ccttactata agtatcaaca aatgtttgct   4258

gataaatgcg tccaacacct tttaaattac ctacataaaa ggtatcttgt gaacctaaat   4318

agcccggatg agcggtttca atttctccac tcgatatatc atcctctttc ttacgttcta   4378

gggcttggac ttgactttca tttagaataa tgcctttctc agccacttct ttctctagtg   4438

catttaaacg ctgtttaaag ttagtaagat tatgacgtag ccaaatggaa cgaacaccac   4498

cggctgaaac aaacacacct tgcttgcgaa gttcgttact cactcgaact tgtccgtaag   4558

ctggaaaatc tagagcaaat tttacaacag cttgctcaat gtgctcgtct actcgatttt   4618

tgatattcgg tacccgacga gtttgcttaa gtaatgcttc aacaccgcct tgcgctacgg   4678

cttgttgata gcgatagaat gtatctcggc tcattcccat cgctttacaa gct          4731


<210> SEQ ID NO 7
<211> LENGTH: 159
<212> TYPE: PRT
<213> ORGANISM: Actinobacillus pleuropneumonia

<400> SEQUENCE: 7

Met Leu Lys Asn Asp Phe Asn Val Leu Gly Gln Ile Ala Trp Leu Trp
 1               5                  10                  15

Ala Asn Ser Pro Met His Arg Asn Trp Ser Val Ser Leu Leu Met Lys
            20                  25                  30

Asn Val Ile Pro Ala Ile Glu Asn Asp Gln Tyr Leu Leu Leu Val Asp
        35                  40                  45

Asp Gly Phe Pro Ile Ala Tyr Cys Ser Trp Ala Lys Leu Thr Leu Glu
    50                  55                  60

Ser Glu Ala Arg Tyr Val Lys Asp Thr Asn Ser Leu Lys Ile Asp Asp
65                  70                  75                  80

Trp Asn Ala Gly Asp Arg Ile Trp Ile Ile Asp Trp Ile Ala Pro Phe
                85                  90                  95

Gly Asp Ser Ser Leu Leu Tyr Lys His Met Arg Gln Arg Phe Pro Tyr
            100                 105                 110

Asp Ile Gly Arg Ala Ile Arg Ile Tyr Pro Ser Lys Lys Asp Thr Gly
        115                 120                 125

Lys Ile Ile Tyr Leu Lys Gly Gly Lys Ile Thr Lys Lys Val Ala Glu
    130                 135                 140
```

-continued

```
Lys Thr Phe Leu Gln Tyr Glu Gln Glu Leu Ile Thr Ala Leu Gln
145                 150                 155


<210> SEQ ID NO 8
<211> LENGTH: 956
<212> TYPE: PRT
<213> ORGANISM: Actinobacillus pleuropneumonia

<400> SEQUENCE: 8

Met Ser Lys Ile Thr Leu Ser Ser Leu Lys Ser Ser Leu Gln Gln Gly
 1               5                  10                  15

Leu Lys Asn Gly Lys Asn Lys Leu Asn Gln Ala Gly Thr Thr Leu Lys
            20                  25                  30

Asn Gly Leu Thr Gln Thr Gly His Ser Leu Gln Asn Gly Ala Lys Lys
        35                  40                  45

Leu Ile Leu Tyr Ile Pro Gln Gly Tyr Asp Ser Gly Gln Gly Asn Gly
    50                  55                  60

Val Gln Asp Leu Val Lys Ala Ala Asn Asp Leu Gly Ile Glu Val Trp
65                  70                  75                  80

Arg Glu Glu Arg Ser Asn Leu Asp Ile Ala Lys Thr Ser Phe Asp Thr
                85                  90                  95

Thr Gln Lys Ile Leu Gly Phe Thr Asp Arg Gly Ile Val Leu Phe Ala
            100                 105                 110

Pro Gln Leu Asp Asn Leu Leu Lys Lys Asn Pro Lys Ile Gly Asn Thr
        115                 120                 125

Leu Gly Ser Ala Ser Ser Ile Ser Gln Asn Ile Gly Lys Ala Asn Thr
    130                 135                 140

Val Leu Gly Gly Ile Gln Ser Ile Leu Gly Ser Val Leu Ser Gly Val
145                 150                 155                 160

Asn Leu Asn Glu Leu Leu Gln Asn Lys Asp Pro Asn Gln Leu Glu Leu
                165                 170                 175

Ala Lys Ala Gly Leu Glu Leu Thr Asn Glu Leu Val Gly Asn Ile Ala
            180                 185                 190

Ser Ser Val Gln Thr Val Asp Ala Phe Ala Glu Gln Ile Ser Lys Leu
        195                 200                 205

Gly Ser His Leu Gln Asn Val Lys Gly Leu Gly Gly Leu Ser Asn Lys
    210                 215                 220

Leu Gln Asn Leu Pro Asp Leu Gly Lys Ala Ser Leu Gly Leu Asp Ile
225                 230                 235                 240

Ile Ser Gly Leu Leu Ser Gly Ala Ser Ala Gly Leu Ile Leu Ala Asp
                245                 250                 255

Lys Glu Ala Ser Thr Glu Lys Lys Ala Ala Ala Gly Val Glu Phe Ala
            260                 265                 270

Asn Gln Ile Ile Gly Asn Val Thr Lys Ala Val Ser Ser Tyr Ile Leu
        275                 280                 285

Ala Gln Arg Val Ala Ser Gly Leu Ser Ser Thr Gly Pro Val Ala Ala
    290                 295                 300

Leu Ile Ala Ser Thr Val Ala Leu Ala Val Ser Pro Leu Ser Phe Leu
305                 310                 315                 320

Asn Val Ala Asp Lys Phe Lys Gln Ala Asp Leu Ile Lys Ser Tyr Ser
                325                 330                 335

Glu Arg Phe Gln Lys Leu Gly Tyr Asp Gly Asp Arg Leu Leu Ala Asp
            340                 345                 350

Phe His Arg Glu Thr Gly Thr Ile Asp Ala Ser Val Thr Thr Ile Asn
        355                 360                 365
```

-continued

```
Thr Ala Leu Ala Ala Ile Ser Gly Gly Val Gly Ala Ala Ser Ala Gly
    370                 375                 380

Ser Leu Val Gly Ala Pro Val Ala Leu Leu Val Ala Gly Val Thr Gly
385                 390                 395                 400

Leu Ile Thr Thr Ile Leu Glu Tyr Ser Lys Gln Ala Met Phe Glu His
                405                 410                 415

Val Ala Asn Lys Val His Asp Arg Ile Val Glu Trp Glu Lys Lys His
            420                 425                 430

Asn Lys Asn Tyr Phe Glu Gln Gly Tyr Asp Ser Arg His Leu Ala Asp
        435                 440                 445

Leu Gln Asp Asn Met Lys Phe Leu Ile Asn Leu Asn Lys Glu Leu Gln
    450                 455                 460

Ala Glu Arg Val Val Ala Ile Thr Gln Gln Arg Trp Asp Asn Gln Ile
465                 470                 475                 480

Gly Asp Leu Ala Ala Ile Ser Arg Arg Thr Asp Lys Ile Ser Ser Gly
                485                 490                 495

Lys Ala Tyr Val Asp Ala Phe Glu Glu Gly Gln His Gln Ser Tyr Asp
            500                 505                 510

Ser Ser Val Gln Leu Asp Asn Lys Asn Gly Ile Ile Asn Ile Ser Asn
        515                 520                 525

Thr Asn Arg Lys Thr Gln Ser Val Leu Phe Arg Thr Pro Leu Leu Thr
    530                 535                 540

Pro Gly Glu Glu Asn Arg Glu Arg Ile Gln Glu Gly Lys Asn Ser Tyr
545                 550                 555                 560

Ile Thr Lys Leu His Ile Gln Arg Val Asp Ser Trp Thr Val Thr Asp
                565                 570                 575

Gly Asp Ala Ser Ser Ser Val Asp Phe Thr Asn Val Val Gln Arg Ile
            580                 585                 590

Ala Val Lys Phe Asp Asp Ala Gly Asn Ile Ile Glu Ser Lys Asp Thr
        595                 600                 605

Lys Ile Ile Ala Asn Leu Gly Ala Gly Asn Asp Asn Val Phe Val Gly
    610                 615                 620

Ser Ser Thr Thr Val Ile Asp Gly Gly Asp Gly His Asp Arg Val His
625                 630                 635                 640

Tyr Ser Arg Gly Glu Tyr Gly Ala Leu Val Ile Asp Ala Thr Ala Glu
                645                 650                 655

Thr Glu Lys Gly Ser Tyr Ser Val Lys Arg Tyr Val Gly Asp Ser Lys
            660                 665                 670

Ala Leu His Glu Thr Ile Ala Thr His Gln Thr Asn Val Gly Asn Arg
        675                 680                 685

Glu Glu Lys Ile Glu Tyr Arg Arg Glu Asp Asp Arg Phe His Thr Gly
    690                 695                 700

Tyr Thr Val Thr Asp Ser Leu Lys Ser Val Glu Glu Ile Ile Gly Ser
705                 710                 715                 720

Gln Phe Asn Asp Ile Phe Lys Gly Ser Gln Phe Asp Asp Val Phe His
                725                 730                 735

Gly Gly Asn Gly Val Asp Thr Ile Asp Gly Asn Asp Gly Asp Asp His
            740                 745                 750

Leu Phe Gly Gly Ala Gly Asp Asp Val Ile Asp Gly Gly Asn Gly Asn
        755                 760                 765

Asn Phe Leu Val Gly Gly Thr Gly Asn Asp Ile Ile Ser Gly Gly Lys
    770                 775                 780
```

-continued

```
Asp Asn Asp Ile Tyr Val His Lys Thr Gly Asp Gly Asn Asp Ser Ile
785                 790                 795                 800

Thr Asp Ser Gly Gly Gln Asp Lys Leu Ala Phe Ser Asp Val Asn Leu
                805                 810                 815

Lys Asp Leu Thr Phe Lys Lys Val Asp Ser Ser Leu Glu Ile Ile Asn
            820                 825                 830

Gln Lys Gly Glu Lys Val Arg Ile Gly Asn Trp Phe Leu Glu Asp Asp
        835                 840                 845

Leu Ala Ser Thr Val Ala Asn Tyr Lys Ala Thr Asn Asp Arg Lys Ile
    850                 855                 860

Glu Glu Ile Ile Gly Lys Gly Gly Glu Arg Ile Thr Ser Glu Gln Val
865                 870                 875                 880

Asp Lys Leu Ile Lys Glu Gly Asn Asn Gln Ile Ser Ala Glu Ala Leu
                885                 890                 895

Ser Lys Val Val Asn Asp Tyr Asn Thr Ser Lys Asp Arg Gln Asn Val
            900                 905                 910

Ser Asn Ser Leu Ala Lys Leu Ile Ser Ser Val Gly Ser Phe Thr Ser
        915                 920                 925

Ser Ser Asp Phe Arg Asn Asn Leu Gly Thr Tyr Val Pro Ser Ser Ile
    930                 935                 940

Asp Val Ser Asn Asn Ile Gln Leu Ala Arg Ala Ala
945                 950                 955


<210> SEQ ID NO 9
<211> LENGTH: 4190
<212> TYPE: DNA
<213> ORGANISM: Actinobacillus pleuropneumonia
<220> FEATURE:
<221> NAME/KEY: CDS
<222> LOCATION: (716)...(3877)

<400> SEQUENCE: 9

gtagatattc ttttaatatc aaacaactat tgttatttgt ctgagtgtag atatgtagca      60

ttgtgtattt ctttatttac aactctaatc ttaatctaaa aagatttcta tattttcttt     120

gtaagaaatt ttgttaaaat ccgactaact atataattaa cggttcttaa agtggataaa     180

taataaaatt atgagttata aaaatgttaa aaatttaaca gatgatttta caactttagg     240

gcatatcgct tggttgtggg ctaattctcc gttacataag gagtggtcta tctctttgtt     300

tactaagaat attttgccag ccattcaaca tgatcaatat attttactta tgcgagatga     360

gttccctgta gcgttttgta gttgggcaaa tttaacgtta actaatgaag tgaagtatgt     420

acgtgatgtg acgtcattga cttttgaaga ttggaattca ggagaacgaa aatggttgat     480

cgactggatt gcgccatttg gggataacaa tacgctttat agatatatgc gtaaaaaatt     540

tcctaatgaa gtattccggg ccattcgagt atatcctggt tctacagaag cgaaaatcat     600

tcatgttcaa ggaggacaaa ttaataaatt tacagctaaa aaattaatac aacaatatca     660

ggaagaactt attcaagttc ttaacaatca caaaaaaatt gtaagaggat aaaat atg      718
                                                             Met
                                                              1
agt act tgg tca agc atg tta gcc gac tta aaa aaa ggg gct gaa gaa      766
Ser Thr Trp Ser Ser Met Leu Ala Asp Leu Lys Lys Gly Ala Glu Glu
            5                  10                  15

gcc aaa aga caa gcc aaa aaa ggc tac gat gta act aaa aat ggt ttg      814
Ala Lys Arg Gln Ala Lys Lys Gly Tyr Asp Val Thr Lys Asn Gly Leu
        20                  25                  30

caa tat ggg gtg agt caa gca aaa tta caa gca tta gga gct ggt aaa      862
Gln Tyr Gly Val Ser Gln Ala Lys Leu Gln Ala Leu Gly Ala Gly Lys
```

-continued

```
     35                  40                  45

gcc gtt caa aag tac ggt aat aaa tta gtt tta gtt att cca aaa gag      910
Ala Val Gln Lys Tyr Gly Asn Lys Leu Val Leu Val Ile Pro Lys Glu
 50                  55                  60                  65

tat gac gga agt gtt ggt aac ggt ttc ttt gat tta gta aaa gca gct      958
Tyr Asp Gly Ser Val Gly Asn Gly Phe Phe Asp Leu Val Lys Ala Ala
                 70                  75                  80

gag gaa tta ggc att caa gtt aaa tat gtt aac cgt aat gaa ttg gaa     1006
Glu Glu Leu Gly Ile Gln Val Lys Tyr Val Asn Arg Asn Glu Leu Glu
             85                  90                  95

gtt gcc cat aaa act tta ggt acc gca gac caa ttc ttg ggt tta aca     1054
Val Ala His Lys Thr Leu Gly Thr Ala Asp Gln Phe Leu Gly Leu Thr
        100                 105                 110

gaa cgt gga ctt act tta ttt gca ccg caa cta gat cag ttc tta caa     1102
Glu Arg Gly Leu Thr Leu Phe Ala Pro Gln Leu Asp Gln Phe Leu Gln
    115                 120                 125

aaa cat tca aaa att tct aac gta gtg ggc agt tct act ggt gat gca     1150
Lys His Ser Lys Ile Ser Asn Val Val Gly Ser Ser Thr Gly Asp Ala
130                 135                 140                 145

gta agt aaa ctt gct aag agt caa act att att tca gga att caa tct     1198
Val Ser Lys Leu Ala Lys Ser Gln Thr Ile Ile Ser Gly Ile Gln Ser
                150                 155                 160

gta tta ggt act gta tta gca ggt att aat ctt aat gaa gct att att     1246
Val Leu Gly Thr Val Leu Ala Gly Ile Asn Leu Asn Glu Ala Ile Ile
            165                 170                 175

agt ggc ggt tca gag ctc gaa tta gct gaa gct ggt gtt tct tta gcc     1294
Ser Gly Gly Ser Glu Leu Glu Leu Ala Glu Ala Gly Val Ser Leu Ala
        180                 185                 190

tct gag ctg ctt agt aat att gct aaa ggt aca aca aca ata gat gct     1342
Ser Glu Leu Leu Ser Asn Ile Ala Lys Gly Thr Thr Thr Ile Asp Ala
    195                 200                 205

ttc act aca caa atc cag aac ttt ggg aaa tta gtg gaa aat gct aaa     1390
Phe Thr Thr Gln Ile Gln Asn Phe Gly Lys Leu Val Glu Asn Ala Lys
210                 215                 220                 225

ggg tta ggt ggt gtt ggc cgc caa tta cag aat att tca ggt tct gca     1438
Gly Leu Gly Gly Val Gly Arg Gln Leu Gln Asn Ile Ser Gly Ser Ala
                230                 235                 240

tta agc aaa act gga tta ggt ttg gat att atc tca agc tta ctt tca     1486
Leu Ser Lys Thr Gly Leu Gly Leu Asp Ile Ile Ser Ser Leu Leu Ser
            245                 250                 255

gga gta act gca agt ttt gct tta gcg aat aag aat gct tca aca agc     1534
Gly Val Thr Ala Ser Phe Ala Leu Ala Asn Lys Asn Ala Ser Thr Ser
        260                 265                 270

act aaa gtt gct gct ggc ttt gaa ctc tca aat caa gta att ggt ggt     1582
Thr Lys Val Ala Ala Gly Phe Glu Leu Ser Asn Gln Val Ile Gly Gly
    275                 280                 285

att acg aaa gca gta tca agc tat att ctt gca cag cgt tta gct gct     1630
Ile Thr Lys Ala Val Ser Ser Tyr Ile Leu Ala Gln Arg Leu Ala Ala
290                 295                 300                 305

ggt tta tct tcg aca ggt cct gct gca gca cta att gcg tct agt att     1678
Gly Leu Ser Ser Thr Gly Pro Ala Ala Ala Leu Ile Ala Ser Ser Ile
                310                 315                 320

tct tta gca atc agt cca ttg gcg ttt tta cgt gta gct gat aat ttt     1726
Ser Leu Ala Ile Ser Pro Leu Ala Phe Leu Arg Val Ala Asp Asn Phe
            325                 330                 335

aat cgt tct aaa gaa att ggc gaa ttt gct gaa cgt ttc aaa aaa ttg     1774
Asn Arg Ser Lys Glu Ile Gly Glu Phe Ala Glu Arg Phe Lys Lys Leu
        340                 345                 350

ggc tat gac ggc gat aaa cta ctt tca gag ttt tat cac gaa gct ggt     1822
```

-continued

```
Gly Tyr Asp Gly Asp Lys Leu Leu Ser Glu Phe Tyr His Glu Ala Gly
    355                 360                 365

act att gat gcc tca att act aca att agt aca gca ctt tct gct atc     1870
Thr Ile Asp Ala Ser Ile Thr Thr Ile Ser Thr Ala Leu Ser Ala Ile
370                 375                 380                 385

gca gct gga acg gcc gcc gcg agt gca ggt gca tta gtt ggc gca cca     1918
Ala Ala Gly Thr Ala Ala Ala Ser Ala Gly Ala Leu Val Gly Ala Pro
                390                 395                 400

att act ttg ttg gtt act ggt atc aca gga tta att tct ggt att tta     1966
Ile Thr Leu Leu Val Thr Gly Ile Thr Gly Leu Ile Ser Gly Ile Leu
            405                 410                 415

gag ttc tct aaa caa cca atg tta gat cat gtt gca tcg aaa att ggt     2014
Glu Phe Ser Lys Gln Pro Met Leu Asp His Val Ala Ser Lys Ile Gly
        420                 425                 430

aac aaa att gac gaa tgg gag aaa aaa tac ggt aaa aat tac ttc gag     2062
Asn Lys Ile Asp Glu Trp Glu Lys Lys Tyr Gly Lys Asn Tyr Phe Glu
    435                 440                 445

aat ggc tat gat gct cgt cat aaa gct ttc tta gaa gat tca ttc tca     2110
Asn Gly Tyr Asp Ala Arg His Lys Ala Phe Leu Glu Asp Ser Phe Ser
450                 455                 460                 465

tta ttg tct agt ttt aat aaa caa tat gaa act gaa aga gct gtt tta     2158
Leu Leu Ser Ser Phe Asn Lys Gln Tyr Glu Thr Glu Arg Ala Val Leu
                470                 475                 480

att aca caa caa cgt tgg gat gaa tat att ggc gaa ctt gcg ggt att     2206
Ile Thr Gln Gln Arg Trp Asp Glu Tyr Ile Gly Glu Leu Ala Gly Ile
            485                 490                 495

act ggc aaa ggt gac aaa ctc tct agt ggt aag gcg tat gta gat tac     2254
Thr Gly Lys Gly Asp Lys Leu Ser Ser Gly Lys Ala Tyr Val Asp Tyr
        500                 505                 510

ttt caa gaa ggt aaa tta tta gag aaa aaa cct gat gac ttt agc aaa     2302
Phe Gln Glu Gly Lys Leu Leu Glu Lys Lys Pro Asp Asp Phe Ser Lys
    515                 520                 525

gta gtt ttc gat cca act aag ggc gaa att gat att tca aat agc caa     2350
Val Val Phe Asp Pro Thr Lys Gly Glu Ile Asp Ile Ser Asn Ser Gln
530                 535                 540                 545

acg tca acg ttg tta aaa ttt gtt acg cca tta tta aca cca ggt aca     2398
Thr Ser Thr Leu Leu Lys Phe Val Thr Pro Leu Leu Thr Pro Gly Thr
                550                 555                 560

gag tca cgt gaa aga act caa aca ggt aat tat gaa tat atc acg aag     2446
Glu Ser Arg Glu Arg Thr Gln Thr Gly Asn Tyr Glu Tyr Ile Thr Lys
            565                 570                 575

tta gtt gta aaa ggt aaa gat aaa tgg gtt gtt aat ggc gtt aaa gat     2494
Leu Val Val Lys Gly Lys Asp Lys Trp Val Val Asn Gly Val Lys Asp
        580                 585                 590

aaa ggt gcc gtt tat gat tat act aat tta att caa cat gct cat att     2542
Lys Gly Ala Val Tyr Asp Tyr Thr Asn Leu Ile Gln His Ala His Ile
    595                 600                 605

act tca tca gta gca cgt ggt gaa gaa tac cgt gaa gtt cgt ttg gta     2590
Thr Ser Ser Val Ala Arg Gly Glu Glu Tyr Arg Glu Val Arg Leu Val
610                 615                 620                 625

tct cat cta ggc aat ggt aat gac aaa gtg ttc tta gtc gcg ggt tcc     2638
Ser His Leu Gly Asn Gly Asn Asp Lys Val Phe Leu Val Ala Gly Ser
                630                 635                 640

gca gaa att cac gct ggt gaa ggt cat gat gtg gtt tat tat gat aaa     2686
Ala Glu Ile His Ala Gly Glu Gly His Asp Val Val Tyr Tyr Asp Lys
            645                 650                 655

acc gat aca ggt ctt tta gta att gat gga acc aaa gcg act gaa caa     2734
Thr Asp Thr Gly Leu Leu Val Ile Asp Gly Thr Lys Ala Thr Glu Gln
        660                 665                 670
```

-continued

```
ggg cgt tat tct gtt acg cgc gaa ttg agt ggt gct aca aaa atc ctg     2782
Gly Arg Tyr Ser Val Thr Arg Glu Leu Ser Gly Ala Thr Lys Ile Leu
    675                 680                 685

aga gaa gta ata aaa aat caa aaa tct gct gtt ggt aaa cgt gaa gaa     2830
Arg Glu Val Ile Lys Asn Gln Lys Ser Ala Val Gly Lys Arg Glu Glu
690                 695                 700                 705

acc ttg gaa tat cgt gat tat gaa tta acg caa tca ggt aat agt aac     2878
Thr Leu Glu Tyr Arg Asp Tyr Glu Leu Thr Gln Ser Gly Asn Ser Asn
                710                 715                 720

cta aaa gca cat gat gaa tta cat tca gta gaa gaa att att gga agt     2926
Leu Lys Ala His Asp Glu Leu His Ser Val Glu Glu Ile Ile Gly Ser
            725                 730                 735

aat cag aga gac gaa ttt aaa ggt agt aaa ttc aga gat att ttc cat     2974
Asn Gln Arg Asp Glu Phe Lys Gly Ser Lys Phe Arg Asp Ile Phe His
        740                 745                 750

ggt gcc gat ggt gat gat cta tta aat ggt aat gat ggg gat gat att     3022
Gly Ala Asp Gly Asp Asp Leu Leu Asn Gly Asn Asp Gly Asp Asp Ile
    755                 760                 765

cta tac ggt gat aaa ggt aac gat gag tta aga ggt gat aat ggt aac     3070
Leu Tyr Gly Asp Lys Gly Asn Asp Glu Leu Arg Gly Asp Asn Gly Asn
770                 775                 780                 785

gac caa ctt tat ggt ggt gaa ggt aat gac aaa cta tta gga ggt aat     3118
Asp Gln Leu Tyr Gly Gly Glu Gly Asn Asp Lys Leu Leu Gly Gly Asn
                790                 795                 800

ggc aat aat tac ctc agt ggt ggt gat ggc aat gat gag ctt caa gtc     3166
Gly Asn Asn Tyr Leu Ser Gly Gly Asp Gly Asn Asp Glu Leu Gln Val
            805                 810                 815

tta ggc aaa tgg ttt tta atg tgc ttc gtg gcg gta aag gcg atg ata     3214
Leu Gly Lys Trp Phe Leu Met Cys Phe Val Ala Val Lys Ala Met Ile
        820                 825                 830

aac ttt atg gta gct cag gtt ctg att tac ctt gat ggt gga gaa ggt     3262
Asn Phe Met Val Ala Gln Val Leu Ile Tyr Leu Asp Gly Gly Glu Gly
    835                 840                 845

aat gat tat cta gaa gga ggc gat ggt agc gat ttt tat gtt tac tgt     3310
Asn Asp Tyr Leu Glu Gly Gly Asp Gly Ser Asp Phe Tyr Val Tyr Cys
850                 855                 860                 865

tcc act tca ggt aat cat act att tat gat caa ggt aaa tct agt gat     3358
Ser Thr Ser Gly Asn His Thr Ile Tyr Asp Gln Gly Lys Ser Ser Asp
                870                 875                 880

tta gat aaa cta tat ttg tct gat ttt tcc ttc gat cgt ctt ctt gtt     3406
Leu Asp Lys Leu Tyr Leu Ser Asp Phe Ser Phe Asp Arg Leu Leu Val
            885                 890                 895

gag aaa gtt gat gat aac ctt gta ctt aga agt aat gaa agt agt cat     3454
Glu Lys Val Asp Asp Asn Leu Val Leu Arg Ser Asn Glu Ser Ser His
        900                 905                 910

aat aat gga gta ctc aca atc aaa gac tgg ttt aaa gaa ggg aat aaa     3502
Asn Asn Gly Val Leu Thr Ile Lys Asp Trp Phe Lys Glu Gly Asn Lys
    915                 920                 925

tat aac cat aaa att gaa caa att gtt gat aaa aat ggt aga aaa ttg     3550
Tyr Asn His Lys Ile Glu Gln Ile Val Asp Lys Asn Gly Arg Lys Leu
930                 935                 940                 945

aca gca gag aat tta gga act tat ttc aaa aat gct cca aaa gct gac     3598
Thr Ala Glu Asn Leu Gly Thr Tyr Phe Lys Asn Ala Pro Lys Ala Asp
                950                 955                 960

aat ttg ctt aat tat gca act aaa gaa gat cag aat gaa agc aat tta     3646
Asn Leu Leu Asn Tyr Ala Thr Lys Glu Asp Gln Asn Glu Ser Asn Leu
            965                 970                 975

tct tca ctt aaa act gaa tta agt aaa att att act aat gca ggt aat     3694
Ser Ser Leu Lys Thr Glu Leu Ser Lys Ile Ile Thr Asn Ala Gly Asn
        980                 985                 990
```

-continued

```
ttt ggt gtg gca aaa caa ggt aat act gga atc aat aca gct gcc ttg     3742
Phe Gly Val Ala Lys Gln Gly Asn Thr Gly Ile Asn Thr Ala Ala Leu
     995                1000                1005

aac aat gaa gtg aat aaa atc att tct tct gct aat acc ttt gct act     3790
Asn Asn Glu Val Asn Lys Ile Ile Ser Ser Ala Asn Thr Phe Ala Thr
1010                1015                1020                1025

tca caa ttg ggt ggc tca ggg atg gga aca tta cca tca acg aat gta     3838
Ser Gln Leu Gly Gly Ser Gly Met Gly Thr Leu Pro Ser Thr Asn Val
                1030                1035                1040

aat tca atg atg cta ggt aac cta gct aga gca gct taa tcatctgcat      3887
Asn Ser Met Met Leu Gly Asn Leu Ala Arg Ala Ala
            1045                1050

aatcaatagc aatcctatgg ctattctagg attgctattt tatttatgga gtcacaaatg   3947

ccttttaacg aaaaaataga ttacggatta catgcattgg taattctcgc gcaatatcac   4007

aatgttgccg taaaccctga agaggtaaaa cataaatttg atcttgatgg caaaggattg   4067

gatcttgttg cttggttatt agcagcaaaa tcattagaat taaaagccaa acgagtaaaa   4127

aagagtattg agcgtttacc atttattcat cttcctgctt taatctggcg agatgatggt   4187

caa                                                                 4190


<210> SEQ ID NO 10
<211> LENGTH: 1053
<212> TYPE: PRT
<213> ORGANISM: Actinobacillus pleuropneumonia

<400> SEQUENCE: 10

Met Ser Thr Trp Ser Ser Met Leu Ala Asp Leu Lys Lys Gly Ala Glu
 1               5                  10                  15

Glu Ala Lys Arg Gln Ala Lys Lys Gly Tyr Asp Val Thr Lys Asn Gly
            20                  25                  30

Leu Gln Tyr Gly Val Ser Gln Ala Lys Leu Gln Ala Leu Gly Ala Gly
        35                  40                  45

Lys Ala Val Gln Lys Tyr Gly Asn Lys Leu Val Leu Val Ile Pro Lys
    50                  55                  60

Glu Tyr Asp Gly Ser Val Gly Asn Gly Phe Phe Asp Leu Val Lys Ala
65                  70                  75                  80

Ala Glu Glu Leu Gly Ile Gln Val Lys Tyr Val Asn Arg Asn Glu Leu
                85                  90                  95

Glu Val Ala His Lys Thr Leu Gly Thr Ala Asp Gln Phe Leu Gly Leu
            100                 105                 110

Thr Glu Arg Gly Leu Thr Leu Phe Ala Pro Gln Leu Asp Gln Phe Leu
        115                 120                 125

Gln Lys His Ser Lys Ile Ser Asn Val Val Gly Ser Ser Thr Gly Asp
    130                 135                 140

Ala Val Ser Lys Leu Ala Lys Ser Gln Thr Ile Ile Ser Gly Ile Gln
145                 150                 155                 160

Ser Val Leu Gly Thr Val Leu Ala Gly Ile Asn Leu Asn Glu Ala Ile
                165                 170                 175

Ile Ser Gly Gly Ser Glu Leu Glu Leu Ala Glu Ala Gly Val Ser Leu
            180                 185                 190

Ala Ser Glu Leu Leu Ser Asn Ile Ala Lys Gly Thr Thr Thr Ile Asp
        195                 200                 205

Ala Phe Thr Thr Gln Ile Gln Asn Phe Gly Lys Leu Val Glu Asn Ala
    210                 215                 220
```

-continued

```
Lys Gly Leu Gly Gly Val Gly Arg Gln Leu Gln Asn Ile Ser Gly Ser
225                 230                 235                 240

Ala Leu Ser Lys Thr Gly Leu Gly Leu Asp Ile Ile Ser Ser Leu Leu
                245                 250                 255

Ser Gly Val Thr Ala Ser Phe Ala Leu Ala Asn Lys Asn Ala Ser Thr
            260                 265                 270

Ser Thr Lys Val Ala Ala Gly Phe Glu Leu Ser Asn Gln Val Ile Gly
        275                 280                 285

Gly Ile Thr Lys Ala Val Ser Ser Tyr Ile Leu Ala Gln Arg Leu Ala
    290                 295                 300

Ala Gly Leu Ser Ser Thr Gly Pro Ala Ala Ala Leu Ile Ala Ser Ser
305                 310                 315                 320

Ile Ser Leu Ala Ile Ser Pro Leu Ala Phe Leu Arg Val Ala Asp Asn
                325                 330                 335

Phe Asn Arg Ser Lys Glu Ile Gly Glu Phe Ala Glu Arg Phe Lys Lys
            340                 345                 350

Leu Gly Tyr Asp Gly Asp Lys Leu Leu Ser Glu Phe Tyr His Glu Ala
        355                 360                 365

Gly Thr Ile Asp Ala Ser Ile Thr Thr Ile Ser Thr Ala Leu Ser Ala
    370                 375                 380

Ile Ala Ala Gly Thr Ala Ala Ala Ser Ala Gly Ala Leu Val Gly Ala
385                 390                 395                 400

Pro Ile Thr Leu Leu Val Thr Gly Ile Thr Gly Leu Ile Ser Gly Ile
                405                 410                 415

Leu Glu Phe Ser Lys Gln Pro Met Leu Asp His Val Ala Ser Lys Ile
            420                 425                 430

Gly Asn Lys Ile Asp Glu Trp Glu Lys Lys Tyr Gly Lys Asn Tyr Phe
        435                 440                 445

Glu Asn Gly Tyr Asp Ala Arg His Lys Ala Phe Leu Glu Asp Ser Phe
    450                 455                 460

Ser Leu Leu Ser Ser Phe Asn Lys Gln Tyr Glu Thr Glu Arg Ala Val
465                 470                 475                 480

Leu Ile Thr Gln Gln Arg Trp Asp Glu Tyr Ile Gly Glu Leu Ala Gly
                485                 490                 495

Ile Thr Gly Lys Gly Asp Lys Leu Ser Ser Gly Lys Ala Tyr Val Asp
            500                 505                 510

Tyr Phe Gln Glu Gly Lys Leu Leu Glu Lys Lys Pro Asp Asp Phe Ser
        515                 520                 525

Lys Val Val Phe Asp Pro Thr Lys Gly Glu Ile Asp Ile Ser Asn Ser
    530                 535                 540

Gln Thr Ser Thr Leu Leu Lys Phe Val Thr Pro Leu Leu Thr Pro Gly
545                 550                 555                 560

Thr Glu Ser Arg Glu Arg Thr Gln Thr Gly Asn Tyr Glu Tyr Ile Thr
                565                 570                 575

Lys Leu Val Val Lys Gly Lys Asp Lys Trp Val Val Asn Gly Val Lys
            580                 585                 590

Asp Lys Gly Ala Val Tyr Asp Tyr Thr Asn Leu Ile Gln His Ala His
        595                 600                 605

Ile Thr Ser Ser Val Ala Arg Gly Glu Glu Tyr Arg Glu Val Arg Leu
    610                 615                 620

Val Ser His Leu Gly Asn Gly Asn Asp Lys Val Phe Leu Val Ala Gly
625                 630                 635                 640

Ser Ala Glu Ile His Ala Gly Glu Gly His Asp Val Val Tyr Tyr Asp
```

-continued

```
                645                 650                 655

Lys Thr Asp Thr Gly Leu Leu Val Ile Asp Gly Thr Lys Ala Thr Glu
            660                 665                 670

Gln Gly Arg Tyr Ser Val Thr Arg Glu Leu Ser Gly Ala Thr Lys Ile
        675                 680                 685

Leu Arg Glu Val Ile Lys Asn Gln Lys Ser Ala Val Gly Lys Arg Glu
    690                 695                 700

Glu Thr Leu Glu Tyr Arg Asp Tyr Glu Leu Thr Gln Ser Gly Asn Ser
705                 710                 715                 720

Asn Leu Lys Ala His Asp Glu Leu His Ser Val Glu Glu Ile Ile Gly
                725                 730                 735

Ser Asn Gln Arg Asp Glu Phe Lys Gly Ser Lys Phe Arg Asp Ile Phe
            740                 745                 750

His Gly Ala Asp Gly Asp Asp Leu Leu Asn Gly Asn Asp Gly Asp Asp
        755                 760                 765

Ile Leu Tyr Gly Asp Lys Gly Asn Asp Glu Leu Arg Gly Asp Asn Gly
    770                 775                 780

Asn Asp Gln Leu Tyr Gly Gly Glu Gly Asn Asp Lys Leu Leu Gly Gly
785                 790                 795                 800

Asn Gly Asn Asn Tyr Leu Ser Gly Gly Asp Gly Asn Asp Glu Leu Gln
                805                 810                 815

Val Leu Gly Lys Trp Phe Leu Met Cys Phe Val Ala Val Lys Ala Met
            820                 825                 830

Ile Asn Phe Met Val Ala Gln Val Leu Ile Tyr Leu Asp Gly Gly Glu
        835                 840                 845

Gly Asn Asp Tyr Leu Glu Gly Gly Asp Gly Ser Asp Phe Tyr Val Tyr
    850                 855                 860

Cys Ser Thr Ser Gly Asn His Thr Ile Tyr Asp Gln Gly Lys Ser Ser
865                 870                 875                 880

Asp Leu Asp Lys Leu Tyr Leu Ser Asp Phe Ser Phe Asp Arg Leu Leu
                885                 890                 895

Val Glu Lys Val Asp Asp Asn Leu Val Leu Arg Ser Asn Glu Ser Ser
            900                 905                 910

His Asn Asn Gly Val Leu Thr Ile Lys Asp Trp Phe Lys Glu Gly Asn
        915                 920                 925

Lys Tyr Asn His Lys Ile Glu Gln Ile Val Asp Lys Asn Gly Arg Lys
    930                 935                 940

Leu Thr Ala Glu Asn Leu Gly Thr Tyr Phe Lys Asn Ala Pro Lys Ala
945                 950                 955                 960

Asp Asn Leu Leu Asn Tyr Ala Thr Lys Glu Asp Gln Asn Glu Ser Asn
                965                 970                 975

Leu Ser Ser Leu Lys Thr Glu Leu Ser Lys Ile Ile Thr Asn Ala Gly
            980                 985                 990

Asn Phe Gly Val Ala Lys Gln Gly Asn Thr Gly Ile Asn Thr Ala Ala
        995                 1000                1005

Leu Asn Asn Glu Val Asn Lys Ile Ile Ser Ser Ala Asn Thr Phe Ala
    1010                1015                1020

Thr Ser Gln Leu Gly Gly Ser Gly Met Gly Thr Leu Pro Ser Thr Asn
1025                1030                1035                1040

Val Asn Ser Met Met Leu Gly Asn Leu Ala Arg Ala Ala
                1045                1050
```

<210> SEQ ID NO 11

-continued

```
<211> LENGTH: 22
<212> TYPE: DNA
<213> ORGANISM: Artificial Sequence
<220> FEATURE:
<223> OTHER INFORMATION: Oligonucleotide 284, modification of ClyIIC

<400> SEQUENCE: 11

attaatgcgg ccgcaggacc ag                                              22


<210> SEQ ID NO 12
<211> LENGTH: 22
<212> TYPE: DNA
<213> ORGANISM: Artificial Sequence
<220> FEATURE:
<223> OTHER INFORMATION: Oligonucleotide 285, modification of ClyIIC

<400> SEQUENCE: 12

acaaaagcgg ccgcatctta ca                                              22


<210> SEQ ID NO 13
<211> LENGTH: 22
<212> TYPE: DNA
<213> ORGANISM: Artificial Sequence
<220> FEATURE:
<223> OTHER INFORMATION: Oligonucleotide 286, modification of ClyIIC

<400> SEQUENCE: 13

ctacagctaa accaaagatc ct                                              22


<210> SEQ ID NO 14
<211> LENGTH: 15
<212> TYPE: DNA
<213> ORGANISM: Artificial Sequence
<220> FEATURE:
<223> OTHER INFORMATION: Oligonucleotide 158, modification of ClyIIC

<400> SEQUENCE: 14

cgtaggtgtt gcccc                                                      15


<210> SEQ ID NO 15
<211> LENGTH: 20
<212> TYPE: DNA
<213> ORGANISM: Artificial Sequence
<220> FEATURE:
<223> OTHER INFORMATION: Oligonucleotide 322, modification of ClyIIC

<400> SEQUENCE: 15

attcaataag cttgagccgc                                                 20
```